US010813979B2

(12) United States Patent
Fu et al.

(10) Patent No.: US 10,813,979 B2
(45) Date of Patent: Oct. 27, 2020

(54) METHODS AND COMPOSITIONS FOR TREATING NEURODEGENERATIVE AND NEUROINFLAMMATORY CONDITIONS

(71) Applicant: The Hong Kong University of Science and Technology, Hong Kong (CN)

(72) Inventors: Kit Yu Fu, Hong Kong (CN); Foo Yew Liew, Glasgow (GB); Nancy Yuk-Yu Ip, Hong Kong (CN)

(73) Assignee: The Hong Kong University of Science and Technology, Hong Kong (CN)

(*) Notice: Subject to any disclaimer, the term of this patent is extended or adjusted under 35 U.S.C. 154(b) by 0 days.

(21) Appl. No.: 15/742,582

(22) PCT Filed: Jul. 7, 2016

(86) PCT No.: PCT/IB2016/054080
§ 371 (c)(1),
(2) Date: Jan. 8, 2018

(87) PCT Pub. No.: WO2017/009750
PCT Pub. Date: Jan. 19, 2017

(65) Prior Publication Data
US 2019/0015480 A1   Jan. 17, 2019

Related U.S. Application Data

(60) Provisional application No. 62/191,173, filed on Jul. 10, 2015.

(51) Int. Cl.
| A61K 38/20 | (2006.01) |
| A61K 31/13 | (2006.01) |
| A61P 25/28 | (2006.01) |
| A61K 45/06 | (2006.01) |
| G01N 33/68 | (2006.01) |
| C07K 14/00 | (2006.01) |
| A61K 31/55 | (2006.01) |
| A61K 31/27 | (2006.01) |
| A61K 31/445 | (2006.01) |
| A61K 31/4439 | (2006.01) |
| A61K 31/4178 | (2006.01) |
| A61P 25/16 | (2006.01) |

(52) U.S. Cl.
CPC .............. *A61K 38/20* (2013.01); *A61K 31/13* (2013.01); *A61K 31/27* (2013.01); *A61K 31/4178* (2013.01); *A61K 31/445* (2013.01); *A61K 31/4439* (2013.01); *A61K 31/55* (2013.01); *A61P 25/16* (2018.01); *A61P 25/28* (2018.01); *C07K 14/00* (2013.01); *G01N 33/6896* (2013.01); *A61K 45/06* (2013.01); *A61K 2300/00* (2013.01); *G01N 2333/7155* (2013.01); *G01N 2500/02* (2013.01); *G01N 2800/50* (2013.01); *G01N 2800/7095* (2013.01)

(58) Field of Classification Search
CPC ..... A61K 38/20; A61K 45/06; A61K 2300/00; A61P 25/16; A61P 25/28
See application file for complete search history.

(56) References Cited

U.S. PATENT DOCUMENTS

| 7,605,265 | B2 | 10/2009 | Ip et al. |
| 8,642,567 | B2 | 2/2014 | Ip et al. |
| 9,029,414 | B2 | 5/2015 | Ip et al. |
| 2005/0203046 | A1* | 9/2005 | Schmitz ............... C07K 16/244 514/44 A |
| 2013/0012462 | A1 | 1/2013 | Ip et al. |
| 2014/0105887 | A1 | 4/2014 | Chackerian et al. |
| 2014/0186357 | A1 | 7/2014 | Koh et al. |

FOREIGN PATENT DOCUMENTS

| WO | WO-02/086075 | 10/2002 | |
| WO | WO-2007130627 A2 * | 11/2007 | ............ A61K 38/20 |
| WO | WO-2014/128254 A1 | 8/2014 | |
| WO | WO-2015/007222 A1 | 1/2015 | |
| WO | WO-2016/019280 | 2/2016 | |

OTHER PUBLICATIONS

Ghezzi L et al. Disease-modifying drugs in Alzheimer's disease. Drug Design, Development & Therapy, 7:1471-1479. (Year: 2013).*
Stampfer MJ. Cardiovascular disease and Alzheimer's disease: common links. J. Internal Medicine, 260:211-223. (Year: 2006).*
Batzer, et al., "Enhanced evolutionary PCR using oligonucleotides with inosine at the 3'-terminus," Nucleic Acid Research, vol. 19, No. 18, Jul. 12, 1991, p. 5081.
Cayrol, et al., "The IL-1-like cytokine IL-33 is inactivated after maturation by caspase-1," PNAS, vol. 106, No. 22, Jun. 2, 2009, pp. 9021-9026.
Chackerian, et al., "IL-1 Receptor Accessory Protein and ST2 Comprise the IL-33 Receptor Complex," Journal of Immunology, vol. 179, Issue 4, Aug. 15, 2007, pp. 2551-2555.
Chapuis, et al., "Transcriptomic and genetic studies identify IL-33 as a candidate gene for Alzheimer's disease," Mol Psychiatry, vol. 14, Issue 11, Nov. 2009, pp. 1004-1016.
Fu, et al., "IL-33 ameliorates Alzheimer's disease-like pathology and congnitive decline," PNAS, vol. 113, No. 19, Apr. 18, 2016, pp. 2705-2713.
Hayakawa, et al., "Soluble ST2 Blocks Interleukin-33 Signaling in Allergic Airway Inflammation." Journal of Biological Chemistry, vol. 282, No. 36, Sep. 7, 2007, pp. 26369-26380.
Hofmann, et al., "Interactive computer-based cognitive training in patients with Alzheimer's disease," Journal Psychiatric Research, vol. 30, Issue 6, Nov.-Dec. 1996, pp. 493-501.
Humphreys, et al., "IL-33, a Potent Inducer of Adaptive Immunity to Intestinal Nematodes," Journal of Immunology, vol. 180, Issue 4, Feb. 15, 2008, pp. 2443-2449.

(Continued)

*Primary Examiner* — Kimberly Ballard
(74) *Attorney, Agent, or Firm* — Foley & Lardner LLP

(57) ABSTRACT

Methods, compositions, and kits for diagnosing or treating neurodegenerative or neuroinflammatory conditions are provided. Also provided are methods for identifying modulators of neurodegenerative or neuroinflammatory conditions.

3 Claims, 29 Drawing Sheets

Specification includes a Sequence Listing.

(56) References Cited

OTHER PUBLICATIONS

International Preliminary Report on Patentability issued on International Application No. PCT/162016/054080 dated Jan. 25, 2018 (8 pages).
International Search Report and Written Opinion dated Oct. 26, 2016 for International Application No. PCT/162016/054080 (13 pages).
Ip, et al., "Anemoside A3 Enhances Cognition through the Regulation of Synaptic Function and Neuroprotection," Neuropsychopharmacology, vol. 40, Feb. 2015, pp. 1877-1887.
Kakkar, et al., "The IL-33/ST2 pathway: therapeutic target and novel biomarker," Nature Reviews Drug Discovery, vol. 7, Issue 10, Oct. 2008, pp. 827-840.
Langer, "New Methods of Drug Delivery," Science, vol. 249, Issue 4976, Sep. 28, 1990, pp. 1527-1533.
Liew, et al., "Disease-associated functions of IL-33: the new kid in the IL-1 family," Nature Reviews Immunology, vol. 10, No. 2, Jan. 18, 2010, pp. 103-110.
Luthi, et al., "Suppression of Interleukin-33 Bioactivity through Proteolysis by Apoptotic Caspases," Immunity, vol. 31, Issue 1, Jul. 17, 2009, pp. 84-98.
Martin, "Special aspects of interleukin-33 and the IL-33 receptor complex," Seminars in Immunology, vol. 25, Issue 6, Dec. 15, 2013, pp. 449-457.
Miller, "Role of IL-33 in inflammation and disease," Journal of Inflammation, vol. 8, Issue 22, Aug. 26, 2011 (12 pages).
Moussion, et al., "The IL-1-Like Cytokine IL-33 Is Constitutively Expressed in the Nucleus of Endothelial Cells and Epithelial Cells In Vivo: A Novel 'Alarmin'," PLoS One, vol. 3, Issue 10, Oct. 6, 2008.
Oakley, et al., "Intraneuronal beta-amyloid aggregates, neurodegeneration, and neuron loss in transgenic mice with five familial Alzheimer's disease mutations: Potential factors in amyloid plaque formation," Journal of Neuroscience, vol. 26, Issue 40, Oct. 4, 2006, pp. 10129-10140.
Ohtsuka, et al., "An Alternative Approach to Deoxyoligonucleotides as Hybridization Probes by Insertion of Deoxyinosine at Ambiguous Codon Positions," Journal of Biological Chemistry, vol. 260, No. 5, Mar. 10, 1985, pp. 2605-2608.
Rossolini, et al, "Use of deoxyinosine-containing primers vs degenerate primers for polymerase chain reaction based on ambiguous sequence information," Molecular and Cellular Probes, vol. 8, Issue 2, Apr. 1994, pp. 91-98.
Roussel, et al., "Molecular mimicry between IL-33 and KSHV for attachment to chromatin through the H2A-H2B acidic pocket," EMBO Reports, vol. 9, Issue 10, Oct. 2008, pp. 1006-1012.
Sananbenesi, et al., "A hippocampal Cdk5 pathway regulates extinction of contextual fear." Nature Neuroscience, vol. 10, Issue 8, 2007, pp. 1012-1019.
Sanchez, et al., "Levetiracetam suppresses neuronal network dysfunction and reverses synaptic and cognitive deficits in an Alzheimer's disease model," PNAS, vol. 109, Issue 42, Aug. 6, 2012, pp. 2895-2903.
Xiong, et al., "Alzheimer's Disease: Evidence for the Expression of Interleukin-33 and Its Receptor ST2," The Brain Journal of Alzheimers Disease, vol. 40, No. 2, Jan. 1, 2014, pp. 297-308.
Xu, et al., "IL-33 exacerbates antigen-induced arthritis by activating mast cells," PNAS, vol. 105, Issue 31, Aug. 5, 2008, pp. 10913-10918.
Yu, et al., "Implication of IL-33 gene polymorphism in Chinese patients with Alzheimer's disease," Neurobiology of Aging, vol. 33, Issue 5, May 2012, pp. 1011-1014.
Zhang, et al., "Parenchymal Microglia of Naive Adult C57BL/6J Mice Express High Levels of B7.1, B7.2, and MHC Class II," Experimental and Molecular Pathololgy, vol. 73, Issue 1, Aug. 2002, pp. 35-45.
Cherry et al, "Neuroinflammation and M2 microglia: the good, the bad, and the inflamed", Journal of Neuroinflammation, Biomed Central Ltd., London, GB, (Jun. 3, 2014), vol. 11, No. 1, p. 98.
Extended European search report issued for EP 16823957.2, dated Nov. 22, 2018.
Examination Report in EP Patent Application No. 16823957.2 dated Jan. 6, 2020 (5 pages).

* cited by examiner

FIG. 10C

| Cluster | Genes | p-value | Gene Ontology |
|---|---|---|---|
| C4 | MYD88 | 2.05E-02 | positive regulation of immune system process |
| | IRAK3 | 1.65E-02 | |
| | IL2RG | 2.44E-02 | |
| C5 | H2-Ab1 | 1.41E-02 | antigen processing and presentation of exogenous antigen |
| | H2-Aa | 1.53E-03 | |
| | H2-Eb1 | 2.90E-02 | |
| | AP3B1 | 3.07E-02 | |
| C6 | TNF | 2.11E-02 | Alzheimer's disease |
| | PSEN2 | 3.55E-03 | |
| | MAPK3 | 3.52E-02 | |
| | CALM1 | 8.06E-03 | |
| | ARF6 | 1.76E-02 | Fc gamma R-mediated phagocytosis |
| | ARPC1A | 8.05E-03 | |
| | ARPC1B | 3.91E-03 | |
| | ARPC3 | 2.43E-02 | |
| | MSR1 | 2.16E-02 | |
| | PIP5K1C | 3.16E-02 | |
| | CH25H | 2.68E-02 | Lipid synthesis / Cholesterol biosynthesis |
| | DHCR24 | 1.42E-02 | |
| | INSIG1 | 2.98E-03 | |
| | LDLR | 2.47E-03 | |

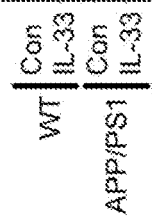

WT (Con, IL-33)    APP/PS1 (Con, IL-33)

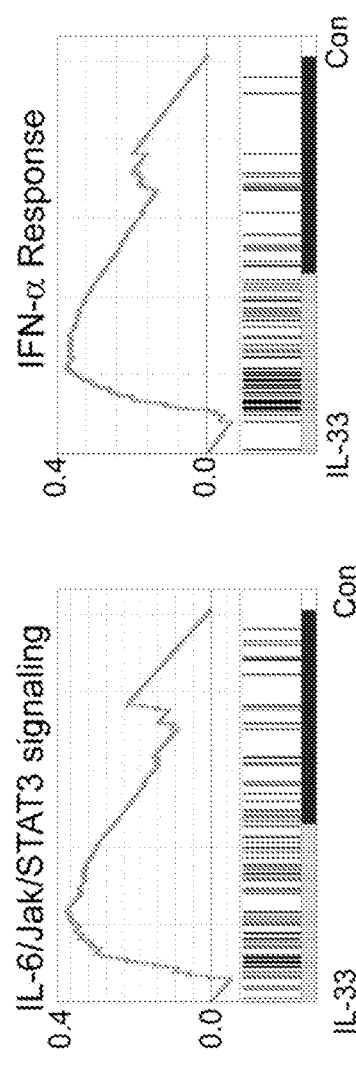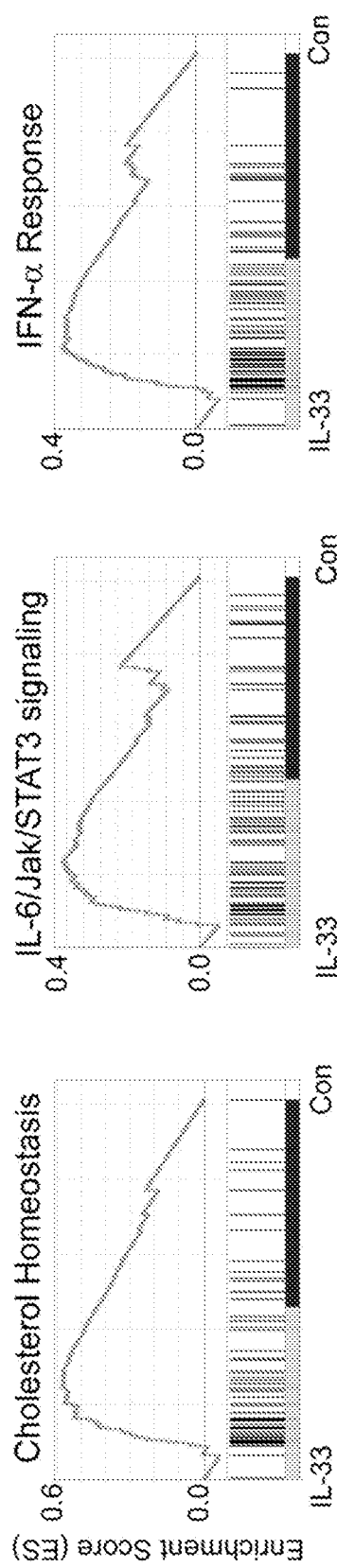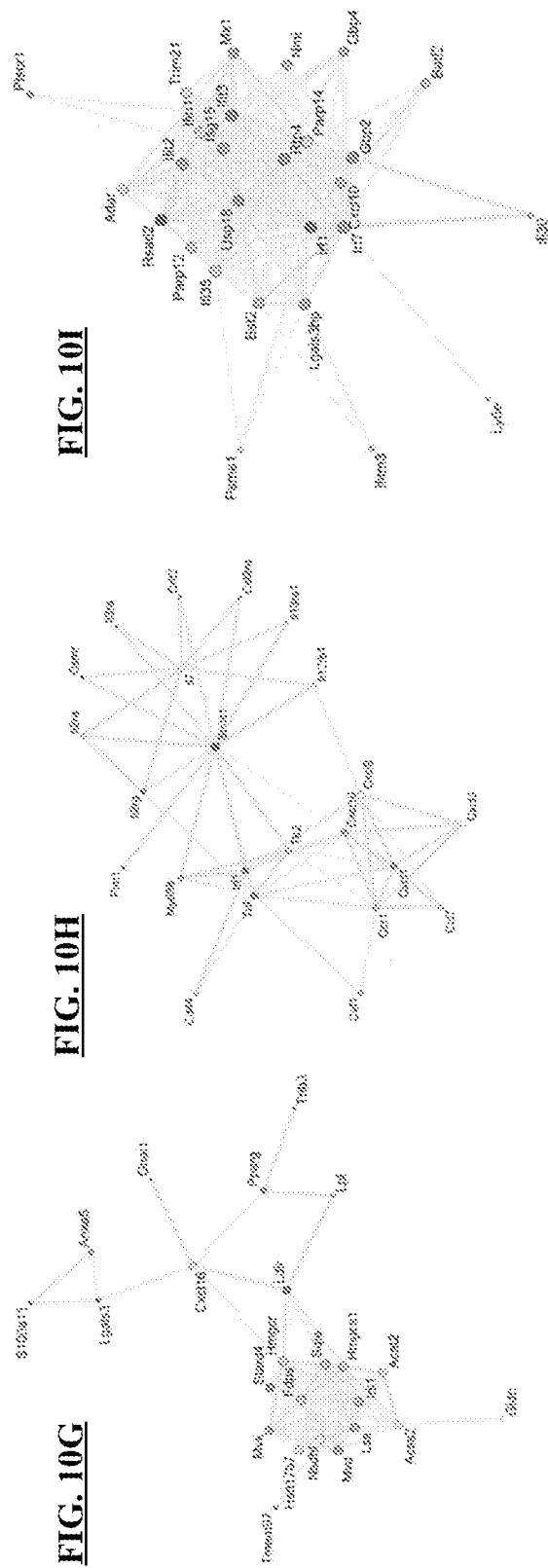
FIG. 10D  FIG. 10E  FIG. 10F
FIG. 10G  FIG. 10H  FIG. 10I

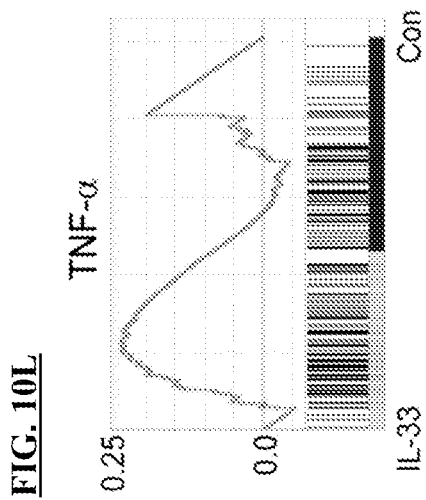
FIG. 10J  FIG. 10K  FIG. 10L
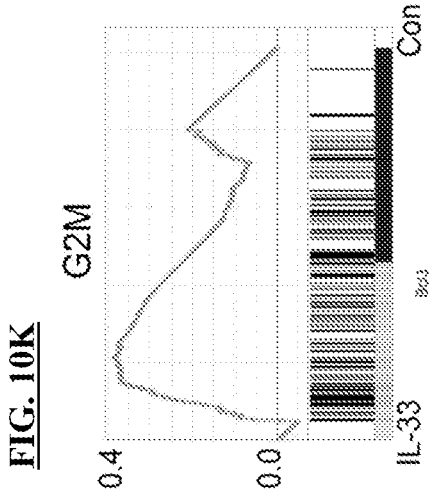
FIG. 10M  FIG. 10N  FIG. 10O

FIG. 14A
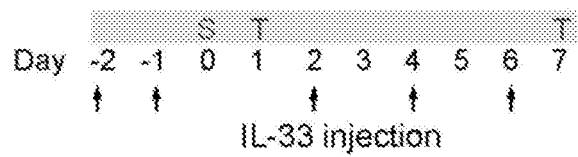
FIG. 14B
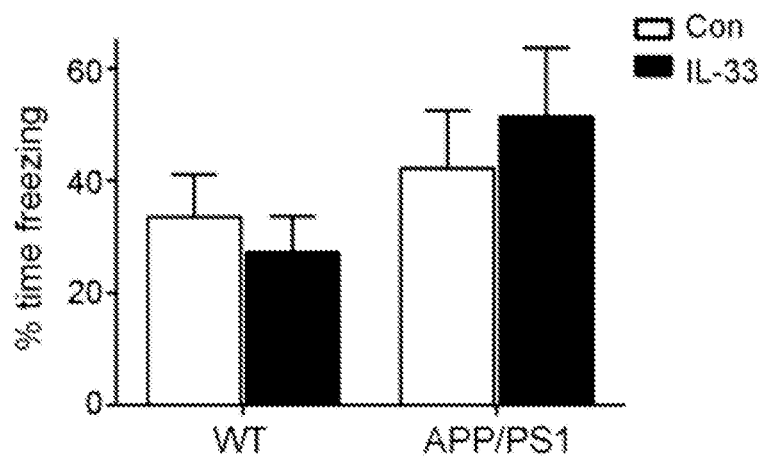
FIG. 14C
FIG. 14D
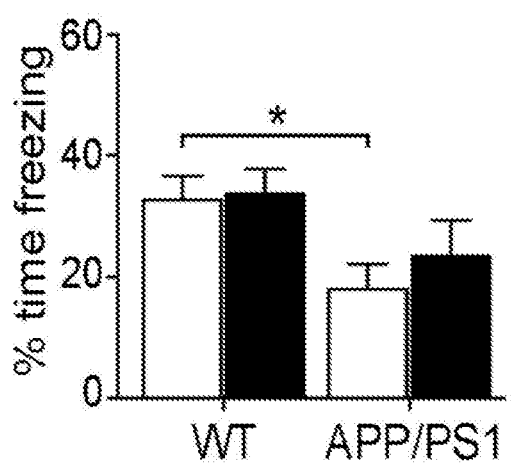
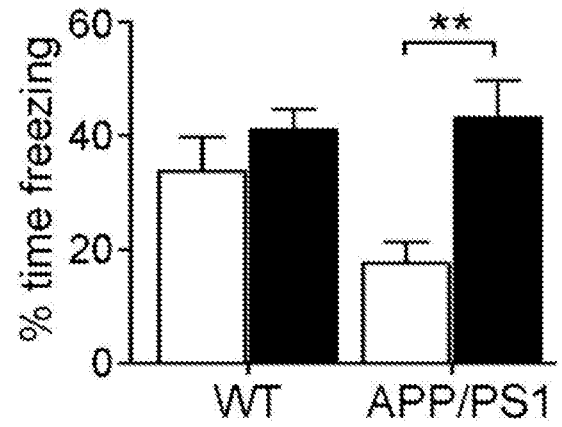

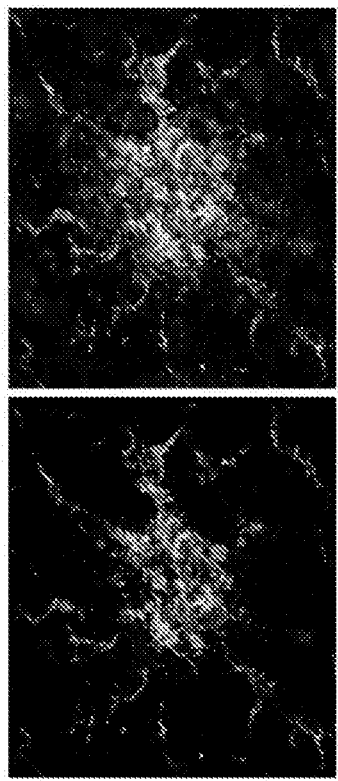
FIG. 16A Con
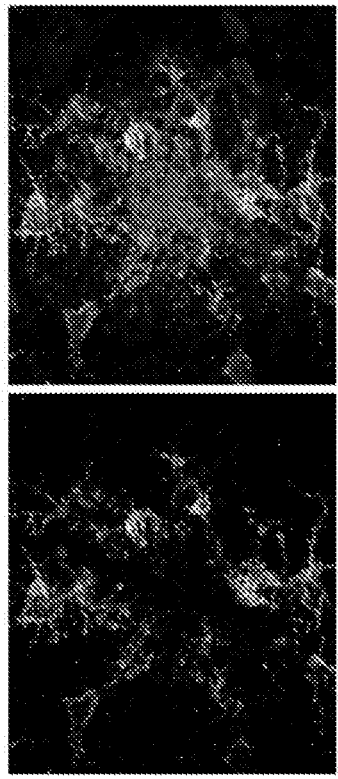
FIG. 16B IL-33
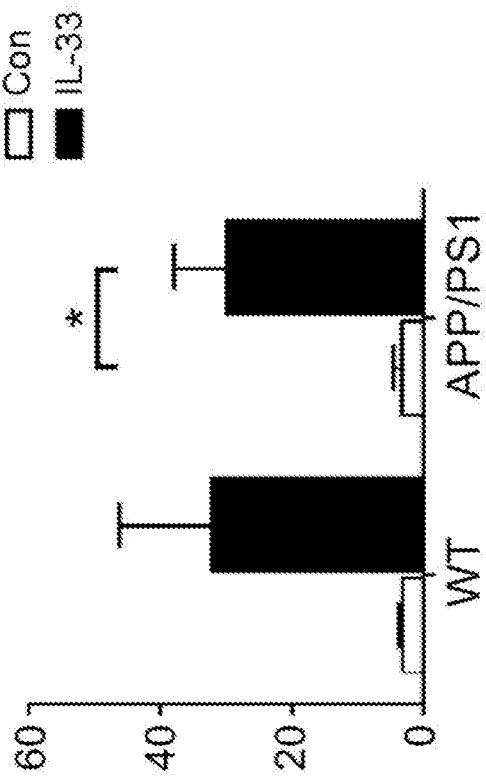
FIG. 17A
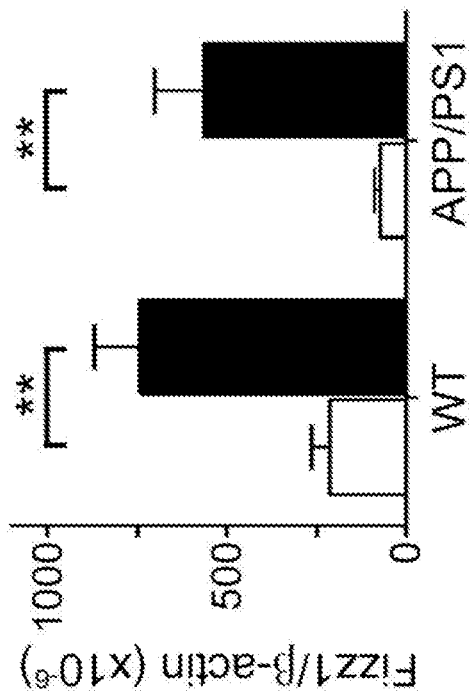
FIG. 17B

FIG. 20
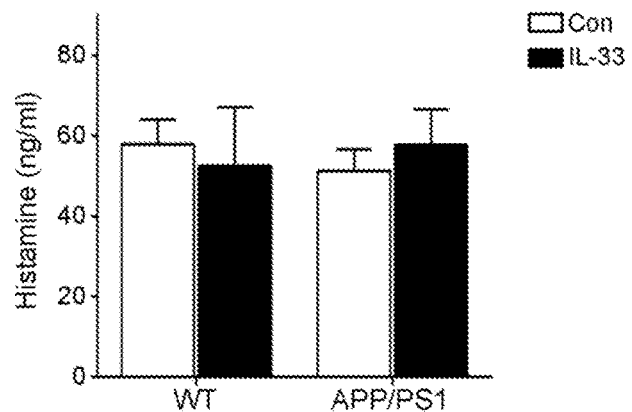
FIG. 21
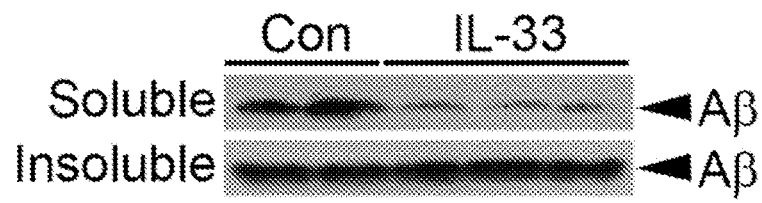
FIG. 22A      FIG. 22B
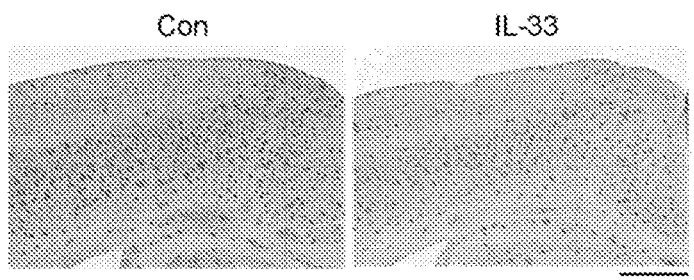  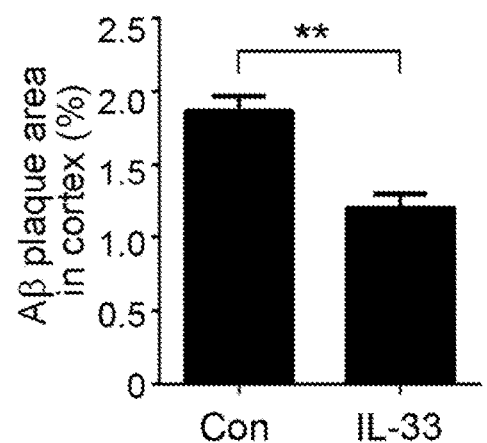

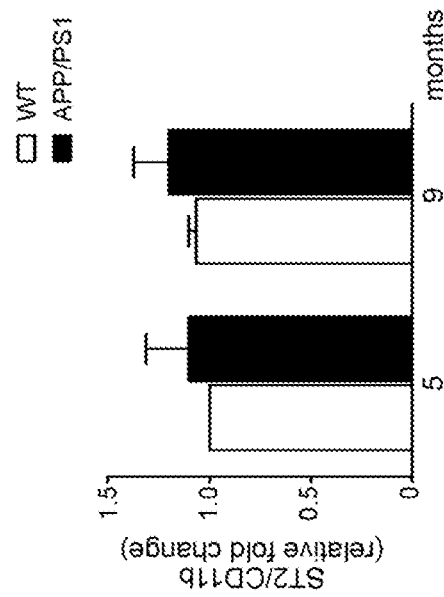
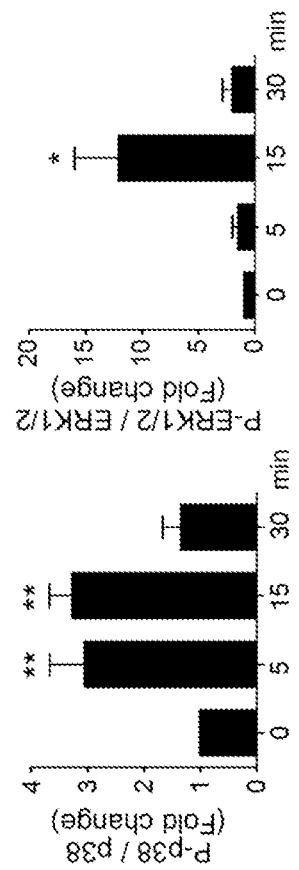
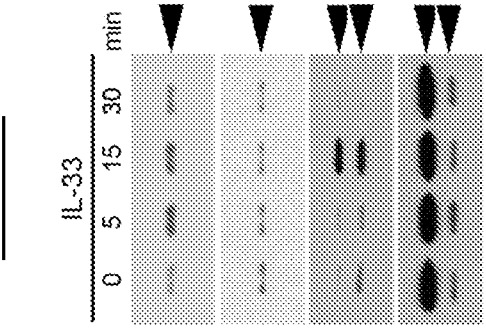
FIG. 26A
FIG. 26B
FIG. 26C
FIG. 26D

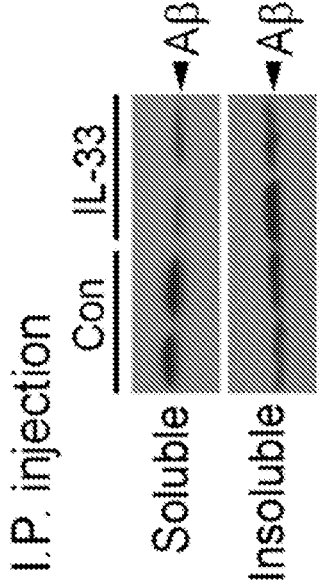
FIG. 27B
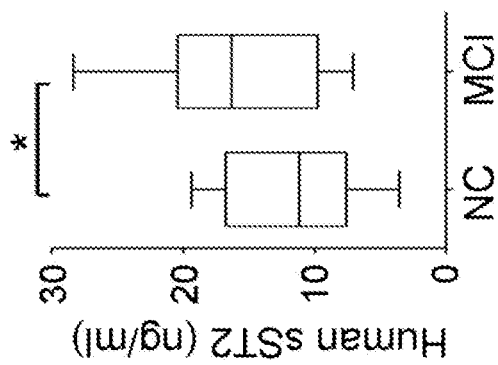
FIG. 27A
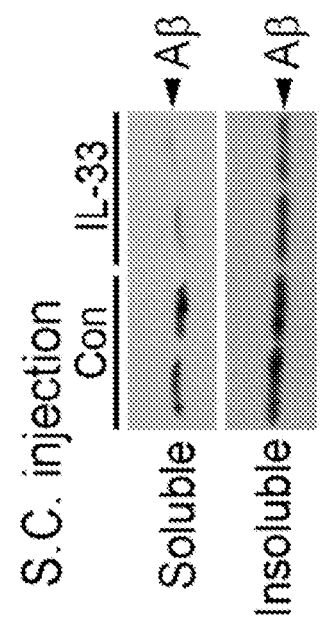
FIG. 28B
FIG. 28A

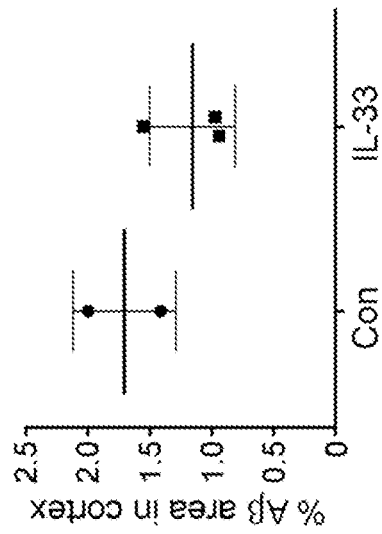
FIG. 32B
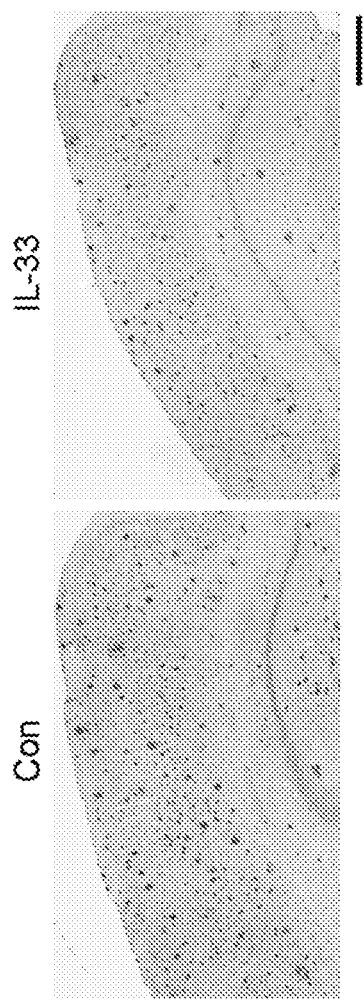
FIG. 32A
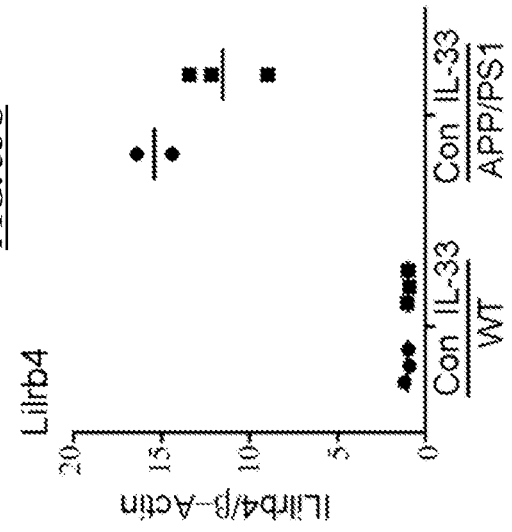
FIG. 33C
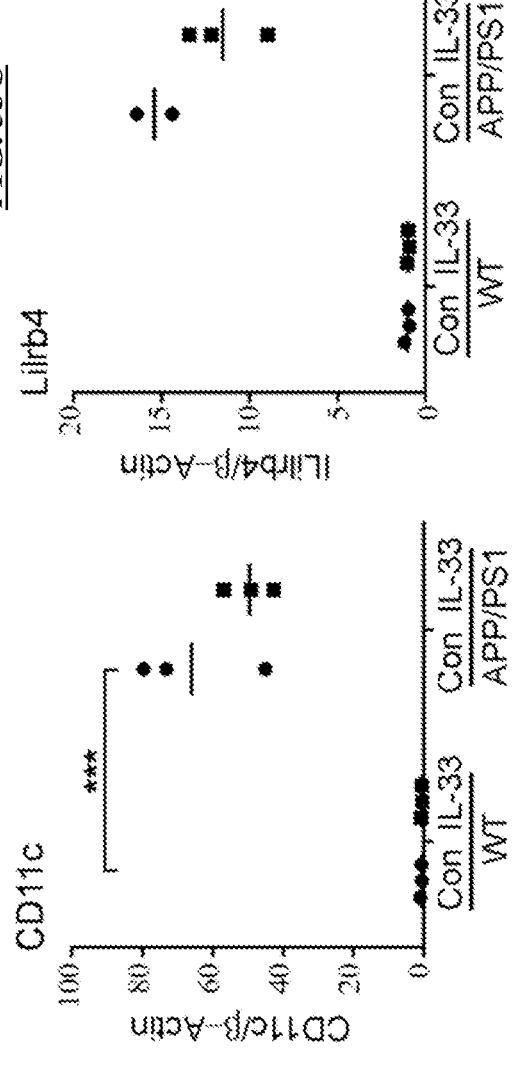
FIG. 33B
FIG. 33A

METHODS AND COMPOSITIONS FOR TREATING NEURODEGENERATIVE AND NEUROINFLAMMATORY CONDITIONS

CROSS-REFERENCE TO RELATED APPLICATION

This application is a U.S. National Phase application under 35 U.S.C. 371 of PCT/IB2016/054080, filed Jul. 7, 2016, which claims the benefit of U.S. Provisional Application No. 62/191,173, filed Jul. 10, 2015, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Apr. 13, 2018, is named 114334-0121_SL.txt and is 8,806 bytes in size.

TECHNICAL FIELD

The present technology relates generally to methods and compositions for diagnosing and treating neurodegenerative and neuroinflammatory conditions, and methods for identifying modulators of neurodegenerative or neuroinflammatory conditions for use in methods of treatment and prevention.

BACKGROUND

Brain diseases such as neurodegenerative diseases and neuroinflammatory disorders are devastating conditions that affect a large subset of the population. Many are presently incurable, highly debilitating, and often result in progressive deterioration of brain structure and function over time. Disease prevalence is also increasing rapidly due to growing aging populations worldwide, since the elderly are at high risk for developing these conditions. Currently, many neurodegenerative diseases and neuroinflammatory disorders are difficult to diagnose due to limited understanding of the pathophysiology of these diseases. Meanwhile, current treatments are ineffective and do not meet market demand; demand that is significantly increasing each year due to aging populations. For example: Alzheimer's disease (AD) is marked by gradual but progressive decline in learning and memory, and a leading cause of mortality in the elderly. Currently, an estimated 35 million people worldwide are afflicted with the disease but this figure is expected to rise significantly to 100 million by 2050 due to longer life expectancies. There is no cure; and the pathophysiology of the disease is still relatively unknown. There are only four FDA approved drugs available to AD patients, but these only alleviate symptoms rather than alter disease pathology (they cannot reverse the condition or prevent further deterioration) and are ineffective in severe conditions. Thus, early therapeutic intervention is critical in the management of AD. Research has confirmed that AD affects the brain long before actual symptoms of memory loss or cognitive decline actually manifest. However, there are no diagnostic tools for early detection and by the time a patient is diagnosed with AD using current methods, which involves subjective clinical assessment, the pathological symptoms are already at an advanced state. Mild cognitive impairment (MCI) is considered to be the prodromal stage of AD. Diagnostic tools to identify individuals with MCI are therefore essential for AD management.

Parkinson's disease (PD) is the world's second most prevalent neurodegenerative disease after AD. PD is a neurodegenerative disorder that mainly affects the motor system. The motor symptoms of the disease result from the death of dopamine-generating cells in the substantia nigra, a region of the midbrain. The most obvious disease symptoms are movement-related, which include shaking, rigidity, slowness of movement, and difficulty with walking and gait. As the disease progresses, thinking and behavior are affected, with dementia commonly occurring in the advanced stages of the disease. Depression is the most common psychiatric symptom associated with the disease. The major pathological hallmark of the disease is the accumulation of α-synuclein into inclusions called Lewy bodies in neurons, and the death of dopamine-generating cells in the substantia nigra. Currently, PD is diagnosed via clinical symptoms, which include tremors, bradykinesia, rigidity, and postural imbalance, since reliable diagnostic tests or markers for PD are not yet available. Worldwide, it is estimated that ~7 million people have PD. Furthermore, the number of cases is projected to grow significantly due to aging populations. In the US, the number of PD sufferers is predicted to nearly double; but the greatest growth will occur in developing countries in Asia such as China, which is predicted to have an estimated 5 million cases by 2030. However, the actual prevalence of PD is difficult to assess because as the disease is typically not diagnosed until the disease has progressed to an advanced state due to limitations on diagnostic methods.

Multiple sclerosis (MS) is an inflammatory degenerative disease where the myelin sheath protecting nerve cells in the brain and spinal cord of the central nervous system (CNS) are attacked by the immune system and damaged, thus preventing nerve cell communication within the CNS. The disease is characterized by various symptoms that can include blurry vision, loss of balance, poor coordination, slurred speech, tremors, numbness, extreme fatigue, problems with memory and concentration, paralysis, and blindness. There is no known cure for MS, while clinical interventions aim to improve function after an attack and prevent new attacks. Current drugs however, are moderately effective and have adverse side effects. Worldwide, ~2.3 million people are estimated to be affected by MS. However, MS is typically diagnosed based on signs and symptoms, and even in combination with supporting medical imaging and laboratory testing, diagnosis is difficult. This is especially true in the early stages when symptoms are invisible or similar to other medical conditions.

Other neurodegenerative and neuroinflammatory conditions include depression, stroke, dementia with Lewy bodies, amyotrophic lateral sclerosis, frontotemporal dementia, Huntington's disease, retinal degenerative diseases such as glaucoma age-related macular degeneration and diabetic retinopathy, hearing loss due to nerve degeneration, traumatic brain injury, and spinal cord injury, and other neuroinflammatory conditions such as acute disseminated encephalomyelitis, optic neuritis transverse myelitis post-polio syndrome, multifocal motor neuropathy, and chronic inflammatory demyelinating polyneuropathy. With rising prevalence of neurodegenerative and neuroinflammatory diseases and disorders, and their significant impact on human health, especially in the elderly, there remains an urgent need to develop new and effective strategies for the diagnosis, management, and treatment of brain diseases.

The present technology addresses this need by leveraging cytokine interleukin-33 (IL-33) and its negative regulator, soluble ST2 (sST2). IL-33 is a member of the IL-1 family, which includes IL-1α, IL-1β, and IL-18. Interleukins are important components of the immune system and play critical roles in immune responses. IL-33 mRNA is expressed in various organs (e.g., the central nervous system, lungs, and skin) and cell types (e.g., fibroblasts, macrophages, and glial cells) in humans and mice (Liew, F. Y., Pitman, N. I., & McInnes, I. B. Nature Reviews Immunology 10, 103-110 (2010)). Full-length IL-33 is biologically active but is localized in the nucleus where it exerts transcriptional regulation (Moussion, C., Ortega, N. & Girard, J. P. PLoS One 3, e3331 (2008)), while it can act as a traditional cytokine by releasing into the extracellular spaces upon receiving damage stimuli (Cayrol, C. & Girard, J. P. Proc Natl Acad Sci USA 106, 9021-9026 (2009)). In the nucleus, IL-33 modulates the chromatin architecture by binding to the histone H2A-H2B complex of nucleosomes (Roussel, L., Erard, M., Cayrol, C. & Girard, J. P. EMBO Rep 9, 1006-1012 (2008)), or associates with transcriptional factor NF-κB to suppress its transcriptional activity. IL-33 is cleaved by caspase-1 in the presence of other proteases. Besides caspase-1, caspase-7, and caspase-3, calpain mediates IL-33 cleavage. However, the cleavage products of IL-33 are biologically inactive (Lüthi A U, Cullen S P, McNeela E A, Duriez P J, Afonina I S, Sheridan C, Brumatti G, Taylor R C, Kersse K, Vandenabeele P, Lavelle E C, Martin S J. Immunity 3, 84-98 (2009)). Upon tissue injury or necrosis, IL-33 is released from the cell nuclei to trigger the inflammatory response in other cells (Liew, F. Y., Pitman, N. I., & McInnes, I. B. Nature Reviews Immunology 10, 103-110 (2010)).

The specific receptor for the released IL-33 is ST2 (also known as IL-1RL1). Upon binding to ST2 receptor, IL-33 induces the recruitment of interleukin-1 receptor accessory protein (IL-1RAcP) (Chackerian, A. A., et al. J Immunol 179, 2551-2555 (2007)) to the ST2 receptor and forms a heterodimer, to initiate a downstream signaling cascade. Several downstream signaling pathways are identified, for example MyD88/IRAK/TRAF6, PI3K/Akt/mTOR, Syk/PLCγ or JAK/STAT pathways. The activation of signaling pathway(s) depends on the cell types and the inflammatory conditions (Martin, M. U. Semin Immunol 25, 449-457 (2013)). ST2 determines the specificity of IL-33 signaling. The ST2 gene encodes different isoforms by alternative splicing: a full-length form (ST2L), secreted soluble form (sST2), and variant form (ST2V) (Miller, A. M., J Inflamm (Lond) 8, 22 (2011)). sST2 acts as a decoy receptor for IL-33 to inhibit the activation of IL-33/ST2 signaling (Hayakawa, H., Hayakawa, M., Kume, A. & Tominaga, S. J Biol Chem 282, 26369-26380 (2007)). Upon binding to the receptor complex, IL-33 recruits myeloid differentiation primary-response protein 88, IL-1 receptor-associated kinase 1 (IRAK1), and IRAK4 complex to stimulate the signaling of mitogen-activated protein kinase (MAPK) kinases and the transcription factor nuclear factor-κB (NF-κB). These two pathways mediate the production of different cytokines and chemokines in corresponding cell types (Liew, F. Y., Pitman, N. I., & McInnes, I. B, Nature Reviews Immunology 10, 103-110 (2010)).

IL-33 plays a dual role in diseases. First, it has an important protective function against infection. Mice infected with the influenza virus exhibit reduced pulmonary inflammation and pathology after IL-33 treatment (Liew, F. Y., Pitman, N. I., & McInnes. I. B. Nature Reviews Immunology 10, 103-110 (2010)). IL-33 mRNA levels are elevated in the colon of *Trichuris muris*-resistant mice (Humphreys et al. Journal of immunology 180, 2443-2449 (2008)). In contrast, IL-33 promotes the pathogenesis of T helper 2 (Th2) cell-related diseases including asthma, atopic dermatitis, and anaphylaxis by inducing cytokine production in Th2 cells and other innate immune cells (Kakkar, R. & Lee, R. T. Nature reviews Drug discovery 7, 827-840 (2008)). For example, asthma patients have higher IL-33 expression levels; concordantly, IL-33 administration exacerbates asthma pathology in mouse models of asthma. Intriguingly, three single nucleotide polymorphisms (SNPs) of IL-33 are associated with AD in Caucasian populations (Chapuis et al. Mol Psychiatry 14, 1004-1016 (2009)). One of the SNPs, rs1179633, is strongly associated with late-onset of Alzheimer's disease in Chinese populations (Yu et al. Neurobiology of aging 33, 1014 e1011-1014 (2012)). Additional evidence of the involvement of IL-33 in AD comes from the finding that IL-33 mRNA expression is decreased in human AD brains (Chapuis et al. Mol Psychiatry 14, 1004-1016 (2009)). There is also evidence that IL-33 and ST2-positive cells are significantly increased in the entorhinal cortex of AD patients, although this remains controversial. Furthermore, IL-33 and ST2 co-localize with amyloid plaques and neurofibrillary tangles in the brains of AD patients. In the aggregates, despite a discrepancy between mRNA and protein expression in AD brains, these findings suggest that the regulation of IL-33/ST2 signaling is important in AD pathology.

SUMMARY

In some aspects, the present disclosure provides a method for treating or reducing risk of neurodegeneration in a subject in need thereof, comprising administering to the subject an effective amount of a composition comprising IL-33.

In some embodiments, the subject suffers from or is at risk of suffering from Alzheimer's disease, mild cognitive impairment, Parkinson's disease, or multiple sclerosis. In some embodiments, the composition is administered subcutaneously, intraperitoneally, intravenously, intradermally, intracerebroventricularly, intrathecally, orally, by inhalation, transdermally, or transmucosally.

In some embodiments, the composition is co-administered with one or more additional therapeutically active agents. In some embodiments, the one or more additional therapeutically active agents is selected from the group consisting of donepezil, rivastigmine, galantamine, memantine, aducanumab, rosiglitazone, bexarotene, losartan, and rhynchophylline.

In some embodiments, the IL-33 is a recombinant IL-33 protein. In some embodiments, the IL-33 recombinant protein comprises an amino acid sequence selected from the group consisting of SEQ ID NO: 1, SEQ ID NO: 2, a polypeptide having at least 85% identity to SEQ ID NO: 1, and a polypeptide having at least 85% identity to SEQ ID NO: 2.

In some aspects, the present disclosure provides a method for determining the risk of neurodegeneration in a subject, comprising: (a) determining secreted soluble ST2 (sST2) level in a biological sample taken from the subject; (b) comparing the sST2 level with a standard control; and (c) determining the subject to have an increased risk of neurodegeneration when the sST2 level obtained in step (a) is greater than the standard control. In some embodiments, the biological sample is a blood, serum, plasma, or cerebral spinal fluid (CSF) sample. In some embodiments, step (a) comprises an immunological assay using an antibody against sST2.

In some aspects, the present disclosure provides a method for identifying a modulator of neurodegeneration, comprising: (a) contacting a candidate agent with IL-33 and full-length ST2 (ST2L) or sST2 under conditions permissible for IL-33/ST2L binding or IL-33/sST2 binding; (b) detecting IL-33/ST2L or IL-33/sST2 binding level; and (c) identifying the candidate agent as a modulator of neurodegeneration when the IL-33/ST2L or IL-33/sST2 binding level obtained in step (b) is more or less than the IL-33/ST2L or IL-33/sST2 binding level under the same conditions but in the absence of the candidate agent. In some embodiments, step (a) comprises an in vitro protein binding assay. In some embodiments, step (a) comprises a protein binding assay on the surface of a cell expressing ST2L.

In some aspects, the present disclosure provides a medicament for treating or inhibiting neurodegeneration in a subject, comprising: an effective amount of IL-33 and a pharmaceutically acceptable excipient.

In some embodiments, the medicament further comprises one or more additional therapeutically active agents. In some embodiments, the one or more additional therapeutically active agents is selected from the group consisting of donepezil, rivastigmine, galantamine, memantine, aducanumab, rosiglitazone, bexarotene, losartan, and rhynchophylline.

In some embodiments, the medicament is formulated for subcutaneous, transdermal, intradermal, transmucosal, intramuscular, intravenous, intraperitoneal, intracranial, intracerebroventricular, intrathecal, topical, or oral administration. In some embodiments, the medicament is formulated for subcutaneous administration.

In some aspects, the present disclosure provides a kit for determining risk of neurodegeneration in a subject, comprising (1) an agent for determining sST2 level in a biological sample taken from the subject; and (2) a standard control indicating sST2 level in the same type of biological sample taken from a subject not suffering from and not at risk of suffering from neurodegeneration. In some embodiments, the biological sample is a blood, serum, plasma, or CSF sample. In some embodiments, the agent is an antibody specific for sST2. In some embodiments, the kit further comprises an instruction manual for determining risk of neurodegeneration.

In some aspects, the present disclosure provides a method for detecting secreted soluble ST2 (sST2) in a subject, comprising: (a) detecting an sST2 level in a biological sample taken from the subject by contacting the sample with an anti-ST2 antibody and detecting binding between the sST2 and the antibody; and (b) comparing the sST2 level with a standard control. In some embodiments, the biological sample is a blood, serum, plasma, or cerebral spinal fluid (CSF) sample. In some embodiments, step (a) comprises an immunological assay using an antibody against sST2.

In some aspects, the present disclosure provides a method for increasing the transcription of an Aβ receptor in a subject in need thereof, comprising administering to the subject an effective amount of a composition comprising IL-33. In some embodiments, the Aβ receptor comprises a receptor selected from the group consisting of Toll like receptor 2 (TLR2), low density lipoprotein receptor (LDLR), and macrophage scavenger receptor 1 (MSR1). In some embodiments, the subject suffers from or is at risk of suffering from Alzheimer's disease, mild cognitive impairment, Parkinson's disease, or multiple sclerosis. In some embodiments, the composition is administered subcutaneously, intraperitoneally, intravenously, intradermally, intracerebroventricularly, intrathecally, orally, by inhalation, transdermally, or transmucosally.

In some embodiments, the composition is co-administered with one or more additional therapeutically active agents. In some embodiments, the one or more additional therapeutically active agents is selected from the group consisting of donepezil, rivastigmine, galantamine, memantine, aducanumab, rosiglitazone, bexarotene, losartan, and rhynchophylline.

In some embodiments, the IL-33 is a recombinant IL-33 protein. In some embodiments, the IL-33 recombinant protein comprises an amino acid sequence selected from the group consisting of SEQ ID NO: 1, SEQ ID NO: 2, a polypeptide having at least 85% identity to SEQ ID NO: 1, and a polypeptide having at least 85% identity to SEQ ID NO: 2.

In some aspects, the present disclosure provides a method for determining the risk of neurodegeneration in a subject, comprising: (a) determining secreted soluble ST2 (sST2) level in a biological sample taken from the subject; (b) comparing the sST2 level with a standard control; (c) determining the subject to have an increased risk of neurodegeneration when the sST2 level obtained in step (a) is greater than the standard control; (d) determining the genetic variants of ST2 and combine the data with the sST2 levels in a biological sample taken from the subject; (e) comparing the sST2 level with the standard controls within the cohort; and (f) determining the subject to have an increased risk of neurodegeneration when the sST2 level obtained in step (d) is greater than the standard control.

BRIEF DESCRIPTION OF THE DRAWINGS

FIG. 1A shows averaged slopes of baseline-normalized field excitatory postsynaptic potential (fEPSP; mean±SEM). Trace recordings 5 min before (1) and 55 min after (2) LTP induction (arrow) are shown. Inset traces are examples of fEPSPs recorded before (gray) and after (black) high-frequency stimulation (HFS). FIG. 1B shows quantification of mean fEPSP slopes during the last 10 min of the recording after LTP induction. WT, control (Con)=8 brains, 16 slices; WT, IL-33=8 brains, 17 slices; APP/PS1, Con=8 brains, 18 slices; APP/PS1, IL-33=8 brains, 18 slices. *** $p<0.001$, two-way ANOVA followed by the Bonferroni post hoc test.

FIG. 2A is a schematic diagram showing the timeline of IL-33 administration (i.p.) and behavioral experiments including the open field (OF) and nest building (NB) tests. FIG. 2B shows that IL-33-treated APP/PS1 mice (~14 months old) showed improved habituation in the OF test. Mice administered IL-33 or control vehicle (Con) were allowed to explore a novel arena scheduled as in FIG. 2A; each training session lasted 15 minutes. FIG. 2B shows the total distance traveled within each training session. n=7 mice per experimental group except n=6 mice for Con in APP/PS1. *$p<0.05$ at day 3, two-way repeated-measures ANOVA followed by the Bonferroni post hoc. FIG. 2C shows that IL-33-treated APP/PS1 mice exhibited better nest-building performance than Con APP/PS1 mice. Nest-building activity was assessed and scored. n=4.

FIG. 3A are representative images of DAB staining of amyloid plaque deposition in sST2 infused APP/PS1 mice after administration with IL-33 (i.p.) for 2 days (at 10 months old). Aβ deposition in the cortex of APP/PS1 mice after IL-33 or DPBS (Con) injection were immunostained by anti-Aβ antibody (4G8) using DAB kit. Scale bar=250 µm. FIG. 3B shows the quantification of the number of plaques in the cortex. Data are presented as mean±SEM (n=6 mice/condition; *p<0.05, Student's t-test).

FIG. 5A displays representative projected confocal images showing Aβ, Iba1, and Hoechst labeling in the cortex of control vehicle (Con) or IL-33-treated APP/PS1 mice. FIG. 5B displays a three-dimensional reconstruction using Imaris image analysis software showing the detailed interaction between Aβ plaques and microglia. A colocalization channel (shown in white) was built, from where the Aβ plaque and microglia (Iba1) volumes colocalized in each confocal stack. FIG. 5C shows a quantification of the estimated percentage of the Aβ plaque volume colocalized with microglia. The total volume of the colocalization channel was divided by that of the Aβ plaques in each confocal stack. n=16 images taken in the cortex of 4 individual mice in each condition; p<0.001, Student's t-test. Scale bars=10 µm.

FIG. 8A displays representative blots showing NEP and insulin-degrading enzyme (IDE) expression. APP and actin indicate mouse genotyping and equal loading, respectively. FIG. 8B shows a quantitative analysis of NEP expression and FIG. 8C shows a quantitative analysis of IDE expression (fold change vs. WT, Con). n=4 brains, **p<0.01, one-way ANOVA followed by the Bonferroni post hoc.

FIGS. 10A-10C show that IL-33 alters microglial transcriptome signature in APP/PS1 mice. FIG. 10A showing a heatmap plot of 2007 genes (showing p<0.05 in one-way ANOVA) is subgrouped by the K-means clustering method against the normalized FPKM value. The expression levels of individual genes in different samples were normalized according to a mean of 0 and standard deviation of 1 within the range [−2, +2]; levels above and below the mean are shown in yellow and blue, respectively. Different clusters of genes were obtained from the K-means clustering method against the normalized expression levels and indicated by labels C1-C6 or sidebars with different colors. Enriched gene ontology terms suggested by the DAVID database in each cluster are listed (Benjamini-Hochberg adjusted p<0.05). FIG. 10B displays transcriptome signatures representing patterns of normalized gene expression levels in different clusters indicated by corresponding colors, with the labeling of gene number in each cluster. FIG. 10C provides a list of representative genes in APP/PS1 mice administered control vehicle (Con) or IL-33 with upregulated gene cluster, C4, C5 and C6. Corresponding networks of upregulated genes in each gene set are classified according to the STRING database (FIGS. 10D-10O). The top six networks in response to IL-33 in microglia of APP/PS1 mice are shown: cholesterol homeostasis (FIGS. 10D, 10G), IL-6/JAK/STAT3 signaling (FIGS. 10E, 10H), IFN-α response (FIGS. 10F, 10I); IFN-γ response (FIGS. 10J, 10M); G2M phase of the cell cycle (FIGS. 10K, 10N); and TNF-α response (FIGS. 10L, 10O). Upper panels (FIGS. 10D, 10E, 10F, 10J, 10K, 10L) show gene sets of APP/PS1 mice regulated by IL-33 suggested by GSEA. Lower panels (FIGS. 10G, 10H, 10I, 10M, 10N, 10O) show STRING networks where the nodes represent genes, and edges suggest connections between genes. Larger nodes indicate more connected edges, and edges with darker colors indicate a stronger association between nodes. The fold changes of genes after IL-33 treatment were calculated in the log 2 range from [−1.5 to +1.5]; corresponding colors on each node indicate the values displayed in blue and red. FIGS. 10P-10R show that IL-33 increases the transcription of Aβ receptors, Toll like receptor 2 (FIG. 10P, TLR2), low density lipoprotein receptor (FIG. 10Q, LDLR), and macrophage scavenger receptor 1 (FIG. 10R, MSR1) in microglia of APP/PS1 mice. n=2.

FIGS. 14A-14D show that IL-33 treatment reverses contextual memory deficits in APP-PS1 mice. FIG. 14A shows a timeline of IL-33 administration (i.p.) and contextual fear conditioning (FC) test. S, electrical shock; T, freezing tests. FIG. 14B shows the percentage of freezing time immediately after the electric shock of the FC test. FIG. 14C shows the percentage of freezing time 1 day after administration of electric shock. FIG. 14D shows the percentage of freezing after 7 days after administration of electric shock. Data are mean±SEM. n=11-13 mice/group. *p<0.05; **p<0.01, two-way ANOVA with Bonferroni post hoc test.

FIG. 15A shows representative images and FIG. 15B shows quantification of 4G8-stained amyloid plaques in the cortices of APP/PS1 mice (12-months-old) after IL-33 administration (i.p.) with or without sST2 infusion. n=7 mice/group. *p<0.05, one-way ANOVA and Bonferroni post hoc test. All data are mean±SEM. (Scale bars: Top, 500 µm; Bottom, 100 µm).

FIGS. 16A-16B show that IL-33 increases CD68 expression in Aβ plaques. APP/PS1 mice were treated with IL-33 via i.p. injection for 2 days. Representative projected confocal images show the distribution of CD68$^+$ Iba1$^+$ cells around the Aβ plaques in the cortices of vehicle-treated (Con; FIG. 16A) or IL-33-treated (FIG. 16B) APP/PS1 mice.

FIGS. 17A-17B show that IL-33 drives microglia to an alternative activation state in APP/PS1 mice. APP/PS1 mice were i.p. injected with IL-33 for 2 days. Shown is quantitative ddPCR analysis of Fizz1 (FIG. 17A) and arginase 1 (Arg1, FIG. 17B) mRNA levels in microglia isolated from IL-33-administered APP/PS1 mouse brains. WT/Con, n=5 mice; WT/IL-33, n=4 mice; APP/PS1/Con, n=7 mice; APP/PS1/IL-33, n=6 mice. *p<0.05; **p<0.01, two-way ANOVA with Bonferroni post hoc test.

FIG. 20 shows that IL-33 does not affect the plasma histamine level in wild-type or APP/PS1 mice. Wild-type (WT) and APP/PS1 mice (8-months-old) were i.p. injected with IL-33 (200 ng) or vehicle control (Con, DPBS) for 2 days. Plasma histamine levels were determined by ELISA. n=4 mice per group. Data are mean±SEM. Similar results were obtained for WT BALB/c mice (data not shown).

FIG. 21 shows that IL-33 reduces the soluble Aβ content in APP/PS1 mice. APP/PS1 mice (25-months-old) were i.p. injected with IL-33 (200 ng) 3 times for 7 days. FIG. 21 is a representative Western blot of soluble and insoluble Aβ in cortical homogenates of APP/PS1 mice. Each lane represents an individual APP/PS1 mouse. Con, n=2 mice; IL-33, n=3 mice.

FIGS. 22A-22B show that IL-33 reduces the 4G8-stained Aβ plaques in the cortices of 5XFAD mice. 5XFAD mice (10-months-old) were administered (i.p.) with IL-33 (200 ng) or DPBS control (Con) for two consecutive days. Representative images (FIG. 22A) and quantification (FIG. 22B) of 4G8 antibody-stained Aβ plaques in the cortices. Data are mean±SEM. Con, n=6; IL-33, n=5. (**p<0.01; Student's t-test). Scale bar=500 µm.

FIGS. 24A-24D show distributions of CD11b$^+$CD45$^{lo}$ and CD11b$^+$CD45$^{hi}$ cell populations. Representative contour plots showing distribution of CD11b$^+$CD45$^{lo}$ and CD11b$^+$CD45$^{hi}$ cell populations in WT mice (FIG. 24A), APP/PS1 mice administered with DPBS (FIG. 24B), or APP/PS1 mice injected with IL-33 (FIG. 24C). FIG. 24D shows the quantification of CD45$^{hi}$ cells in the population of CD11b$^+$ cells of APP/PS1 mice administered with IL-33 or Con. APP/PS1/Con, n=5 mice; APP/PS1/IL-33, n=6 mice. All data are mean±SEM. (ns=not statistically significant; Student's t-test).

FIG. 25A displays fluorescent images showing the phagocytic activity of CD11b$^+$ myeloid cells. Scale bar=50 µm. The boundaries of CD11b$^+$ myeloid cells were determined by Iba1 labeling intensity and the amount of phagocytosed fluorescein-Aβ estimated for each Iba1$^+$ cell (FIG. 25B). FIG. 25C shows the quantification of phagocytosis. Results are the fold change of the area of fluorescein-Aβ phagocytosed into the cells over the total cell area and the data were normalized to the control. n=75-490 cells from 3 independent experiments. p<0.01; *p<0.001; one-way ANOVA with Bonferroni post hoc test.

FIGS. 26A-26D show IL-33/ST2 signaling in microglia. ST2 levels in the brain myeloid cells remain relatively unchanged in WT and APP/PS1 mice during aging (FIG. 26A). CD11b$^+$ myeloid cells were isolated from WT and APP/PS1 mouse brains. Quantitative real-time RT-PCR analysis for ST2 was performed and normalized to CD11b transcripts. 5-month-old: WT, n=4 mice; APP/PS1, n=4 mice; 9-month-old: WT, n=3 mice; APP/PS1, n=3 mice. FIGS. 26B-26D show that IL-33 stimulates activation of p38 and ERK1/2 in primary CD11b$^+$ myeloid cells. CD11b$^+$ myeloid cells from adult C57BL/6 mice were cultured for 7 days in vitro and then treated with IL-33 (100 ng/mL) for the indicated times. Representative Western blot (FIG. 26B) and fold change of phosphorylated p38 (FIG. 26C) and phosphorylated ERK1/2 (FIG. 26D) normalized to their total proteins. n=3-4 experiments. *p<0.05; **p<0.01 compared to 0 min; one-way ANOVA with Bonferroni post hoc test.

FIG. 27A Box plot showing the soluble ST2 (sST2) levels in the serum of healthy subjects (NC, n=17) and patients with mild cognitive impairment (MCI, n=18). (*p<0.05; two-sample t-test). FIG. 27B is a table showing the demographic characteristics of the human subjects for serum sST2 determination. Summary statistics are presented as mean [min–max] or count (%). NC=healthy control; MCI=mild cognitive impairment.

FIGS. 28A-28B show that subcutaneous (s.c.) administration of IL-33 reduced soluble Aβ levels in the brain cortices of APP/PS1 mice. Representative Western blots of soluble and insoluble Aβ in cortical homogenates of APP/PS1 mice with s.c. injection (FIG. 28A) and i.p. injection (FIG. 28B) are shown.

(FIGS. 29A-29B) administered IL-33 together with vehicle control (Con) for two consecutive days. LTP in the hippocampal CA1 region was induced by HFS. FIG. 29A shows averaged slopes of baseline normalized field excitatory postsynaptic potential (fEPSP; mean±SEM). FIG. 29B shows the quantification of mean fEPSP slopes during the last 10 minutes of the recording after LTP induction; n=4 brain slices from 2 mice. (**p<0.01; two-way ANOVA with Bonferroni post hoc test).

FIGS. 32A-32B show that long-term IL-33 administration (i.p.) ameliorated AP plaques in APP/PS1 mice. Representative images (FIG. 32A) and quantification (FIG. 32B) of 4G8-stained amyloid plaques in the cortices of APP/PS1 mice after IL-33 administration.

FIGS. 33A-33C show that long-term IL-33 treatment (i.p.) modulated inflammatory responses in APP/PS1 mice. IL-33 suppressed the expression of several inflammatory genes in the cortices of APP/PS1 mice. Quantitative real-time RT-PCR analysis of SPP1 (FIG. 33A), CD11c (FIG. 33B), and Lilrb4 (FIG. 33C) was performed and normalized to β-actin transcripts. (*p<0.05; p<0.01; *p<0.001; two-way ANOVA with Bonferroni post hoc test). All data are mean±SEM.

FIG. 34A shows the averaged slopes of baseline normalized fEPSP (mean±SEM). FIG. 34B shows the quantification of mean fEPSP slopes during the last 10 minutes of the recording after LTP induction; n=3-4 slices from 2 mice. (*p<0.05; two-way ANOVA with Bonferroni post hoc test).

FIG. 35A shows averaged slopes of baseline-normalized field excitatory postsynaptic potential (fEPSP; mean±SEM). FIG. 35B shows quantification of mean fEPSP slopes during the last 10 min of the recording after LTP induction. (Con: 4 brains, 6 slices; Con+Aβ: 4 brains, 8 slices; IL-33+Aβ: 4 brains, 8 slices; Mem+Aβ: 3 brains, 6 slices; IL-33+Mem+Aβ: 5 brains, 10 slices; *p<0.05, p<0.01, *p<0.001, one-way ANOVA followed by the Bonferroni post hoc test).

DETAILED DESCRIPTION

I. Introduction

Figure 1A:
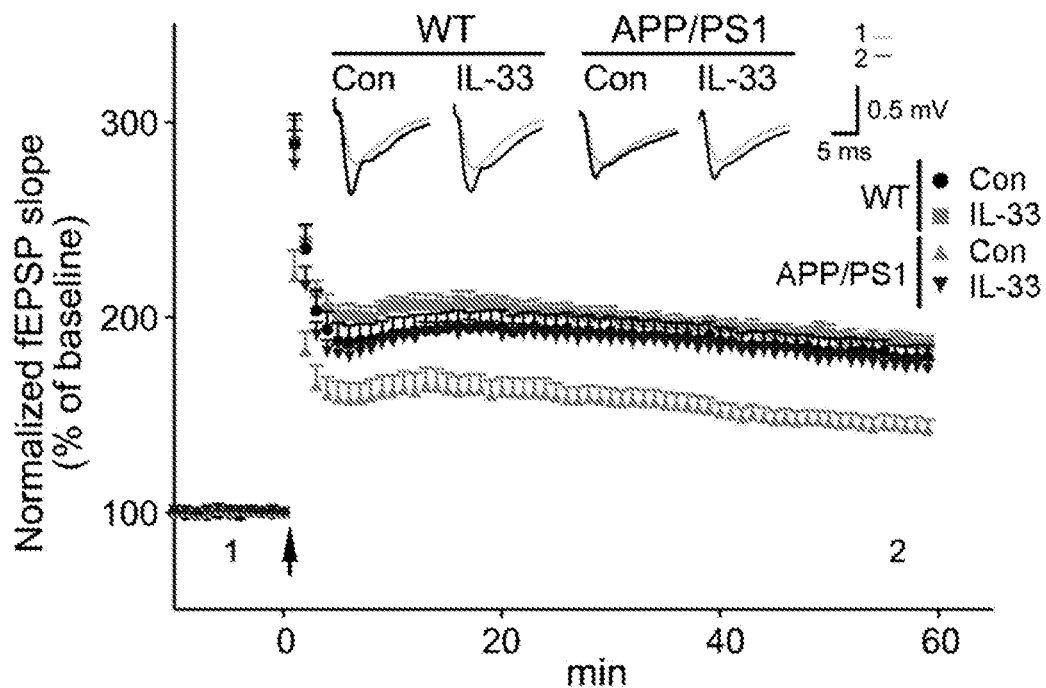
FIGS. 1A-1B show that IL-33 rescues the LTP impairment in APP/PS1 mutant mice. WT and APP/PS1 mice at ~7.5 months of age were administered mouse IL-33 (IL-33; 200 ng) or control vehicle (Con) via intraperitoneal injection (i.p.) for 2 days.

The present technology relates to the discovery that IL-33 is a neuroprotective agent effective for treating neurodegenerative and neuroinflammatory disorders or for reducing one's risk of developing such disorders. In some embodiments, the present technology provides methods and compositions useful for treating or inhibiting neurodegenerative and neuroinflammatory disorders utilizing this newly revealed property of IL-33. In some embodiments, therapeutic compositions of the present technology comprise IL-33, optionally in combination with one or more additional pharmaceutically active ingredients, for effective treatment of neurodegenerative and neuroinflammatory disorders such as Alzheimer's disease (AD), Parkinson's disease (PD), or mild cognitive impairment (MCI).

The present technology also relates to the discovery that elevated levels of a soluble form of IL-33 receptor, sST2, correlates to the presence of neurodegenerative and neuroinflammatory disorders, for example, MCI or AD. Thus, in some embodiments, the present technology provides a novel, previously undisclosed diagnostic method for early detection or risk assessment of neurodegenerative and neuroinflammatory disorders such as MCI or AD.

In some embodiments, modulators of a neurodegenerative and neuro-inflammatory disorder via modulating IL-33 and ST2 interaction can be identified first in a protein binding assay and then verified by additional testing such as in an animal model for the neurodegenerative and neuro-inflammatory disorder. Modulators, especially small molecules that have been identified regulate IL-33/ST2 binding levels, represent new potentially effective therapeutics in the treatment of neurodegenerative and neuroinflammatory disorders.

Thus, in some embodiments, the present technology provides a method for treating or reducing risk of neurodegeneration or neuroinflammation in a subject. The method comprises the step of administering to the subject an effective amount of IL-33. In some embodiments, the present disclosure includes a method for increasing the expression of Aβ receptors in a subject in need thereof relative to a control, comprising administering an effective amount of IL-33. In some embodiments, the present disclosure provides a method for increasing the expression of an Aβ receptor selected from the group consisting of Toll like receptor 2 (TLR2), low density lipoprotein receptor (LDLR), and macrophage scavenger receptor 1 (MSR1), comprising administering an effective amount of IL-33. In some embodiments, the subject suffers from or is at risk of suffering from Alzheimer's disease (AD), mild cognitive impairment (MCI), Parkinson's disease (PD), or multiple sclerosis (MS). In some embodiments, the IL-33 used in the method may be an IL-33 protein (e.g., a recombinantly produced IL-33 protein) or a nucleic acid encoding an IL-33 protein. In some embodiments, the administration comprises intraperitoneal (i.p.) administration of IL-33, such as i.p. administration for a time period of 1 day, 2 days, 3 days, 4 days, 5 days, 1 week, 10 days, or up to 2 weeks. In some embodiments, the IL-33 administration period is 2 days.

In some embodiments, the administration comprises co-administration of IL-33 and a second therapeutically active agent. For example, the second therapeutically active agent is donepezil, rivastigmine, galantamine, memantine, aducanumab, rosiglitazone, bexarotene, losartan, or rhynchophylline. In some embodiments, the amount of the second active agent being administered may range from 0.1-1000 mg/day, 1-500 mg/day, 1-100 mg/day, 2-50 mg/day, or 5-20 mg/day, such as 10, 15, or 20 mg/day. The amount of IL-33 protein being administered, either alone or together with a second therapeutically active agent, may range from 0.01-3000 mg/day, 0.1-500 mg/day, 0.1-300 mg/day, 0.2-100 mg/day, 0.5-100 mg/day, 2-100 mg/day, 5-50 mg/day, or 10, 15, 20, 25, 30, and 50 mg/day.

In some embodiments, any conventional methods or agents known for their effectiveness in treating neurodegeneration or neuroinflammation are used in combination with IL-33 in the practice of the present technology. For example, in some embodiments, an anti-epileptic agent is administered in combination with IL-33 (see, e.g., Sanchez et al., *Proc Natl Acad Sci USA*. 2012 Oct. 16; 109(42):E2895-903. doi: 10.1073/pnas.1121081109. Epub 2012 Aug. 6). Also, in some embodiments, an antibody against EphA4, such as those described in U.S. Provisional Patent Application No. 62/031,793, is administered in combination with IL-33. In some embodiments, a known therapy such as a computer-based cognitive training method (see, e.g., Hofmann et al., *J Psychiatr Res*. 1996 November-December; 30(6):493-501) is used in combination with the administration of IL-33.

In some embodiments, the present technology provides a method for determining a subject's risk of neurodegenerative or neuroinflammatory conditions such as Alzheimer's disease or mild cognitive impairment. In some embodiments, the method comprises: (a) determining secreted soluble ST2 (sST2) level in a biological sample taken from the subject; (b) comparing the sST2 level with a standard control; and (c) determining the subject to have an increased risk of neurodegeneration when the sST2 level obtained in step (a) is greater than the standard control. In some embodiments, the biological sample is a blood, serum, plasma, or cerebral spinal fluid (CSF) sample. In some embodiments, step (a) comprises an immunological assay using an antibody against sST2. In some embodiments, when a patient is determined as having a neurodegenerative or neuroinflammatory disorder such as Alzheimer's disease or mild cognitive impairment or as having an increased risk of developing the disorder at a later time, the patient may receive medical intervention as deemed appropriate by a physician. In some embodiments, the medical intervention is therapeutic or prophylactic in nature and involves any currently available methods and active agents approved for treating the disorder. In addition, in some embodiments, long-term patient monitoring for disease progression is appropriate for patients who have received a positive diagnosis of presence of a neurodegenerative or neuroinflammatory disorder or an increased risk of developing one.

In some embodiments, the present technology provides a method for identifying a modulator of neurodegeneration or neuroinflammation. The method comprises: (a) contacting a candidate agent with IL-33 and full-length ST2 (ST2L) or sST2 under conditions permissible for IL-33/ST2L binding or IL-33/sST2 binding; (b) detecting IL-33/ST2L or IL-33/sST2 binding level; and (c) identifying the candidate agent as a modulator of neurodegeneration when the IL-33/ST2L or IL-33/sST2 binding level obtained in step (b) is more or less than the IL-33/ST2L or IL-33/sST2 binding level under the same conditions but in the absence of the candidate agent. In some embodiments, step (a) comprises an in vitro protein binding assay. In some embodiments, step (a) comprises a protein binding assay on the surface of a cell expressing ST2L. Optionally, in some embodiments, additional steps are taken to further verify the activity of the modulator identified by the method, for example, in an animal experiment described herein.

In some embodiments, the present technology provides a medicament for treating or inhibiting neurodegeneration or neuroinflammation in a subject. In some embodiments, the medicament comprises: (1) an effective amount of IL-33 and (2) a pharmaceutically acceptable excipient. In some embodiments, the IL-33 is an IL-33 protein. In some embodiments, the IL-33 is a nucleic acid encoding an IL-33 protein, such as an expression cassette comprising an IL-33 coding sequence. In some embodiments, the medicament includes a second therapeutically active agent, such as donepezil, rivastigmine, galantamine, memantine, aducanumab, rosiglitazone, bexarotene, losartan, or rhynchophylline. In some embodiments, other therapeutically active agents known to be useful for treating neurodegeneration or neuroinflammation are included in the medicament: for example, an anti-epileptic agent or an antibody against EphA4. In some embodiments, the medicament is formulated for parenteral (e.g., intravenous, intradermal, intraperitoneal, or subcutaneous), intracranial, intracerebroventricular, intrathecal, oral, respiratory (e.g., by inhalation), transdermal (topical), and transmucosal administration. In some embodiments, the medicament is formulated for intraperitoneal administration. In some embodiments, the medicament is formulated for subcutaneous administration. In some embodiments, the medicament is formulated for intrathecal administration. In some embodiments, the medicaments of the present technology are in the form of an aqueous solution or in a lyophilized form.

In some embodiments, the present technology provides a kit for determining risk of neurodegeneration or neuroinflammation in a subject. The kit comprises: (1) an agent for determining sST2 level in a biological sample taken from the subject; and (2) a standard control indicating sST2 level in the same type of biological sample taken from a subject not suffering from and not at risk of suffering from neurodegeneration or neuroinflammation. Typically, these components are kept in separate containers of the kit. In some embodiments, the biological sample is a blood, serum, plasma, or CSF sample. In some embodiments, the agent is an antibody specific for sST2, which in some embodiments also specifically recognizes ST2L while in other embodiments does not specifically recognize ST2L. In some embodiments, the kit further comprises an instruction manual for determining risk of neurodegeneration or neuroinflammation.

The disclosure of the present technology relates to compositions and methods for preventing and treating neurodegenerative and neuroinflammatory diseases. Compositions comprise IL-33, optionally in combination with one or more of a variety of therapeutic active compounds, including a pharmaceutically acceptable salt thereof, and one or more excipients are provided for the treatment of neurodegenerative and neuroinflammatory conditions. Methods of administering the compositions are also provided.

The disclosure of the present technology also relates to the use of soluble ST2 (sST2) protein as a biomarker for neurodegenerative diseases such as mild cognitive impairment (MCI), early Alzheimer's disease (AD), as well as other neuroinflammatory-related neurodegeneration, and discloses methods to diagnose human subjects with these conditions, assess risk of developing these conditions, or assess therapeutic effectiveness in patients in response to treatment of these conditions. The disclosure of the present technology also relates to methods of treating neurodegenerative or neuroinflammatory conditions in human subjects, by manipulating/activating the ST2 pathway; by regulating transcription and expression of ST2 and IL-33; or by modulating the IL-33 and ST2 interaction.

Thus, the present technology represents new preventative and therapeutic interventions for various neurodegenerative and neuroinflammatory conditions including dementia, mild cognitive impairment (MCI), Alzheimer's disease (AD), Parkinson's disease (PD), multiple sclerosis (MS), depression, stroke, dementia with Lewy bodies, amyotrophic lateral sclerosis, frontotemporal dementia, Huntington's disease (HD), retinal degenerative diseases such as glaucoma age-related macular degeneration and diabetic retinopathy, hearing loss due to nerve degeneration, traumatic brain injury, and spinal cord injury, and other neuroinflammatory conditions such as acute disseminated encephalomyelitis, optic neuritis transverse myelitis post-polio syndrome, multifocal motor neuropathy, and chronic inflammatory demyelinating polyneuropathy.

II. Definitions

The term "treat" or "treating," as used in this application, describes an act that leads to the elimination, reduction, alleviation, reversal, prevention and/or delay of onset or recurrence of any symptom of a predetermined medical condition. In other words, "treating" a condition encompasses both therapeutic intervention and prophylactic intervention against worsening of the condition. A subject is successfully treated for a particular condition where after receiving an effective amount of a therapeutic agent the subject shows observable and/or measurable reduction in or absence of one or more signs and symptoms of the condition. In some embodiments, a subject is successfully treated for a neurodegenerative or neuroinflammatory condition where, after receiving an effective amount of IL-33 according to the methods described herein, the subject shows observable and/or measurable reduction in or absence of one or more signs and symptoms of the neurodegenerative or neuroinflammatory condition.

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "standard control," as used herein, refers to a sample comprising an analyte of a predetermined amount to indicate the quantity or concentration of this analyte present in this type of sample taken from an average healthy subject not suffering from or at risk of developing a predetermined disease or condition (e.g., a neurodegenerative or neuroinflammatory condition such as Alzheimer's disease or mild cognitive impairment).

The term "average," as used in the context of describing a healthy subject who does not suffer from and is not at risk of developing any neurodegenerative disorders, refers to certain characteristics, such as the level of sST2 in the person's blood, that are representative of a randomly selected group of healthy humans who are not suffering from and is not at risk of developing any neurodegenerative or neuroinflammatory conditions. This selected group should comprise a sufficient number of human subjects such that the average amount or concentration of the analyte of interest among these individuals reflects, with reasonable accuracy, the corresponding profile in the general population of healthy people. Optionally, the selected group of subjects may be chosen to have a similar background to that of a person who is tested for indication or risk of a neurodegenerative or neuroinflammatory disorder, for example, matching or comparable age, gender, ethnicity, and medical history, etc.

The term "inhibiting" or "inhibition," as used herein, refers to any detectable negative effect on a target biological process. Typically, an inhibition is reflected in a decrease of at least 10%, 20%, 30%, 40%, or 50% in one or more parameters indicative of the biological process or its downstream effect, when compared to a control where no such inhibition is present. The term "enhancing" or "enhancement" is defined in a similar manner, except for indicating a positive effect, i.e., the positive change is at least 10%, 20%, 30%, 40%, 50%, 80%, 100%, 200%, 300% or even more in comparison with a control. The terms "inhibitor" and "enhancer" are used to describe an agent that exhibits inhibiting or enhancing effects as described above, respectively. Also used in a similar fashion in this disclosure are the terms "increase," "decrease," "more," and "less," which are meant to indicate positive changes in one or more predetermined parameters by at least 10%, 20%, 30%, 40%, 50%, 80%, 100%, 200%, 300% or even more, or negative changes of at least 10%, 20%, 30%, 40%, 50%, 80% or even more in one or more predetermined parameters.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed (e.g., one encoding IL-33), operably linked to a promoter.

As used herein, "IL-33" refers to a protein having an amino acid sequence as set forth in SEQ ID NOs: 1-4, or functional fragments or variants thereof, or a nucleic acid sequence encoding the same. In some embodiments of the present technology, IL-33 comprises SEQ ID NO: 1, 2, 3, or 4. In some embodiments of the present technology, IL-33 comprises a full-length IL-33 corresponding to the amino acid sequence set forth in SEQ ID NO: 1 or 3. In some embodiments of the present technology, IL-33 comprises a functional fragment of SEQ ID NO: 1, 2, 3, or 4. In some embodiments of the present technology, IL-33 comprises a functional C-terminal fragment corresponding to the amino acid sequence set forth in SEQ ID NO: 2 or 4. In some embodiments of the present technology, IL-33 comprises a variant of SEQ ID NO: 1, 2, 3, or 4. In some embodiments of the present technology, the full-length, functional fragment, or variant of IL-33 is recombinantly produced.

III. General Description of the Present Technology

The disclosure of the present technology relates to compositions and methods for preventing and treating neurodegenerative and neuroinflammatory diseases. The active ingredient in the composition is IL-33. Compositions of the present technology may include one or more therapeutically active agents in addition to IL-33. For example, the compositions may comprise the following combinations: a combination of IL-33 and an acetylcholinesterase inhibitor, such as donepezil, rivastigmine, or galantamine; a combination that includes IL-33 and an N-Methyl-D-Aspartate receptor (NMDAR) antagonist, such as memantine; a combination that includes IL-33 and aducanumab; a combination that includes IL-33 and a heterodimer of different chemical moieties, see, e.g., U.S. Pat. No. 7,605,265; a combination that includes IL-33 and rosiglitazone; a combination that includes IL-33 and bexarotene, a combination that includes IL-33 and an angiotensin 2 receptor blocker, such as losartan; a combination that includes IL-33 and DA001 or its derivatives, see, e.g., U.S. Pat. No. 8,642,567 and U.S. Pat. No. 9,029,414; a combination that includes IL-33 and a natural product extract or compound, such as rhynchophylline; a combination that includes IL-33 and small molecule Rhy derivatives, such as Rhy-37, see, e.g., PCT/CN2014/082386. An effective amount of the active ingredient(s) together with a pharmaceutically acceptable salt, and one or more excipients, can be administered to human subjects for the treatment or prevention of a neurodegenerative or neuroinflammatory disease/disorder. An effective amount of the active ingredient(s) together with a pharmaceutically acceptable salt, and one or more excipients, can also be administered to human subjects in a method for increasing the expression of Aβ receptors. In some embodiments, the Aβ receptor comprises a receptor selected from the group consisting of Toll like receptor 2 (TLR2), low density lipoprotein receptor (LDLR), and macrophage scavenger receptor 1 (MSR1). Suitable conditions for such treatment or prevention include MCI and early AD, AD, PD, MS, depression, stroke, dementia with Lewy bodies, amyotrophic lateral sclerosis, frontotemporal dementia, Huntington's disease, retinal degenerative diseases such as glaucoma age-related macular degeneration and diabetic retinopathy, hearing loss due to nerve degeneration, traumatic brain injury, and spinal cord injury, and other neuro-inflammatory conditions such as acute disseminated encephalomyelitis, optic neuritis transverse myelitis post-polio syndrome, multifocal motor neuropathy, and chronic inflammatory demyelinating polyneuropathy.

IL-33 promotes Th2-type immune response through signaling through its receptor ST2. The soluble ST2 acts as a decoy receptor. It binds IL-33 and makes it unavailable to the ST2 receptor, thus obstructing the downstream events of this receptor/ligand interaction. Here, the inventors have identified a previously undisclosed correlation between levels of sST2 in blood plasma of human subjects and the occurrence of mild cognitive impairment (MCI), the prodromal stage of AD. Elevated levels indicate the presence or increase risk of a neurodegenerative and neuroinflammatory disease in the human subject, and identify sST2 is a reliable biomarker for neurodegenerative and neuroinflammatory diseases such as MCI. This is a breakthrough approach since there is currently no diagnostic tool for detection of MCI and early AD. Thus, the present technology discloses novel methods to diagnose (or detect an increased risk of developing) MCI and early AD in human subjects, and provides a kit that enables levels of sST2 in the blood plasma of human subjects to be measured. The kit may be formulated for subcutaneous, intramuscular, intravenous, intraperitoneal, topical, intranasal, or oral administration.

developing neurodegenerative or neuroinflammatory disorders such as Alzheimer's disease (AD), mild cognitive impairment (MCI), and Parkinson's disease (PD). Pharmaceutical or physiological compositions, suitable in both prophylactic and therapeutic applications, typically include the active component plus one or more pharmaceutically or physiologically acceptable excipients or carriers.

Compositions comprising IL-33 may be formulated for prophylactic and therapeutic purposes. IL-33 may be in the form of a protein, e.g., a recombinantly produced protein. Optionally, the protein may contain modifications such as substitution of naturally occurring amino acid residue(s) with one or more different amino acid(s) or one or more artificial amino acids, including D-amino acids.

An illustrative full-length human IL-33 (hIL-33) protein, given by UniProt Accession No. 095760 (SEQ ID NO. 1), is provided below. The underlined portion of the amino acid sequence set forth in SEQ ID NO: 1 (amino acids 112-270) represents a C-terminal fragment of hIL-33 and corresponds to SEQ ID NO: 2.

```
  1  mkpkmkystn kistakwknt askalcfklg ksqqkakevc pmyfmklrsg lmikkeacyf
 61  rrettkrpsl ktgrkhkrhl vlaacqqqst vecfafgisg vqkytralhd ssitqispit
121  eylaslstyn dqsitfaled esyeiyvedl kkdekkdkvl lsyyesqhps nesqdqvdqk
181  mlmvtlsptk dfwlhannke hsvelhkcek plpdqaffvl hnmhsncvsf ecktdpqvfi
241  qvkdnhlali kvdssenlct enilfklset
```

ST2 was previously known to play a role in the progression of cardiac disease, and sST2 levels were correlated with cardiovascular disease (CVD). Additionally, sST2 has been identified as a biomarker for CVD, for neurohormonal activation in patients with heart failure, and as an indicator of mortality in these patients. Thus, sST2 is postulated to An illustrative full-length mouse IL-33 (mIL-33) protein, given by UniProt Accession No. Q8BVZ5 (SEQ ID NO. 3), is provided below. The underlined portion of the amino acid sequence set forth in SEQ ID NO: 3 (amino acids 109-266) represents a C-terminal fragment of mIL-33 and corresponds to SEQ ID NO: 4.

```
  1  mrprmkysns kispakfsst agealvppck irrsqqktke fchvycmrlr sgltirkets
 61  yfrkeptkry slksgtkhee nfsayprdsr krsllgsiqa faasvdtlsi qqtslltqsp
121  aslstyndqs vsfvlengcy vinvddsgkd qeqdqvllry yespcpasqs gdgvdgkklm
181  vnmspikdtd iwlhandkdy svelqrqdvs ppeqaffvlh kkssdfvsfe cknlpqtyiq
241  vkdnglalve ekdescnnim fklski
``` have a role in CVD in the diagnostic and/or therapeutic context. Furthermore, the use of IL-33 in the treatment and diagnosis of cardiac diseases and disorders, such as cardiac hypertrophy, myocardial infarction, stroke, arteriosclerosis and heart failure has been described. Yet, the present inventors are the first to: (i) illustrate the correlation between elevated soluble sST2 levels and neurodegenerative and neuroinflammatory diseases such as mild cognitive impairment (MCI) and Alzheimer's disease (AD); (ii) disclose the method of measuring sST2 in blood plasma in a human subject; and (iii) disclose the method of manipulating pathways downstream of ST2/IL-33 signaling as a therapeutic strategy to treat neurodegenerative or neuroinflammatory conditions.

IV. Therapeutic Agents of the Present Technology

The present technology provides a variety of therapeutic agents that can be used for treating or reducing the risk of The homology between the human (hIL-33) and mouse (mIL-33) C-terminal fragments (SEQ ID NOs: 2 and 4, respectively) is 57%.

Peptides of the present disclosure may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.* 289, Academic Press, Inc, New York (1997).

In some embodiments, an IL-33 protein of the present technology is a protein comprising an amino acid sequence set forth in any one of SEQ ID NOs: 1-4, or a functional fragment or variant thereof. In some embodiments, IL-33 comprises a full-length IL-33 protein corresponding to the amino acid sequence set forth in SEQ ID NO: 1 or 3. In some embodiments, the IL-33 protein comprises a function fragment of SEQ ID NO: 1, 2, 3, or 4. In some embodiments, the IL-33 protein comprises a functional C-terminal fragment corresponding to the amino acid sequence set forth in SEQ ID NO: 2 or 4. In some embodiments, the IL-33 protein comprises a variant of the amino acid sequence set forth in any one of SEQ ID NOs: 1-4 having one or more conservative amino acid substitutions. In some embodiments, the variant has at least 99%, at least 95%, at least 85%, at least 80%, at least 75%, at least 70%, at least 65%, at least 60%, at least 55%, or at least 50% homology to an amino acid sequence set forth in any one of SEQ ID NOs: 1-4. In some embodiments of the present technology, the full-length, functional fragment, or variant of IL-33 is recombinantly produced.

Chemical modifications such as glycosylation, PEGylation, etc. are also possible, so long as the resultant IL-33 retains native IL-33's normal biological activities. IL-33 may be in the form of a nucleic acid encoding an IL-33 protein, for example, an expression cassette capable of directing the transcription of the IL-33 coding sequence and ultimately the translation of IL-33 protein. Optionally, IL-33 may be used in combination with a second or more active ingredients to enhance the desired therapeutic effects. Possible active ingredients include but are not limited to donepezil, rivastigmine, galantamine, memantine, aducanumab, rosiglitazone, bexarotene, losartan, and rhynchophylline, including a heterodimer of different chemical moieties named in, e.g., U.S. Pat. No. 7,605,265, DA001 or its derivatives named in, e.g., U.S. Pat. Nos. 8,642,567 and 9,029,414, as well as Rhy derivatives named in, e.g., PCT/CN2014/082386.

In addition, the present technology provides a method for identifying a modulator of a condition. In some embodiments, the present technology provides a method for identifying a modulator or a neurodegenerative or neuroinflammatory condition. This method is based on the discovery that interaction between IL-33 and its receptor ST2 is essential in IL-33 mediated neuroprotective effects. As such, the screening method includes these steps: (a) contacting a candidate agent with IL-33 protein and an ST2 protein (which may be sST2 or ST2L) under conditions permissible for IL-33/ST2 binding; (b) detecting IL-33/ST2 binding level; and (c) identifying the candidate agent as a modulator of neurodegeneration when the IL-33/ST2 binding level obtained in step (b) is more or less than the IL-33/ST2 binding level under the same conditions but in the absence of the candidate agent.

An in vitro assay can be used to screen for potential modulators of IL-33 signaling based on the effect of a candidate compound on the binding between IL-33 and ST2. In general, such an assay can be performed in the presence of IL-33 and an ST2 protein or a fragment thereof, for example, a recombinantly produced ST2L protein or sST2, under conditions permitting IL-33 binding to its receptor. In some cases, the binding assays can be performed in a cell-free environment; whereas in other cases, the binding assays can be performed within a cell or on the cell surface, for example, using cells recombinantly or endogenously expressing an appropriate ST2L polypeptide.

Once a compound is identified in the binding assay as a potential modulator of neurodegeneration, further testing may be conducted to confirm its activity. The screening method then can further comprise any necessary additional testing to determine whether the modulator promotes or inhibits neurodegeneration using methods and experimental models known in the field or as described in this application, e.g., in the examples.

A pharmaceutical composition made for the use in accordance with the present technology typically comprises one active agent (optionally with an additional active agent) as the therapeutically effective component and a pharmaceutically/physiologically acceptable excipient or carrier. Such composition may be specifically formulated for the intended route of administration to the patients, for example, via intraperitoneal administration or injection. The therapeutic agents of this technology are also useful for the purpose of manufacturing medicament for the treatment of relevant diseases and conditions as described in this application.

V. Combination Therapies

In some embodiments, IL-33 compounds of the present technology are incorporated into pharmaceutical compositions for administration, singly or in combination with one or more additional therapeutic agents, to a subject for the treatment or prevention of a particular condition. In some embodiments, the condition is a neurodegenerative disease or neuroinflammatory disorder. In some embodiments, the condition is Alzheimer's disease (AD), Parkinson's disease (PD), or mild cognitive impairment (MCI).

In one embodiment, an additional therapeutic agent is administered to a subject in combination with least one IL-33 compound of the present technology such that a synergistic therapeutic effect is produced.

In some embodiments, multiple therapeutic agents (including IL-33 compounds) are administered in any order or even simultaneously. If simultaneously, the multiple therapeutic agents are provided in a single, unified form, or in multiple forms (by way of example only, either as a single pill or as two separate pills). In some embodiments, one of the therapeutic agents is administered in multiple doses, or both may be given as multiple doses. In addition, the combination methods, compositions, and formulations are not to be limited to the use of only two agents.

Specific, non-limiting examples of possible combination therapies include the use of one or more of IL-33 compounds in combination with an active agent specific for a particular disease or disorder. In some embodiments, the active agent is selected from the group consisting of an acetylcholinesterase inhibitor, an N-Methyl-D-Aspartate receptor (NMDAR) antagonist, aducanumab, a heterodimer of different chemical moieties (see, e.g., U.S. Pat. No. 7,605,265), rosiglitazone, bexarotene, an angiotensin 2 receptor blocker, DA001 or its derivatives (see, e.g., U.S. Pat. No. 8,642,567 and U.S. Pat. No. 9,029,414), rhynchophylline, and Rhy derivatives. In some embodiments, the acetylcholinesterase inhibitor is selected from the group consisting of donepezil, rivastigmine, and galantamine. In some embodiments, the NMDAR is memantine. In some embodiments, the angiotensin 2 receptor blocker is losartan. In some embodiments, the Rhy derivative is Rhy-37 (see, e.g., PCT/CN2014/082386).

VI. Pharmaceutical Compositions and Modes of Administration

The present technology also provides pharmaceutical compositions or physiological compositions comprising an effective amount of one or more therapeutically active agents (e.g., IL-33, optionally in combination with a second active agent) and therefore provides the intended benefits in both prophylactic and therapeutic applications. Such pharmaceutical or physiological compositions also include one or more pharmaceutically or physiologically acceptable excipients or carriers. Pharmaceutical compositions of the present technology are suitable for use in a variety of drug delivery systems. Suitable formulations for use in the present technology are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

In some embodiments, methods described herein comprise contacting a cell, organ, or tissue with compositions and/or agents described herein, or pharmaceutically acceptable salts thereof. Any method known in the art may be employed, including in vitro, in vivo, and ex vivo methods. In vitro methods typically include the use of cultured samples. For example, a cell can be placed in a reservoir (e.g., tissue culture plate), and incubated with an agent under appropriate conditions suitable for obtaining the desired result. Suitable incubation conditions can be readily determined using methods known in the art. Ex vivo methods typically include cells, organs, or tissues removed from a mammal, such as a human. The contacted cells, organs, or tissues are typically returned to the donor, placed in a recipient, or stored for future use. In vivo methods typically include the administration of an agent, such as those described herein, to a subject such as a human. When used in vivo for therapy, an agent of the present technology is administered to a mammal in amounts effective for the desired outcome and by a route of administration suitable for the desired outcome.

In some embodiments, agents and compositions of the present technology are formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regimen).

Pharmaceutical compositions are typically formulated to be compatible with the intended route of administration. The pharmaceutical compositions of the present technology can be administered by various routes including, for example, parenteral (e.g., intravenous, intradermal, intraperitoneal, or subcutaneous), intracranial, intracerebroventricular, intrathecal, oral, respiratory (e.g., by inhalation), transdermal (topical), iontophoretic, and transmucosal administration.

For example, in some illustrative embodiments, routes of administering the pharmaceutical compositions are local delivery to an organ or tissue suffering from a condition caused or exacerbated by loss or damage to neuronal cells at daily doses of about 0.01-2500 mg of an active agent for a 70 kg adult human per day. In some embodiments, the daily dose is about 2.5-500 mg of an active agent for a 70 kg adult human per day. The appropriate dose may be administered in a single daily dose or as divided doses presented at appropriate intervals, for example as two, three, four, or more subdoses per day. In some embodiments, the dose is delivered by intraperitoneal injection over a time period of 2 days.

In one embodiment, agents of the present technology are administered intravenously. For example, agents of the present technology may be administered via rapid intravenous bolus injection. In some embodiments, agents of the present technology are administered as a constant-rate intravenous infusion.

In some embodiments, agents of the present technology administered systemically, intracerebroventricularly, intrathecally, topically, intranasally, subcutaneously, or transdermally utilize conventional pharmaceutical carriers, diluents, or excipients, etc., such as those known in the art to deliver the agents of the present technology. For example, in some embodiments, the compositions of the present technology further comprise one or more of the following: a stabilizer, a surfactant, such as a nonionic surfactant, and optionally a salt and/or a buffering agent. Supplementary active compounds can also be incorporated into the compositions.

In some embodiments, the pharmaceutical carrier is in the solid or liquid form. In some embodiments, solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In some embodiments, for powders, the carrier is generally a finely divided solid that is in a mixture with the finely divided active component or components. In some embodiments, for tablets, the active ingredient is mixed with the carrier having the necessary binding properties in suitable proportions and compacted in the shape and size desired.

In some embodiments, for preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

In some embodiments, powders and tablets contain between about 5% to about 70% by weight of the active ingredient of an active agent of the present technology. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

In some embodiments, the pharmaceutical compositions of the present technology can include the formulation of the active compound of an active agent with encapsulating material as a carrier providing a capsule in which the active agent (with or without other carriers) is surrounded by the carrier, such that the carrier is thus in association with the compound. In a similar manner, cachets can also be included. In some embodiments, tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an active agent such as IL-33, optionally in combination with an additional active agent) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

In some embodiments, solutions or suspensions used for parenteral, intradermal, or subcutaneous application, including compositions of the present technology suitable for injectable use, can include the following components: a sterile diluent such as water (where water soluble) for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid;

buffers such as acetates, citrates or phosphates, and agents for the adjustment of tonicity, such as sodium chloride or dextrose. In some embodiments, compositions of the present technology formulated for intravenous administration comprise a carrier including physiological saline, bacteriostatic water, Cremophor EL® (BASF, Parsippany, N.J., USA), or phosphate buffered saline (PBS). In all cases, a composition for parenteral administration must be sterile and should be formulated for ease of syringeability. The composition should be stable under the conditions of manufacture and storage, and must be shielded from contamination by microorganisms such as bacteria and fungi. In some embodiments, the pH can be adjusted with acids or bases, such as hydrochloric acid or sodium hydroxide. The preparation can be enclosed in ampoules, disposable syringes or multiple-dose vials made of glass or plastic. In some embodiments, for the convenience of the patient or treating physician, the dosing formulation can be provided in a kit containing all necessary equipment (e.g., vials of drug, vials of diluent, syringes and needles) for a course of treatment.

In some embodiments, the stabilizer comprises an amino acid, such as for instance, glycine; an oligosaccharide, such as, sucrose, tetralose, lactose; or a dextran. Alternatively, the stabilizer may comprise a sugar alcohol, such as, mannitol. In some embodiments, the stabilizer or combination of stabilizers constitutes from about 0.1% to about 10% weight for weight of the formulated composition.

In some embodiments, the surfactant comprises a non-ionic surfactant (such as a polysorbate), an anionic surfactant (such as dioctyl sodium sulfosuccinate), a cationic surfactant (such as cetylpyridinium chloride), or a combination thereof. Examples of suitable non-ionic surfactants include polyoxyethylene sorbitan esters (e.g., Tween-20 and Tween-80), p-t-octyl phenol polyoxyethylenes (e.g., Triton X-45, Triton X-100, Triton X-114, and Triton X-305), a polyethylene glycol or a polyoxyethylene polyoxypropylene glycol, such as Pluronic F-68, nonylphenoxypoloxyethylenes (e.g., Igepal CO series), and polyoxyethylene ethers (e.g. Brij 36T, Brij 52, Brij 56, Brij 76, Brij 96, Texaphor A6, Texaphor A14, and Texaphor A60), at from about 0.001% (w/v) to about 10% (w/v).

In some embodiments, the salt or buffering agent comprises any salt or buffering agent, such as for example, sodium chloride, or sodium/potassium phosphate, respectively. In some embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

VII. Dosage

The dosage ranges and regimens described herein are exemplary and are not intended to be limiting.

Dosage, toxicity, and therapeutic efficacy of the agents of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to unaffected cells, and thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any agent of the present technology used in the methods described herein, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, the pharmaceutical compositions containing an active agent(s) of the present technology are administered for prophylactic and/or therapeutic treatments. In some embodiments, the compositions are administered to a patient already suffering from a condition as a therapeutic application in an amount sufficient to prevent, cure, reverse, or at least partially slow or arrest the symptoms of the condition and its complications. In some embodiments, the compositions are administered to a patient suffering from a condition that may be ameliorated by neurogenesis such as the onset, progression, and worsening of AD, MCI, or PD. An amount adequate to accomplish this is defined as a "therapeutically effective dose." Amounts effective for this use will depend on the severity of the disease or condition and the weight and general state of the patient.

In some embodiments, the pharmaceutical compositions containing an active agent(s) of the present technology are administered for prophylactic and/or therapeutic treatments. In some embodiments, the compositions are administered to a patient already suffering from a condition as a therapeutic application in an amount sufficient to prevent, cure, reverse, or at least partially slow or arrest the symptoms of the condition and its complications. In some embodiments, the compositions are administered to a patient suffering from a condition that may be ameliorated by neurogenesis such as the onset, progression, and worsening of AD, MCI, or PD. An amount adequate to accomplish this is defined as a "therapeutically effective dose." Amounts effective for this use will depend on the severity of the disease or condition and the weight and general state of the patient. In some embodiments, a therapeutically effective dose ranges from about 0.000001 mg to about 10,000 mg per kilogram body weight per day. In some embodiments, the therapeutically effective does ranges from about 0.000001 mg to about 0.0001 mg, about 0.001 mg, about 0.01 mg, about 0.05 mg, about 0.1 mg, about 0.5 mg, about 1.0 mg, about 5.0 mg, about 10 mg, about 50 mg, about 100 mg, about 200 mg, about 300 mg, about 400 mg, about 500 mg, about 600 mg, about 700 mg, about 800 mg, about 900 mg, about 1,000 mg, about 1,500 mg, about 2,000 mg, about 3,000 mg, about 4,000 mg, about 5,000 mg, about 6,000 mg, about 7,000 mg, about 8,000 mg, about 9,000 mg, or about 10,000 mg per kilogram body weight per day.

For example, in some illustrative embodiments, the dosage ranges from about 0.0001 mg to about 2,500 mg of the active agent(s) per day for a 70 kg patient. In some embodiments, the dosage ranges from about 0.0002 mg to about 2,500 mg of the active agent(s) per day for a 70 kg patient. In some embodiments, the dosage ranges from about 0.0005 mg to about 2,500 mg of the active agent(s) per day for a 70 kg patient. In some embodiments, the dosage ranges from about 0.001 mg to about 2,500 mg of the active agent(s) per day for a 70 kg patient. In some embodiments, the dosage ranges from about 0.01 mg to about 2,500 mg of the active agent(s) per day for a 70 kg patient. In some embodiments, the dosage ranges from about 0.1 mg to about 2,500 mg of the active agent(s) per day for a 70 kg patient. In some embodiments, the dosage ranges from about 2.5 mg to about 500 mg of the active agent(s) per day for a 70 kg patient.

In some embodiments, IL-33 concentrations in a carrier or diluent range from about 0.01 µg to about 0.1 µg, about 0.5 µg, about 1.0 µg, about 5 µg, about 10 µg, about 20 µg, about 30 µg, about 40 µg, about 50 µg, about 100 µg, about 200 µg, about 300 µg, about 400 µg, about 500 µg, about 600 µg, about 700 µg, about 800 µg, about 900 µg, about 1000 µg, about 1500 µg, about 2000 µg per delivered milliliter.

In some embodiments, a therapeutically effective dose or a prophylactically effective dose of the compositions of the present technology is defined as a concentration of the IL-33 compound at the target tissue of $10^{-11}$ to $10^{-6}$ molar, e.g., approximately $10^{-7}$ molar. The dosage regimen is optimized to maintain the therapeutic concentration at the target tissue, such as by single daily or weekly administration, but also including continuous administration.

Single or multiple administrations of the compositions can be carried out with dose levels and pattern being selected by the treating physician. The appropriate dose may be administered in a single daily dose or as divided doses presented at appropriate intervals, for example as two, three, four, or more subdoses per day.

In some embodiments, regimens for the treatment or prevention of a neurodegenerative or neuroinflammatory condition comprise administration of one or more compositions of the present technology at specified intervals. In some embodiments, the compositions are administered more than once per day. In some embodiments, the compositions are administered once per 1 day, 2 days, 3 days, 4 days, 5 days, 6 days, or 7 days. In some embodiments, the compositions are administered once per 1 week, 2 weeks, 3 weeks, 4 weeks, 5 weeks, 6, weeks, 7 weeks, 8 weeks, 9 weeks, or 10 weeks. In some embodiments, the compositions are administered once per 1 month, 2 months, 3 months, 4 months, 5 months, 6 months, 7 months, 8 months, 9 months, 10 months, 11 months, or 12 months. In some embodiments, the compositions are administered once per 1 year, 2 years, 3 years, 4 years, 5 years, or longer (i.e., less than once per five years).

In some embodiments, regimens for the treatment or prevention of a neurodegenerative or neuroinflammatory condition comprise administration of one or more compositions of the present technology followed by a rest interval prior to additional administration of the composition. In some embodiments, the treatment regimen comprises multiple administrations of a composition, each of which is followed by a rest period. In some embodiments, the composition is administered as a single dose followed by a rest period of up to 1 day, 2 days, 3 days, 4 days, 5 days, 6 days, or 7 days, 1 week, 2 weeks, 3 weeks, 4 weeks, 5 weeks, 1 month 2 months, 3 months, 4 months, 5 months, 6 months, 7 months, 8 months, 9 months, 10 months, 11 months, or 12 months prior to administration of additional compositions.

In some embodiments, treatment regimens comprise multiple administrations of composition, each of which is followed by a rest period. In some embodiments, the rest periods within a treatment regime may be variable. For example, a treatment regimen may comprise a first rest period of 1 week, a second rest period of two weeks, and a third rest period of three weeks. Likewise, the treatment regimen may include a first rest period of 1 year, a second rest period of two years, and a third rest period of three years. Suitable intervals for rest and composition administration may be determined on an individual basis using clinical methods known in the art such as, but not limited to, measuring disease markers during the course of treatment.

For example, in some illustrative embodiments, a full dose (e.g., as a single daily dose or as divided doses administered at appropriate intervals) is administered to the subject followed by a rest period of 1 day, after which a second full dose is administered to the subject. In another illustrative embodiment, a full dose (e.g., as a single daily dose or as divided doses administered at appropriate intervals) is administered to the subject on day 1 followed by a rest period of 1 day, after which a second full dose is administered to the subject, followed by a rest period of two days, after which a third full dose is administered to the subject, followed by a rest period of 1 day, after which a fourth full dose is administered to the subject, followed by a rest period of 1 day, after which a fifth full dose is administered to the subject. In another illustrative embodiment, a 21-day treatment regimen is used. In this regimen, a full dose (e.g., as a single daily dose or as divided doses administered at appropriate intervals) is administered to the subject on day 1 followed by a rest period of 1 day, after which a second full dose is administered to the subject on day 2, followed by a rest period of two days, after which a third full dose is administered to the subject on day 5, followed by a rest period of 1 day, after which a fourth full dose is administered to the subject on day 7, followed by a rest period of 1 day, after which a fifth full dose is administered to the subject on day 9, followed by a rest period of 3 days, after which a sixth full dose is administered to the subject on day 13, followed by a rest period one day, after which a seventh full dose is administered to the subject on day 15, followed by a rest period of one day, after which an eighth full dose is administered to the subject on day 17, followed by a rest period of one day, after which a ninth full dose is administered to the subject on day 19, followed by a rest period of one day, after which a tenth full dose is administered to the subject on day 21.

In some embodiments, a known therapy such as a computer-based cognitive training method (see, e.g., Hofmann et al., *J Psychiatr Res*. 1996 November-December; 30(6):493-501) is used in combination with the administration of at least one of IL-33 compound in the treatment regimens described above.

Intervals can also be irregular as indicated by measuring blood levels of glucose or insulin in the subject and adjusting dosage or administration accordingly. In some methods, dosage is adjusted to achieve a desired fasting glucose or fasting insulin concentration. In any event, the pharmaceutical formulations should provide a quantity of an active agent (optionally in combination with a second active agent) sufficient to effectively suppress, inhibit, or even reverse the onset or progression of neurodegeneration or neuroinflammation in the patient, either therapeutically or prophylactically.

VIII. Diagnostic Method

In some embodiments, the present technology provides a novel method for detecting the presence of a disorder in a patient or for assessing the risk of an individual to develop a disorder in the future even though there are otherwise no indication of such disease at the present time. In some embodiments, the present technology provides a novel method for detecting the presence of a neurodegenerative or neuroinflammatory disorder in a patient or for assessing the risk of an individual to develop a neurodegenerative or neuroinflammatory disorder in the future even though there are otherwise no indication of such disease at the present time. The method involves determining the level of sST2 in a patient's biological sample and detecting any increase from a standard control, which can indicate the presence of, or an elevated risk of developing, a neurodegenerative or neuroinflammatory disorder in the patient.

To practice this method one typically analyzes the amount of sST2, either in the protein form or in the mRNA form, found in a sample taken from a person being tested, e.g., a blood sample. Collection of blood from an individual is performed in accordance with the standard protocol hospitals or clinics generally follow. An appropriate amount of peripheral blood, e.g., typically between 5-50 mL, is collected and may be stored according to standard procedure prior to further preparation.

The analysis of sST2 protein or mRNA found in a patient sample according to the present technology may be performed using, e.g., the whole blood, or more often in an acellular sample such as serum, or plasma. Standard methods known in the research field can be used to isolate and analyze the protein or RNA level of sST2 in the sample. (See, e.g., Sambrook and Russell, *Molecular Cloning: A Laboratory Manual* 3d ed., 2001).

In order to establish a standard control for practicing the method of the present technology, a group of healthy persons free of any neurodegenerative or neuroinflammatory disorders and not known to be at risk of developing such disorders are first selected. These individuals are within the appropriate parameters, if applicable, for the purpose of screening for and/or assessing future risk of such disorders using the methods of the present technology. Optionally, the individuals are of the same or comparable gender, age, ethnic background, and medical history. The healthy status of the selected individuals is confirmed by well established, routinely employed methods including but not limited to general physical examination of the individuals and general review of their medical records.

Furthermore, the selected group of healthy individuals must be of a reasonable size, such that the average amount/concentration of sST2 in the samples obtained from the group can be reasonably regarded as representative of the normal or average level among the general population of healthy people without and not at risk of developing a neurodegenerative or neuroinflammatory disorder. Preferably, the selected group comprises at least 10 human subjects.

Once an average value for the sST2 protein or mRNA is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, ethnic background, or any distinct past event(s) in the medical history.

IX. Kits

The present technology provides a kit for diagnosing or determining risk of neurodegeneration/neuroinflammatory disease in a subject. The kit typically comprises (1) a container containing an agent for determining sST2 level in a biological sample taken from the subject, such as an antibody that specifically recognizes sST2 (which may or may not also specifically recognizes ST2L, since sST2 is secreted and can be found in acellular portions of the samples whereas ST2L is membrane-bound and therefore remains with the cells in the samples, making the two types of ST2 proteins readily distinguishable even using antibodies that recognize them both) or a polynucleotide probe that specifically binds a coding sequence for sST2 but not ST2L (e.g., sST2 mRNA but not ST2L mRNA); and (2) a container containing a standard control indicating sST2 level (which may be protein or mRNA) in the same type of biological sample taken from an average healthy subject not suffering from and not at risk of suffering from neurodegeneration. Often an instructional manual is included in the kit for directing users to properly perform the diagnostic method.

The present technology also provides a kit for inhibiting or treating neurodegeneration or neuroinflammatory conditions for therapy or prevention of the pertinent diseases and conditions according to the method of this disclosure. The kits typically include a container that contains (1) a pharmaceutical composition having an effective amount of an active agent (for instance, IL-33, optionally in combination with a second or more active ingredients) and (2) informational material containing instructions on how to dispense the pharmaceutical composition, including description of the type of patients who may be treated (e.g., patients suffering from AD, MCI, PD, depression, stroke, or traumatic brain injury), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results. The examples should in no way be construed as limiting the scope of the present technology, as defined by the appended claims.

Materials and Methods for Examples 1-12

Chemicals and Antibodies.

Antibodies specific for IL-33 (clone Nessy-1) and APP were purchased from Biolegend and Abcam, respectively; Iba1 antibody was from Wako; APC-conjugated antibody against mouse CD11b (clone M1/70) and FITC-conjugated antibody against CD45 (clone 30-F11) were from eBioscience; Aβ17-24 antibody (clone 4G8) was from Covance; insulin-degrading enzyme (IDE) antibody was from Calbiochem; neprilysin (NEP) antibody was from Santa Cruz; actin antibody was from Sigma-Aldrich. Soluble ST2 (sST2)-Fc recombinant protein was purchased from R&D Systems; fluorescein-conjugated (FAM)-Aβ1-42 monomer was from rPeptide; methoxy-X04 (MeX04) was purchased from Tocris Bioscience; Hoechst 34580, human Aβx-40 and Aβx-42 commercial ELISA kits and Alexa Fluor secondary antibodies were purchased from Life Technologies.

Animal Manipulation.

All animal experiments were approved by the Animal Care Committee of The Hong Kong University of Science and Technology. The APP/PS1 double-transgenic mice were generated by incorporating a human/mouse APP construct bearing the Swedish double mutation and the exon-9-deleted PSEN1 mutation (APPswe+PSEN1/dE9). All in vivo analyses were performed on sex- and age-matched groups; mice of both sexes were used for experiments except behavioral tasks, for which only male mice were used. The APP/PS1 transgenic mice and their wild-type (WT) controls were randomly assigned to each experimental condition. The genotype was confirmed by PCR analysis of tail biopsies. Four to five mice of the same sex were housed per cage with 12-hour light/dark cycle with food and water ad libitum. Sample sizes were primarily chosen on the basis of experience with similar types of experiments.

Mouse recombinant IL-33 (200 ng per mouse) was intraperitoneally (i.p.) injected into APP/PS1 mice (from 7-17 months old) daily. The administration paradigm of IL-33 differed for each experiment. Mice used to study amyloid plaque load, microglial phagocytosis of AP, and long-term potentiation (LTP) were administered IL-33 daily for 2 days. For animal behavioral tests, mice were i.p. injected with IL-33 once per day for 2 consecutive days before starting the open field test and then on alternate days during the course of the behavioral experiments.

sST2 was delivered into 10-11-month-old APP/PS1 mice via mini-osmotic pumps at 0.11 µL/h (model 1004; Alzert). The pumps were loaded with mouse recombinant sST2 protein (240 ng per pump; 10 µg/mL) or vehicle solvent in artificial cerebral spinal fluid (aCSF). After 2 days of sST2 delivery, IL-33 was administered i.p. to mice for 2 more days. At the end of treatment, the mice were perfused with Dulbecco's phosphate-buffered saline (DPBS) and fixed with 4% paraformaldehyde.

Immunohistochemistry.

To examine amyloid plaque load, the perfused mouse brains were cryosectioned coronally (20 µm) for immunohistochemistry. Briefly, antigen retrieval was performed by microwave heating the brain slices in sodium citrate buffer (10 mM trisodium citrate, 0.5% Tween-20 in $H_2O$ [pH 6.0]) for 10 minutes followed by incubation with 3% $H_2O_2$ in $H_2O$ for 20 min to inhibit endogenous peroxidase activity. The sections were blocked with 2% goat serum in Tris-buffered saline (TBS) for 20 min and subsequently labeled with Aβ17-24 antibody (dilution 1:1000) in blocking buffer overnight at 4° C. Mouse brain sections were subsequently labeled with a Dako HRP-linked goat anti-mouse IgG antibody for 50 min at room temperature and subsequently developed using a Dako DAB chromogen kit according to the manufacturer's instructions. Imaging was performed using a Leica DM6000 B fully automated upright compound microscope system in combination with a Leica HC PL FLUOTAR 10×/0.30 objective lens. To determine the number and density of Aβ plaques in the cortex and hippocampus of the brain sections, stitched images of whole-brain sections were analyzed by a stereological cell counting method using the Stereo Investigator software (mbf Bioscience). The counting frame and sampling grid were 180×180 µm and 400×400 µm, respectively. The coefficients of error of the analyzed images were all less than 0.1 to ensure unbiased random sampling and hence precise estimates.

To examine the colocalization of amyloid plaques and microglia, the perfused mouse brains were blocked with 1% bovine serum albumin, 4% goat serum, and 2.5% Triton X-100 in DPBS for 30 min at room temperature and subsequently incubated with Iba1 (dilution 1:500) and Aβ17-24 (dilution 1:1000) antibodies in blocking buffer overnight at 4° C. Brain slices were then labeled by Alexa Fluor secondary antibodies (dilution 1:1000). To label nuclei, slices were incubated with Hoechst 34580 (5 µg/mL). Imaging was performed using a Leica TCS SP8 confocal system in combination with a Leica HC PL APO 63×/1.40 oil CS2 objective lens.

ELISA for Aβ and Human ST2.

Aβ was sequentially extracted from the soluble and insoluble fractions of the mouse cortex or hippocampus. Briefly, the mouse cortex was homogenized in buffer containing 250 mM sucrose, 20 mM Tris-HCl (pH 7.4), 1 mM EDTA, 1 mM EGTA, and protease inhibitor cocktail (Sigma-Aldrich). Aβ was sequentially extracted by diethylamine (DEA; soluble) followed by formic acid (FA; insoluble). Aβx-40 and Aβx-42 were analyzed by ELISA (Invitrogen) according to the manufacturer's instructions. The plasma of MCI, AD, and control patients were collected and subjected to ST2 ELISA.

Fam-Aβ1-42 Preparation.

Monomeric Aβ1-42 was dissolved in dry DMSO and diluted in ice-cold phenol red-free F-12 medium to yield a final concentration of 100 µM. The FAM-Aβ1-42 solution was incubated for 24 h at 4° C. and then centrifuged at 14,000×g for 10 min. The supernatant was frozen in liquid nitrogen and stored at −20° C. for up to 1 month.

Isolation of Mouse Microglia.

Microglia were isolated from adult mice. Briefly, mice were anaesthetized and perfused with ice-cold DPBS. The isolated cortices were cut into smaller pieces and subsequently dissociated enzymatically and mechanically using a papain-based neural dissociation kit with gentleMACS™ dissociator system (Miltenyi Biotec) according to the manufacturer's instructions. 30% Percoll gradient (Sigma-Aldrich) was used to remove myelin. The resultant mononuclear cell suspensions were used for flow cytometric analysis or setting up microglia cultures.

Flow Cytometry.

Seventeen-month-old APP/PS1 mice were either i.p. injected with IL-33 in DPBS or DPBS alone once per day for 2 consecutive days. The following day, the mice were i.p. injected with 10 mg/kg MeX04. Two WT C57 mice were also injected with MeX04 as controls. Three hours after MeX04 injection, the mice were sacrificed. Isolated mononuclear cell suspensions from the mouse brain cortex were then incubated with a mouse FcR blocking reagent (Miltenyi Biotec) and labeled with a APC-conjugated mouse CD11b (dilution 1:100) and FITC-conjugated CD45 (dilution 1:100) antibodies. The populations of cells in the suspensions were analyzed by a Becton Dickinson FACSAria IIIu flow cytometer. According to the forward and side scatter parameters, cell debris was gated out to enable analysis of mononuclear cells in the suspensions. Myeloid cells (i.e., $CD11b^+$ cells) were identified on the basis of higher APC fluorescence intensity. Furthermore, among the $CD11b^+$ population, the CD45 expression level was further distinguished according to FITC fluorescence intensity, in which the $CD11b^+CD45^{lo}$ and $CD11b^+CD45^{hi}$ populations were identified as microglia and macrophages, respectively.

In vitro microglial phagocytosis assay. Isolated microglia cells prepared from 1.5-2-month-old $ST2^{+/+}$ or $ST2^{-/-}$ mice were incubated with CD11b antibody (clone M1/70)-conjugated microbeads (dilution 1:20) and separated by MS columns (Miltenyi Biotec) attached to a magnetic holder. $CD11b^+$ cells (microglia) were eluted and seeded in 8-well chamber slides (30,000 cells per well; SPL Life Sciences) with DMEM/F12 medium (Life Technologies) supplemented with 10% fetal bovine serum (Invitrogen) and 2 mM L-glutamine (Life Technologies). At 6-7 days in vitro, microglia were pretreated with IL-33 for 20 h followed by 2 µM FAM-Aβ1-42 for 1 h. The cells were then fixed with paraformaldehyde and immunostained with Iba1 antibody and Hoechst 34580. Wide-field fluorescence microscopy was performed by using an IN Cell Analyzer 6000 system (GE Healthcare). Images were acquired at 16 corresponding positions assigned by the software in each well. Intensity segmentation was applied to each channel using the same thresholding criteria across different samples. The boundaries of microglia were determined according to Iba1+ labeling intensity, and FAM-Aβ1-42 in each Iba1+ cell was quantified. The amounts of phagocytosed FAM-Aβ1-42 were compared between treatment groups. The area of phagocytosed FAM-Aβ1-42 was divided by the corresponding cell area to obtain the relative area of FAM-Aβ1-42 in a given cell. The data were subsequently normalized to the control.

Real-Time PCR, Quantitative PCR, and Digital PCR.

Total RNA from microglial cells was reverse-transcribed to cDNA using the Transcriptor First Strand cDNA Synthesis Kit (Roche), while the total RNA from the cortex was reverse-transcribed using PrimeScript RT reagent Kit (Takara). Meanwhile, sST2 and membrane-anchored ST2 (ST2L) were examined by real-time quantitative PCR (Life Technologies) and digital PCR (Biorad) using the following specific primers: sST2 forward, 5'-TCG AAA TGA AAG TTC CAG CA-3' (SEQ ID NO: 5); sST2 reverse, 5'-TGT GTG AGG GAC ACT CCT TAC-3' (SEQ ID NO: 6); ST2L forward, 5'-CAT GGC ATG ATA AGG CAC AC-3' (SEQ ID NO: 7); ST2L reverse, 5'-GTA GAG CTT GCC ATC GTT CC-3' (SEQ ID NO: 8). The RNA sequences of candidate genes determined by real-time quantitative PCR were validated by using the Universal ProbeLibrary System (Roche).

Transcriptome Analysis of Microglia.

For RNA sequencing for the transcriptome analysis, isolated microglia (i.e., CD11b+ cells) were harvested from the cortices of 12-month-old WT and APP/PS1 mice administered IL-33 or control vehicle (i.p.) for 2 days (n=2 per group). Microglia were subsequently isolated from the whole brain/cortex for RNA extraction. Total RNA was extracted by a NucleoSpin® RNA XS (Macherey-Nagel) according to the manufacturer's protocol, and an Agilent 2100 BioAnalyzer was used to assess RNA integrity. Samples with RIN>8 were processed further to construct the library, with 1 ng total RNA scaled by NanoDrop 3300 Fluorospectrometer as starting materials. Amplified full-length cDNA was obtained from the SMARTer® Ultra™ Low RNA Kit (Clontech) according to the manufacturer's protocol and further scaled to 1 ng with the Low Input Library Prep Kit (Clontech) for library construction. Sequencing was performed on illumina NextSeq 500 for 2×150 bp high-throughput sequencing (300 cycles).

To analyze the sequencing data, 8 samples (n=2 per group) with ~18 Gb/sample data were aligned to the mm10 genome assembly (UCSC) with the STAR-2nd pass pipeline. Aligned BAM files were further processed via the Cufflinks pipeline for transcriptome assembly and differential expression analysis. Missing values for gene expression were set to 0.001, with a mean of 0.5 FPKM as a cut-off to eliminate low-abundance genes in microglia.

Downstream statistical analysis was performed using the R Statistical Package, including one-way ANOVA, t-test, K-mean clustering, and calculations of means and fold changes, together with DAVID to annotate Gene ontology, GSEA for enrichment analysis, and STRINGdb to classify the protein network. All plots were constructed by using R script.

Western Blot Analysis.

Frozen brain tissues were lysed in radioimmunoprecipitation assay buffer (1% Triton X-100, 1% sodium deoxycholate, 0.1% SDS, 150 mM NaCl, 10 mM sodium phosphate, 2 mM EDTA, and 0.2% sodium vanadate) with various protease inhibitors. Western blot analysis was performed. Densitometric quantification of protein band intensity from Western blot analysis was performed using the NIH ImageJ program.

Long-Term Potentiation.

Briefly, mice were sacrificed, and whole brains were immediately resected and soaked in ice-cold aCSF supplemented with 95% $O_2$/5% $CO_2$. Brain slices (300 µm thick) were prepared using a vibratome (HM650V, Thermo) and soaked in oxygenated buffer for 2 h at 32° C. The mouse hippocampal slices were placed on a pre-coated polyethylenimine (Sigma-Aldrich) on a MED-P210A probe (Panasonic International Inc.) fabricated with 8×8 electrode arrays (20×20 µm, indium tin oxide and platinum black) with a 100-m inter-electrode distance. Electrodes were manually placed at the CA3-CA1 region under a microscope (MIC-D, Olympus, Tokyo, Japan). Each slice was submerged in and superfused with oxygenated aCSF at 1.3-1.5 mL/min. fEPSPs were recorded from the dendritic layer of CA1 neurons by selecting an electrode in the Schaffer collateral pathway as the stimulating electrode. On the basis of the stimulus-response curve, a stimulation intensity that evoked an fEPSP 30-40% of the maximum response was selected. LTP was induced by 3 trains of high-frequency stimulation (100 Hz for 1 s delivered 30 s apart). The field potential response after the tetanus was recorded for 60 min. The magnitude of LTP was quantified as the percentage change in the average slope of the fEPSP over 60 min after LTP induction.

Open Field Test.

The motor activity of the mice in the open field test was recorded and tracked by using the photobeam activity system and software from San Diego Instruments. In brief, experimental mice were placed in the center of an open-top chamber (16×16×15 in.) with an array of photobeams around the periphery. The mice were allowed to explore the chamber for 15 min each day for 3 consecutive days. Locomotor activity in the 3 training trials was recorded by the photobeams, and the distance moved was subsequently determined. The chamber was cleaned with 70% ethanol after each trial.

Statistical Analysis.

The investigators who performed the electrophysiological, immunohistochemical, flow cytometric, and behavioral tests were blinded to the genotypes of the mice and treatment conditions. All data are expressed as arithmetic mean±SEM. Statistical analyses were performed by using GraphPad Prism v5.0. The significance of differences was assessed by Student's t-test, or one- or two-way ANOVA followed by Bonferroni post hoc tests as indicated. The level of significance was set at $p<0.05$.

Example 1: IL-33 Ameliorates Synaptic Impairment in APP/PS1 Mice

Figure 1B:
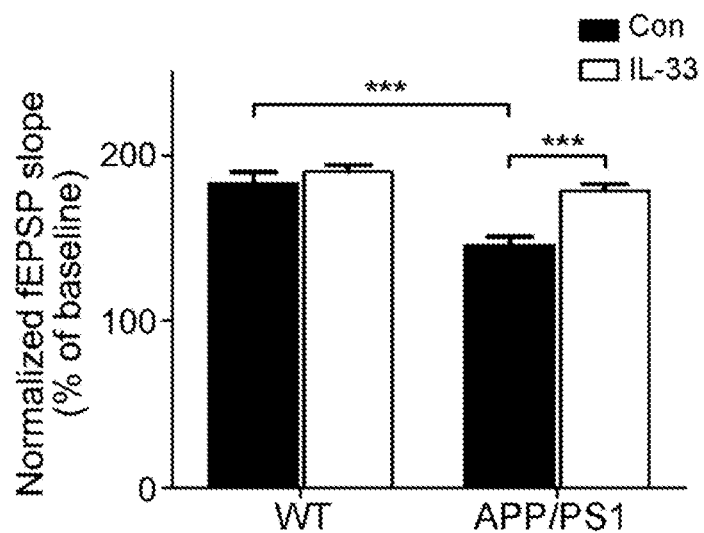

APP/PS1 and WT mice (~7.5-months-old) were intraperitoneally (i.p.) administered with IL-33 for 2 days and synaptic function was examined by long-term potentiation (LTP). Data presented in FIGS. 1A-1B show that i.p. injection of recombinant IL-33 (200 ng) for two days dramatically reversed the LTP impairment of APP/PS1 mice.

Example 2: IL-33 Ameliorates Behavioral Deficits in APP/PS1 Mice

Figure 2A:
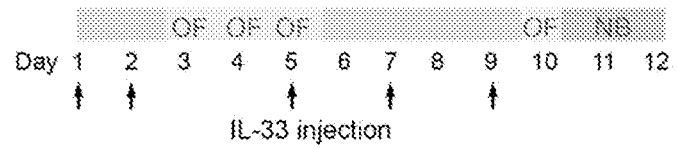
FIGS. 2A-2C show that IL-33 ameliorates behavioral deficits in APP/PS1 mice.
Figure 2B:
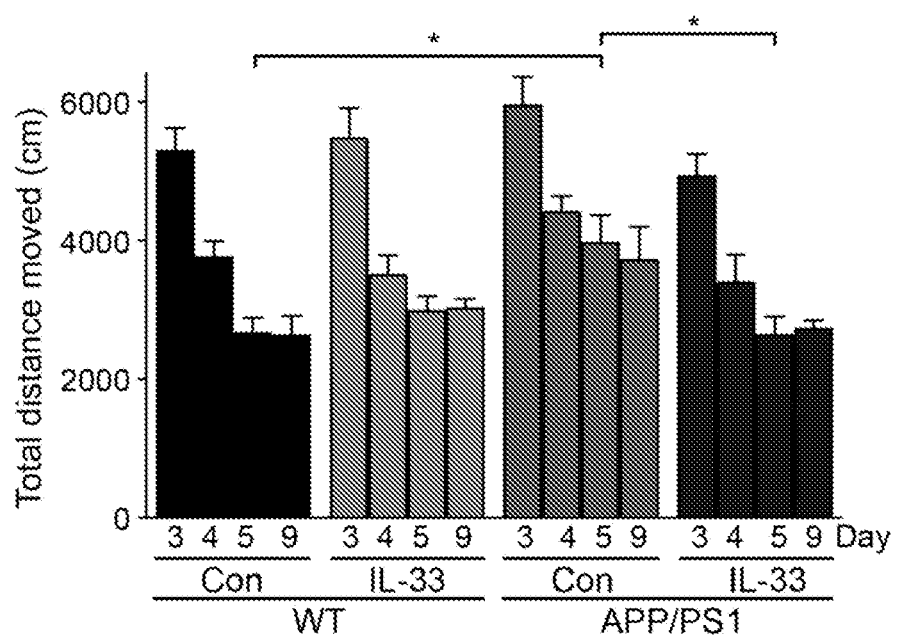
Figure 2C:
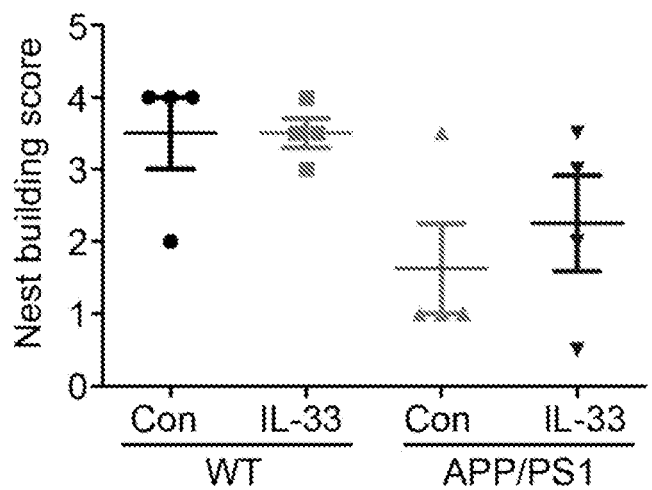

APP/PS1 mice (14-months-old) were i.p. administered with IL-33 and changes in their behavioral performance were assessed by the open field (OF) exploratory test and the nest building (NB) test. Results are presented in FIGS. 2A-2C. In the exploratory open field (OF) test, the vehicle-injected and IL-33-injected WT mice exhibited similar habituation ability in novel testing environments during the course of training (FIG. 2B). The APP/PS1 mice exhibited slower habituation to the testing environment than the WT mice; however, the IL-33-treated APP/PS1 mice showed improved habituation to the testing environment relative to untreated controls (FIG. 2B). The IL-33-treated APP/PS1 mice also showed improved nest building scores relative to untreated controls (FIG. 2C).

Example 3: IL-33 Administration Decreases Aβ Plaque Load of APP/PS1 Mice. Infusion of Soluble ST2 into Brain of APP/PS1 Mice Abolishes the Action of IL-33

Figure 3A:
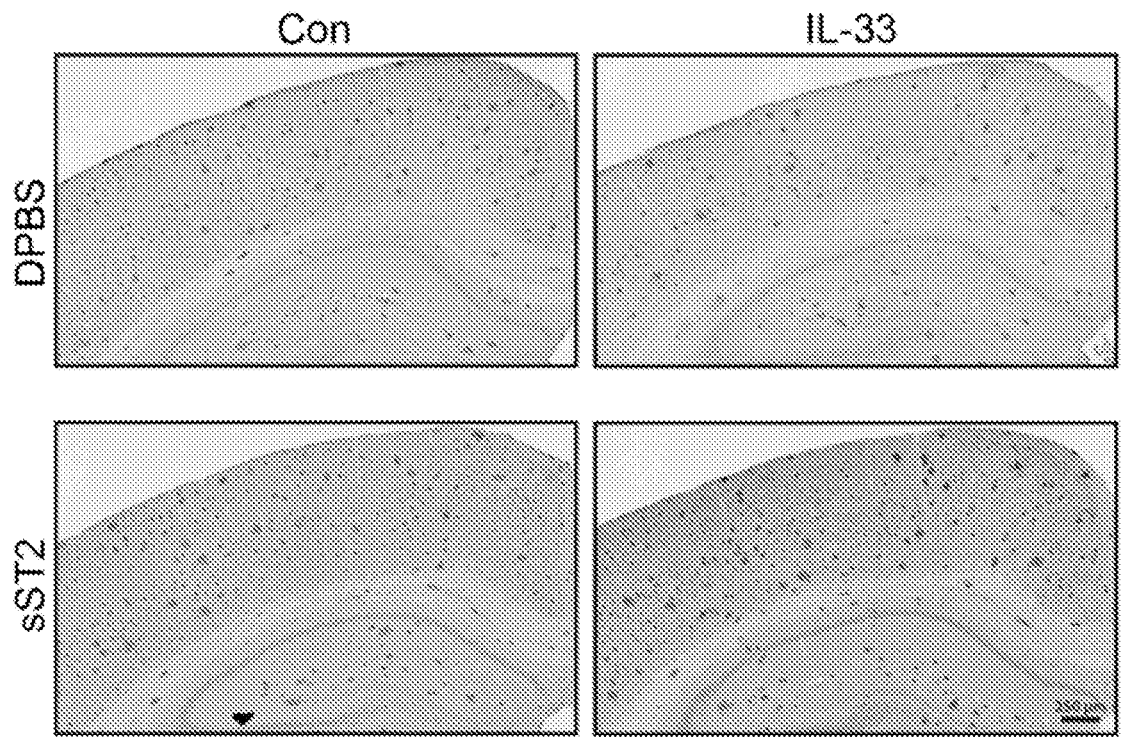
FIGS. 3A-3B show that sST2 attenuates reduction of the amyloid plaque deposition by IL-33.
Figure 3B:
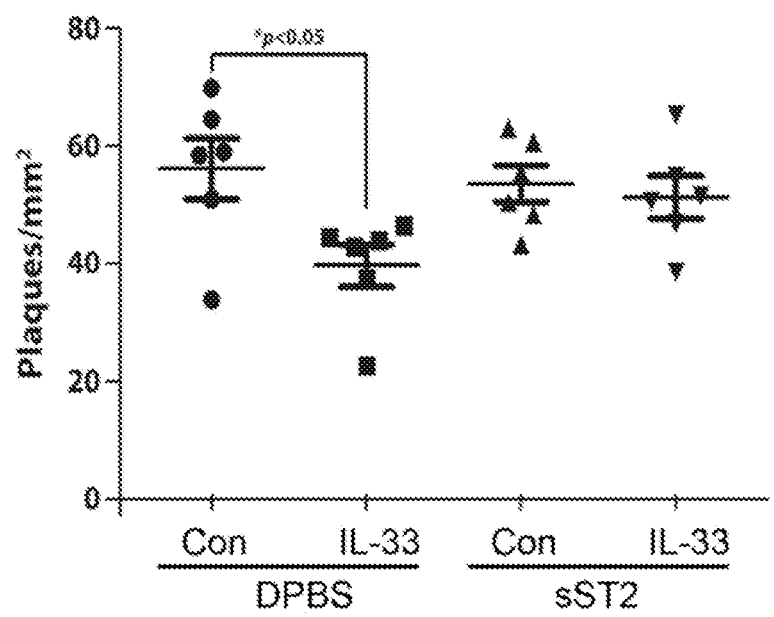

APP/PS1 mice (10-months-old) were intracerebroventricularly infused with soluble ST2 receptor by osmotic pump and i.p. administered with IL-33 for 2 days. The mouse brains were then perfused with PFA and sectioned. Brains sections were immunostained with anti-Aβ antibody (4G8) using DAB kit. Plaque densities were examined under a microscope. Results are presented in FIGS. 3A-3B. At 2 days after IL-33 treatment, the 4G8-labeled amyloid plaques were reduced in the cortices of 10-month-old APP/PS1 mice (FIG. 3A upper right panel; FIG. 3B). However, intracerebroventricular administration of sST2 abolished the IL-33-mediated reduction of 4G8-stained amyloid plaques in the APP/PS1 mice (FIG. 3A lower right panel; FIG. 3B).

Example 4: IL-33 Administration Decreases Soluble Aβ Levels in APP/PS1 Mice

Figure 4A:
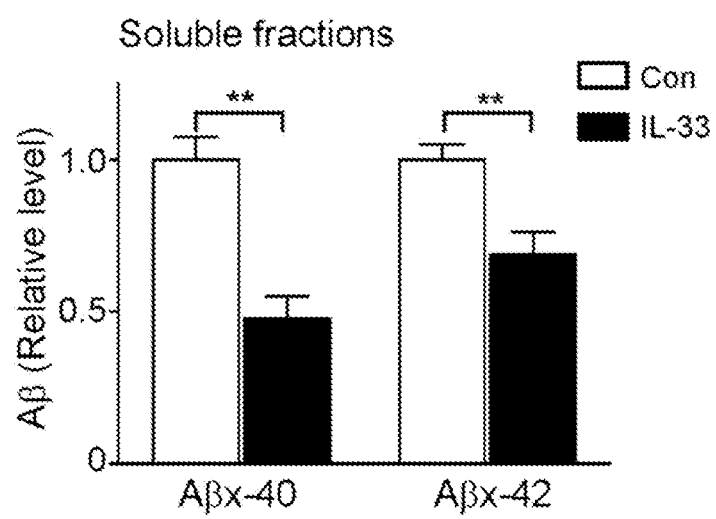
FIGS. 4A-4B show that IL-33 reduces soluble Aβ content in APP/PS1 mice. APP/PS1 mice at ~10 months of age were administered (i.p.) IL-33 for 2 days. Quantitative analysis of $A\beta_{x-40}$ and $A\beta_{x-42}$ levels in soluble (FIG. 4A, DEA-extracted) and insoluble (FIG. 4B, formic acid-extracted) fractions of cortical homogenates by ELISA [fold change compared to Con; n=4 mice, ** p<0.01, Student's t-test].
Figure 4B:
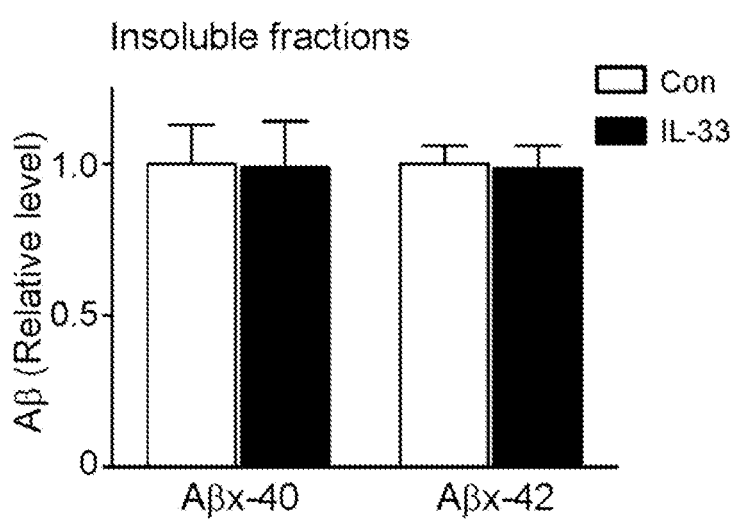

APP/PS1 mice (10-months-old) were i.p. administered with IL-33 for 2 days. The mouse brains were then collected and fractionated. The Aβ proteins were determined by Aβ ELISA kit (Life Technologies). Results are presented in FIGS. 4A-4B. IL-33 injection reduced the amounts of soluble $A\beta_{x-40}$ and $A\beta_{x-42}$ species in the cortices of 10-month-old APP/PS1 mice (FIG. 4A).

Example 5: IL-33 Enhances the Aβ Uptake of Microglia

Because the Aβ phagocytic activity of microglia directly impacts Aβ clearance, alterations in Aβ phagocytosis and degradation by resident microglia/infiltrating monocytes in APP/PS1 mouse brains following IL-33 administration were examined. APP/PS1 mice (10-months-old) were i.p. administered with IL-33 for 2 days. The mouse brains were then perfused with PFA and sectioned. Brains sections were immunostained with anti-Aβ and Iba1 (microglia marker) antibodies. The brain sections were examined under a microscope. Results are presented in FIGS. 5A-5C.

Figure 5A:
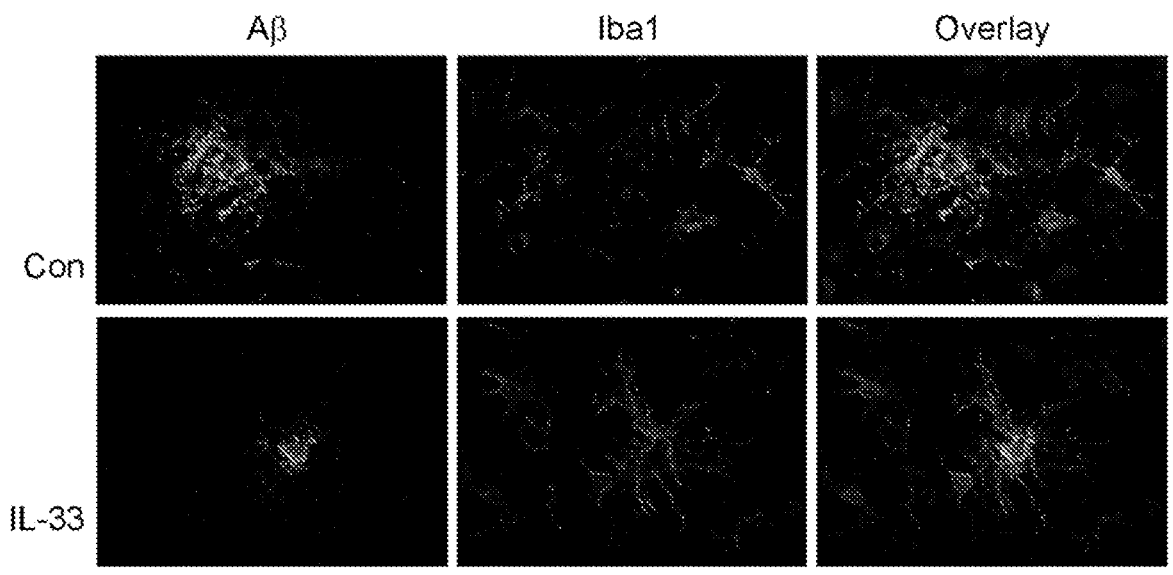
FIGS. 5A-5C show that IL-33 enhances microglia and Aβ colocalization. APP/PS1 mice were treated with IL-33 via i.p. injection for 2 days.
Figure 5B:
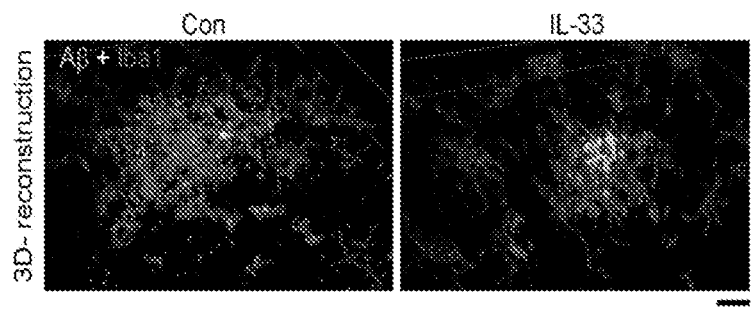
Figure 5C:
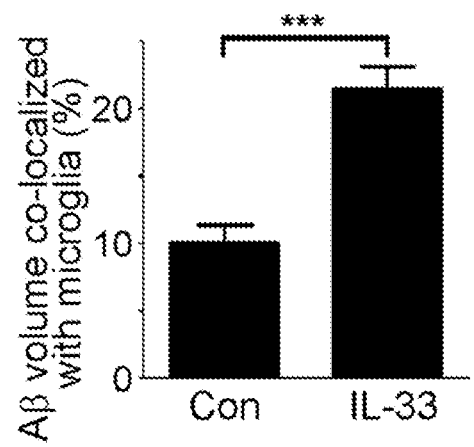

Clusters of Iba1$^+$ myeloid cells were found adjacent to the amyloid plaques in the cortices of APP/PS1 mice (FIG. 5A). IL-33 injection enhanced the recruitment of Iba1$^+$ myeloid cells to amyloid plaques in these cortices (FIG. 5A lower right panel). A 3D analysis confirmed the increased colocalization of myeloid cells and amyloid plaques in IL-33-treated APP/PSA1 mouse brains (FIGS. 5B-5C), supporting the notion that IL-33 enhances the proximity between myeloid cells and amyloid plaques.

Example 6: IL-33 Enhances Microglial Phagocytic Uptake of Aβ in APP/PS1 Mice

To demonstrate that IL-33 promotes Aβ phagocytosis by myeloid cells, APP/PS1 mice (17-months-old) were i.p. administered with IL-33 for 2 days and the Aβ uptake by microglia was labeled with methoxy-X04 (MeX04), a fluorescent dye that crosses the blood-brain barrier and specifically binds AP, by i.p. injection. Microglia were isolated and labeled with CD11b and CD45 antibodies. Flow cytometry analysis was performed to determine the phagocytic activity of microglial cells.

Figure 6A:
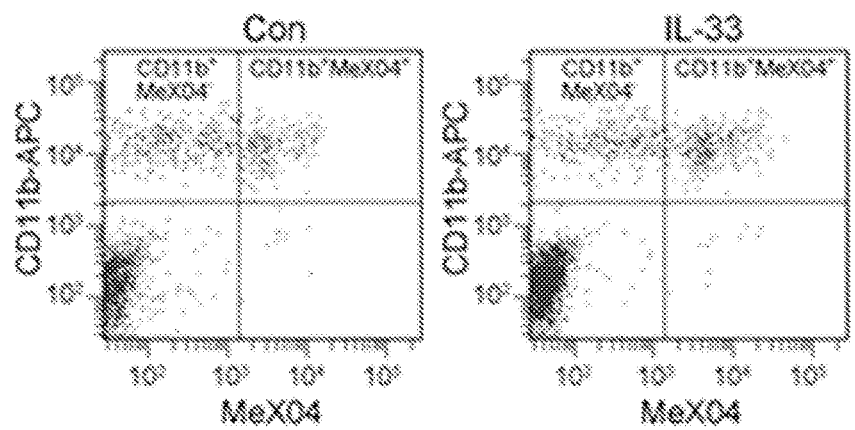
FIGS. 6A-6F show that IL-33 enhances the Aβ uptake of resident microglial cells. Representative scatter plots show the populations of mononuclear (FIG. 6A), $CD11b^+CD45^{lo}$ (FIG. 6C), and $CD11b^+CD45^{hi}$ (FIG. 6E) cells in APP/PS1 mice treated with IL-33. APP/PS1 mice were treated with IL-33 via i.p. injection for 2 days. The top quadrants (red and blue) in FIG. 6A were identified as myeloid cell populations, while the top right quadrants in FIG. 6A, and gates in FIGS. 6C and 6E, represent populations of cells that phagocytosed Aβ (MeX04$^+$). The mean proportions of MeX04$^+$ cells in the $CD11b^+$ (FIG. 6B), $CD11b^+CD45^{lo}$ (FIG. 6D), and $CD11b^+CD45^{hi}$ (FIG. 6F) populations were compared between the control and IL-33-treated groups. Con: n=5 mice, IL-33-treated group: n=6 mice from 3 independent experiments, *p<0.05, **p<0.01 Student's t-test.
Figure 6B:
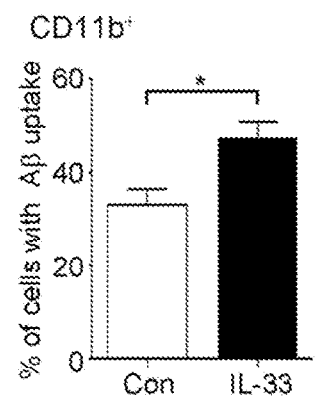
Figure 6C:
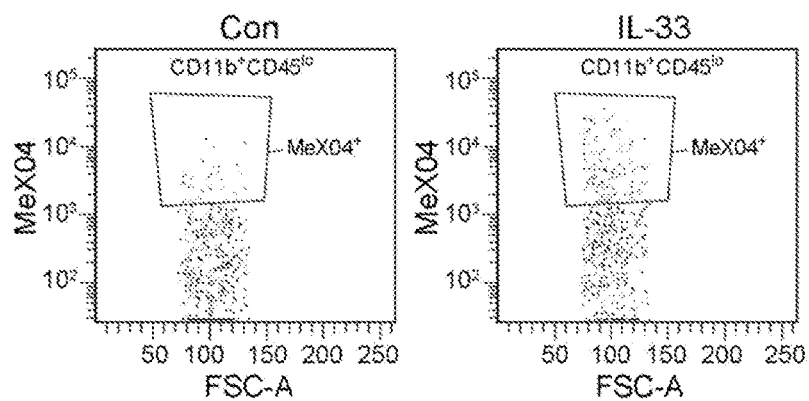
Figure 6D:
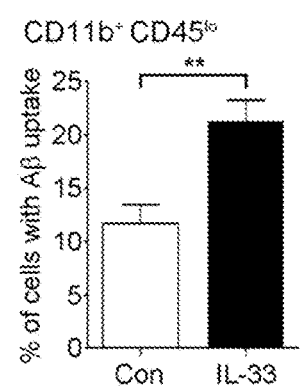
Figure 23A:
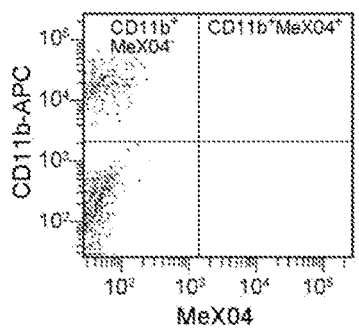
FIGS. 23A-23C show a distribution of CD11b$^+$ myeloid cell populations in the brains of wild-type mice. Adult C57BL/6 mice were i.p. injected with methoxy-X04 and sacrificed 3 h later. Mononuclear cell suspensions from the brain cortices were purified and analyzed by flow cytometry. Representative scatterplots show the populations of CD11b$^+$ (FIG. 23A), CD11b$^+$CD45$^{lo}$ (FIG. 23B), and CD11b$^+$CD45$^{hi}$ (FIG. 23C) cells with Aβ labeled by methoxy-X04. The top left quadrant in FIG. 23A (shown in blue) was identified as myeloid cell populations with no Aβ uptake, while the top right quadrant in FIG. 23A as well as gates in FIGS. 23B and 23C represent populations of cells that phagocytosed Aβ (MeX04$^+$), if any. Data are representative of two experiments.
Figure 23B:
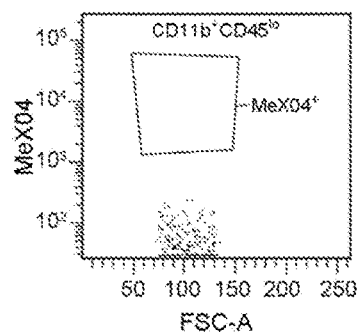
Figure 23C:
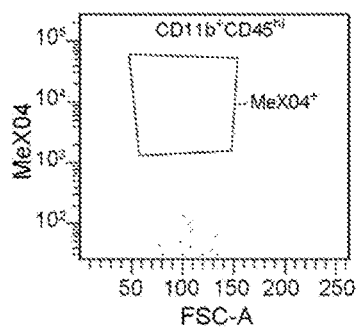

Data presented in FIGS. 6A-6F show that IL-33 enhances the Aβ uptake of resident microglial cells. Flow cytometry analysis detected MeX04-labeled Aβ in ~33% of the CD11b$^+$ myeloid cells from the cortices of the APP/PS1 mice (FIGS. 6A-6B), but not those of WT mice (FIGS. 23A-23C). IL-33 injection further increased the proportion of CD11b$^+$ cells exhibiting MeX04 fluorescence (~47%; FIGS. 6A-6B).

Figure 6E:
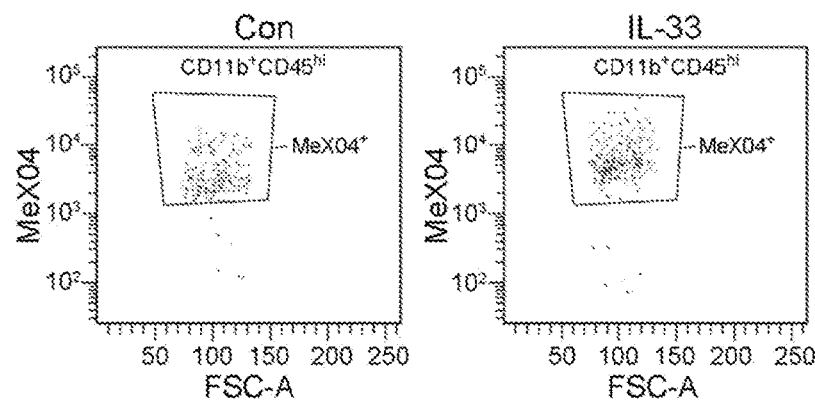
Figure 6F:
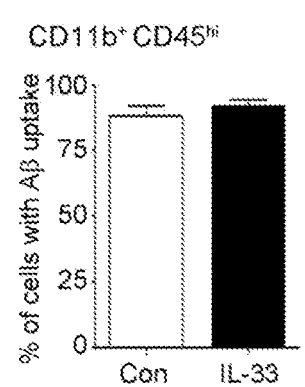
Figure 24A:
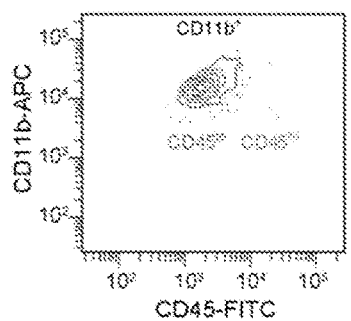
FIGS. 24A-24D show that IL-33 does not increase the infiltration of peripheral monocytes in the brains of APP/PS1 mice. WT and APP/PS1 mice (17-months-old) were i.p. injected with IL-33 (200 ng) or DPBS (Con) for two days. Mononuclear cells in the brain cortices were isolated and analyzed by flow cytometry.
Figure 24B:
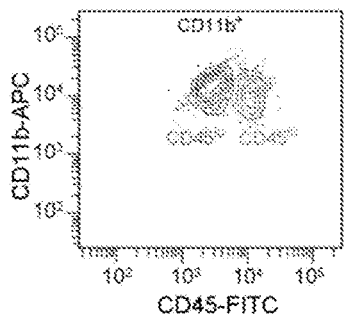
Figure 24C:
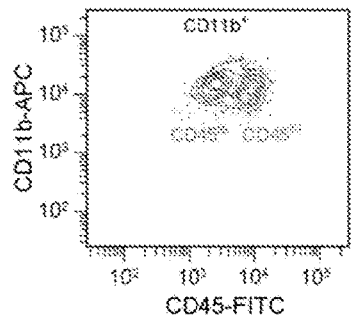
Figure 24D:
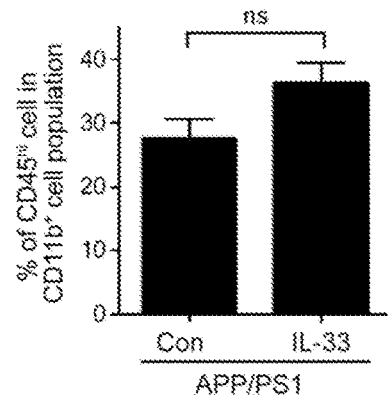

Both resident microglia and infiltrating monocytes are suggested to play phagocytic roles in clearing unwanted materials in neurodegeneration and brain injury. Subsets of CD11b$^+$ myeloid cells that exhibited increased Aβ phagocytic activity in IL-33-treated APP/PS1 mouse brains were examined. Data presented in FIGS. 24A-24G show that IL-33 does not increase the infiltration of phagocytic activity of peripheral monocytes in the brains of APP/PS1 mice. Resident microglia and infiltrated monocytes can be differentiated by low) (CD45$^{lo}$ and high (CD45$^{hi}$) CD45 expression, respectively. Most CD11b$^+$ myeloid cells in the WT mice were resident microglia, as characterized by the low CD45 expression (>90% CD45$^{lo}$; FIG. 24A). The APP/PS1 mice exhibited ~3.6-fold more infiltrating monocytes (CD11b$^+$CD45$^{hi}$ myeloid cells) compared with the WT mice (FIGS. 24A-24D). In the APP/PS1 mice, ~10% of CD11b$^+$ CD45$^{lo}$ resident microglia phagocytosed Aβ (FIGS. 6C-6D), and ~80% of CD11b$^+$CD45$^{hi}$ infiltrating monocytes took up the MeX04-labeled Aβ (FIGS. 6E-6F). IL-33 administration significantly increased Aβ phagocytic uptake by resident microglia by ~80%, whereas the percentage of Aβ-containing infiltrating monocytes remained relatively stable (FIGS. 6C-6F).

Example 7: IL-33/ST2 Signaling Mediates Microglial Phagocytic Activity

Primary microglial culture was generated by isolating microglia cells from adult ST2-wild-type and ST2-deficient mouse brains. The cultures were pre-incubated with IL-33 followed by exposure to fluorescent-labeled Aβ treatment. The ability of the microglia to uptake the Aβ was then evaluated by quantifying the fluorescence within the cells. The cells were then fixed with paraformaldehyde and immunostained with Iba1 antibody and Hoechst 34580. Wide-field fluorescence microscopy was performed by using an IN Cell Analyzer 6000 system (GE Healthcare) to examine the Aβ uptake. The differences in the amount of FAM-Aβ$_{1-42}$ uptake were compared between the control (Con) and IL-33-treated ST2$^{+/+}$ and ST2$^{-/-}$ cultures.

Figure 7:
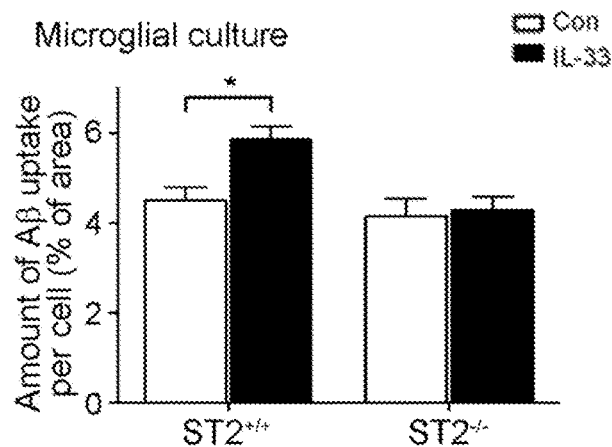
FIG. 7 shows that IL-33/ST2 signaling mediates microglial phagocytic activity. ST2-deficient microglia abolished the IL-33-stimulated Aβ uptake. The differences in the amount of FAM-$A\beta_{1-42}$ uptake were compared between the control (Con) and IL-33-treated $ST2^{+/+}$ and $ST2^{-/-}$ cultures. n=6 mice in 3 independent experiments per condition, *p<0.05, two-way ANOVA followed by the Bonferroni post hoc.
Figure 25A:
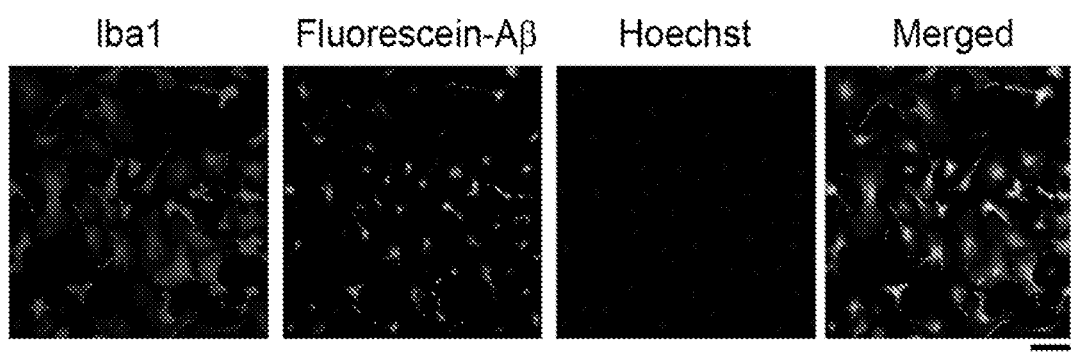
FIGS. 25A-25C show that IL-33 stimulates Aβ uptake in primary mouse CD11b$^+$ myeloid cells. Primary CD11b$^+$ myeloid cells were isolated from WT C57BL/6 mouse brains and cultured for 6-7 days in vitro. The cells were then stimulated with graded concentration of IL-33 for 20 h followed by fluorescein-Aβ$_{1-42}$ for 1 h. The cells were then fixed and analyzed by wide-field fluorescence microscopy.
Figure 25B:
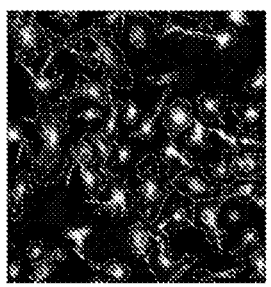
Figure 25C:
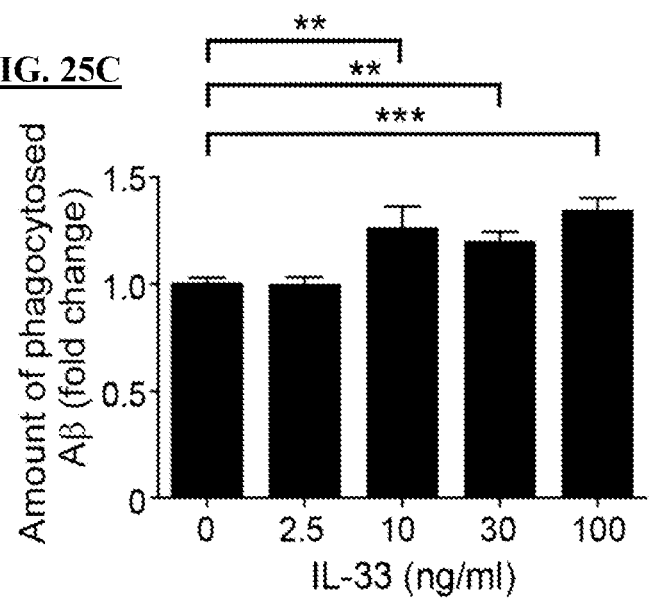

Data presented in FIG. 7 shows ST2-deficient microglia abolished the IL-33-stimulated Aβ uptake; however, IL-33 enhanced the uptake of fluorescence-labeled oligomeric Aβ$_{1-42}$ in cultured microglial cells in WT mice in a dose-dependent manner (FIG. 25C). Concordant with the prominent expression of ST2 in microglia (FIG. 26A), the downstream signaling molecules (p38 and ERK1/2 MAPKs) of ST2 receptors were activated in cultured microglia on IL-33 treatment (FIGS. 26B-26D). These results indicate that ST2 signaling in microglia mediates the IL-33 associated enhancement of Aβ phagocytosis in the brain of APP/PS1 mice.

Example 8: IL-33 Enhances the Degradation Activity of Aβ in APP/PS1 Mice

Soluble Aβ can be degraded by Aβ-degrading enzymes, including neprilysin and insulin-degrading enzyme. APP/PS1 mice (10-months-old) were i.p. administered with IL-33 for 2 days. Cortices were collected for Western blot analysis to determine the neprilysin (NEP) and insulin-degrading enzyme (IDE) expression.

Figure 8A:
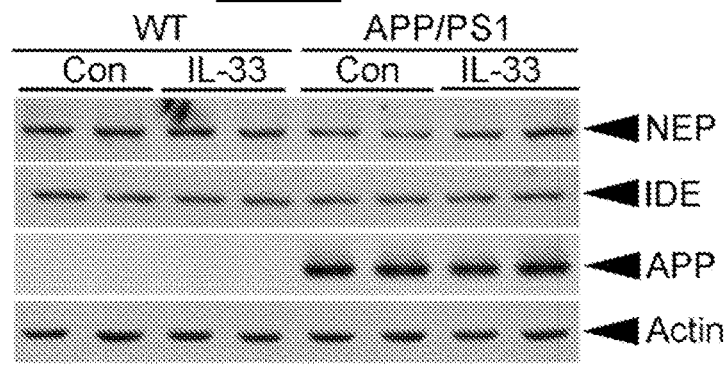
FIGS. 8A-8C show that IL-33 administration restores reduced neprilysin (NEP) expression in APP/PS1 mice. WT or APP/PS1 mice (~12 months old) were administered (i.p.) IL-33 or control vehicle (Con) for 2 days. Cortices were isolated for Western blot analysis.
Figure 8B:
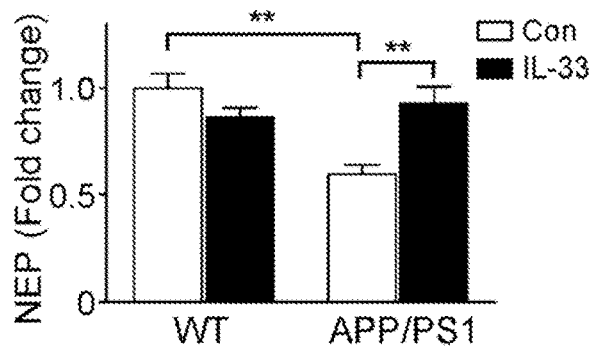
Figure 8C:
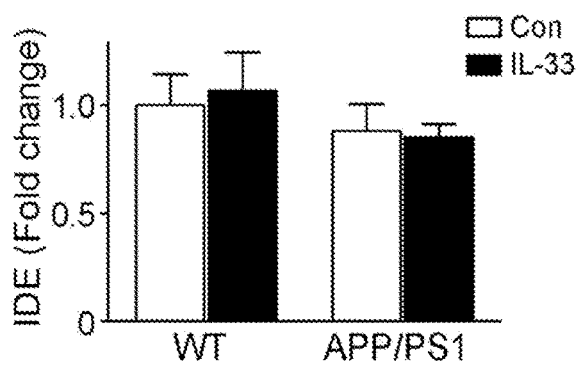

Data presented in FIGS. 8A-8C show that whereas reduced neprilysin expression was observed in the brains of APP/PS1 mice (FIG. 8A), IL-33 administration increased neprilysin (NEP) protein expression (FIG. 8B), but not insulin-degrading enzyme (IDS) expression (FIG. 8C), in APP/PS1 mice. Taken together, these data demonstrate that IL-33 administration mitigates the amyloid plaque pathology in APP/PS1 mice through the enhancement of Aβ clearance, probably by increasing neprilysin levels.

Example 9: Combinatorial Treatment of IL-33 and Memantine in Mouse Attenuates Aβ-Mediated Synaptic Impairment of Acute Hippocampal Slice To investigate whether co-treatment of IL-33 and memantine exerts synergistic effects to alleviate synaptic impairment during progression of AD, C57 mice were co-administered with 1 mg/kg/day memantine (via oral administration), and 50 ng/day IL-33 via (i.p. administration). Previously, it was determined that IL-33 administered a dose of at least 200 ng/day was required to rescue LTP impairment in APP/PS1 mice.

Figure 9:
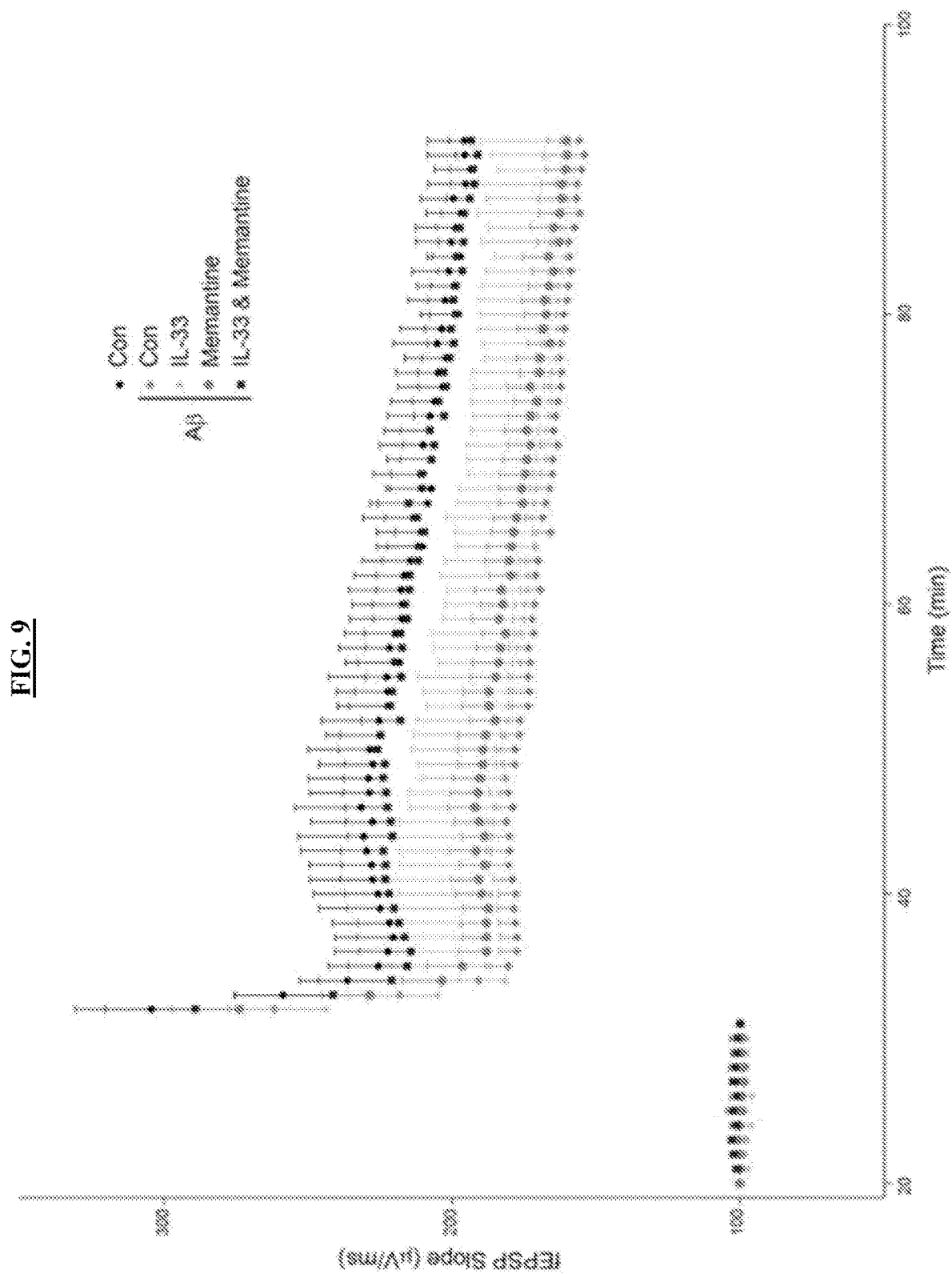
FIG. 9 shows that combination treatment of IL-33 and memantine rescues LTP impairment induced by Aβ. C57 mice were co-administered with 1 mg/kg/day memantine via oral administration and 50 ng/day IL-33 (a dosage that does not rescue LTP impairment in APP/PS1 mice) via i.p. Hippocampal slices of the mice with different administration paradigms were then subjected to Aβ treatment and the LTP induced by HFS was measured (Con: 3 brains, 4 slices; Con+Aβ: 3 brains, 6 slices; IL-33+Aβ: 1 brains, 2 slices; Memantine+Aβ: 3 brains, 6 slices; IL-33+Memantine+Aβ: 4 brains, 8 slices).
Figure 35A:
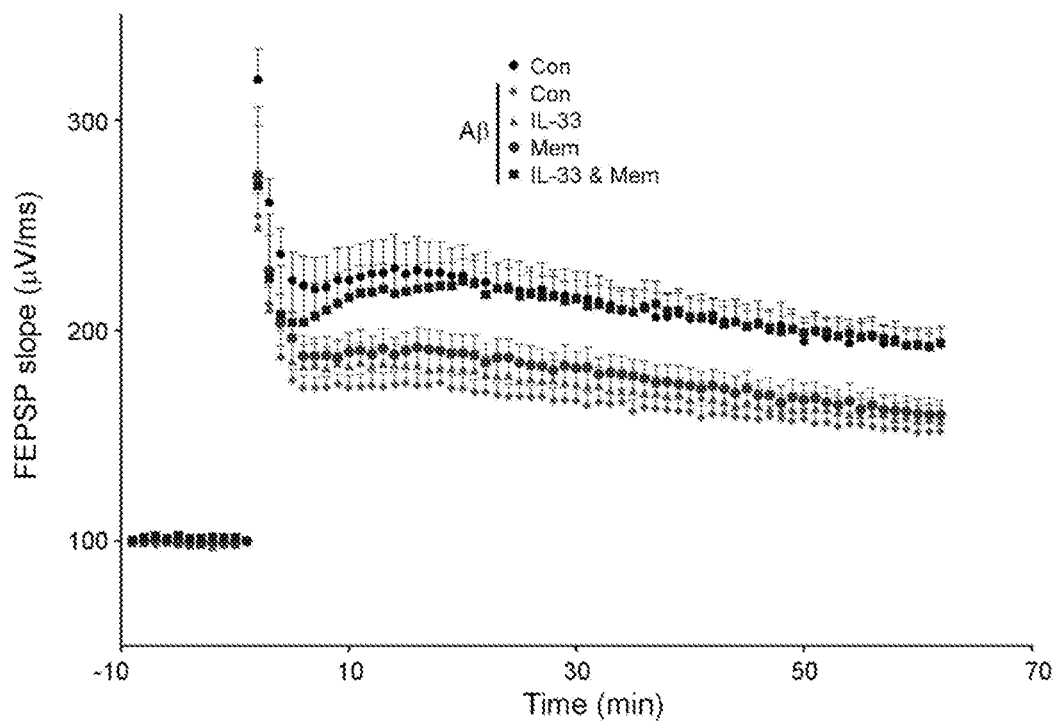
FIGS. 35A-35B show that combination treatment of IL-33 and memantine rescues LTP impairment induced by Aβ. C57 mice were co-administered with 1 mg/kg/day memantine (Mem) via oral delivery and 50 ng/day IL-33 (a dosage that does not rescue LTP impairment in APP/PS1 mice) via i.p injection. Hippocampal slices of the mice with different administration paradigms were then subjected to Aβ treatment, and the LTP induced by HFS was measured.
Figure 35B:
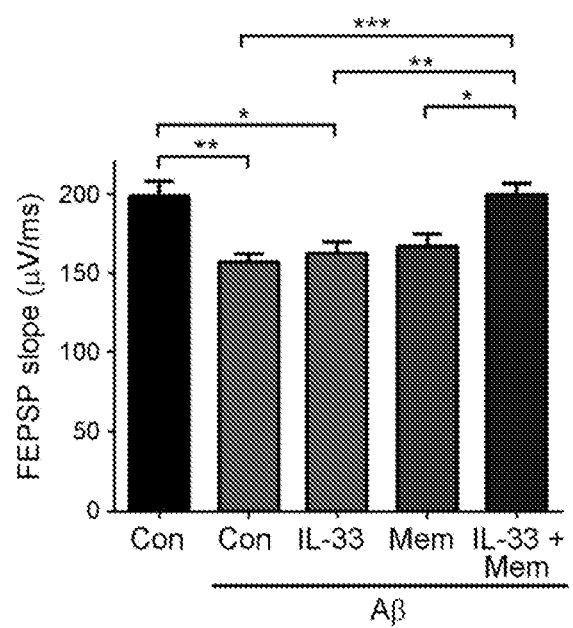

After 2 days of co-treatment, hippocampal slices were prepared from the treated mouse brain and subjected to LTP analysis. Specifically, the isolated hippocampal slices were rejuvenated in oxygenated buffer for 2 h and then incubated with 500 nM Aβ for 2 h before LTP stimulation. The results presented in FIG. 9 and FIGS. 35A-35B indicate that the IL-33 and memantine combination treatment had a synergistic effect in rescuing LTP impairment compared to treatment with memantine alone.

Example 10: IL-33 Modulates the Microglial Transcriptome Signature in APP/PS1 Mice WT and APP/PS1 mice (12-months-old) were i.p. injected with IL-33 or control vehicle (Con) for 2 days (n=2 per group). The total RNA of microglia from the mouse cortex was extracted and subjected to low-input RNA sequencing to identify transcriptome signatures.

Figure 10A:
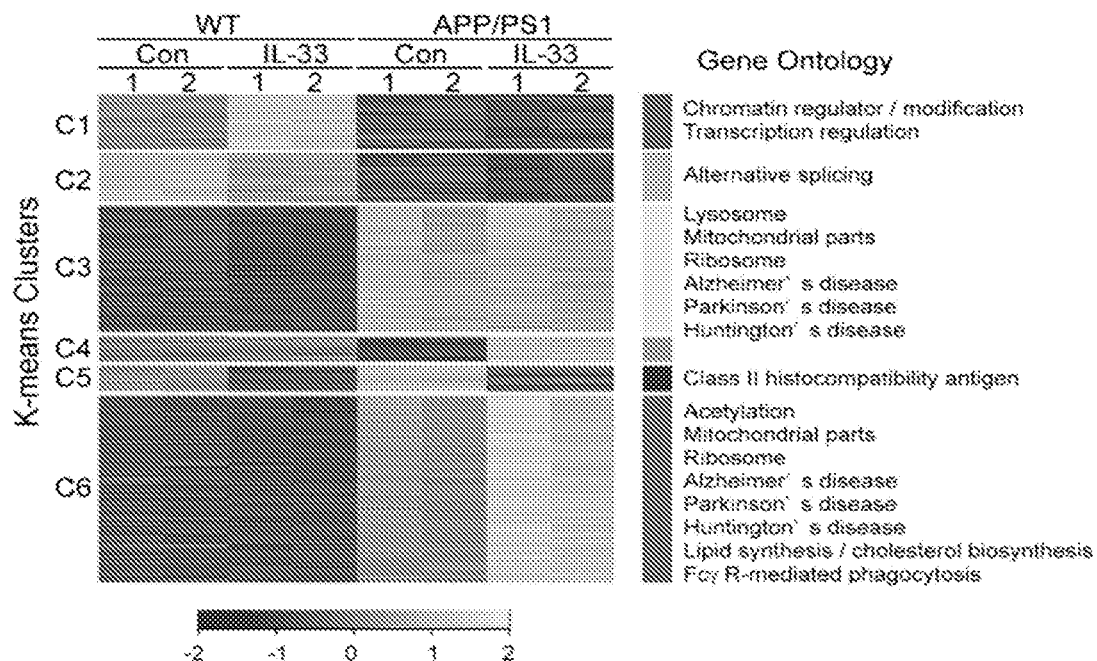
FIGS. 10A-10R show that IL-33 alters microglial gene expression in APP/PS1 mice. APP/PS1 mice were i.p. injected with IL-33 for 2 days.
Figure 10B:
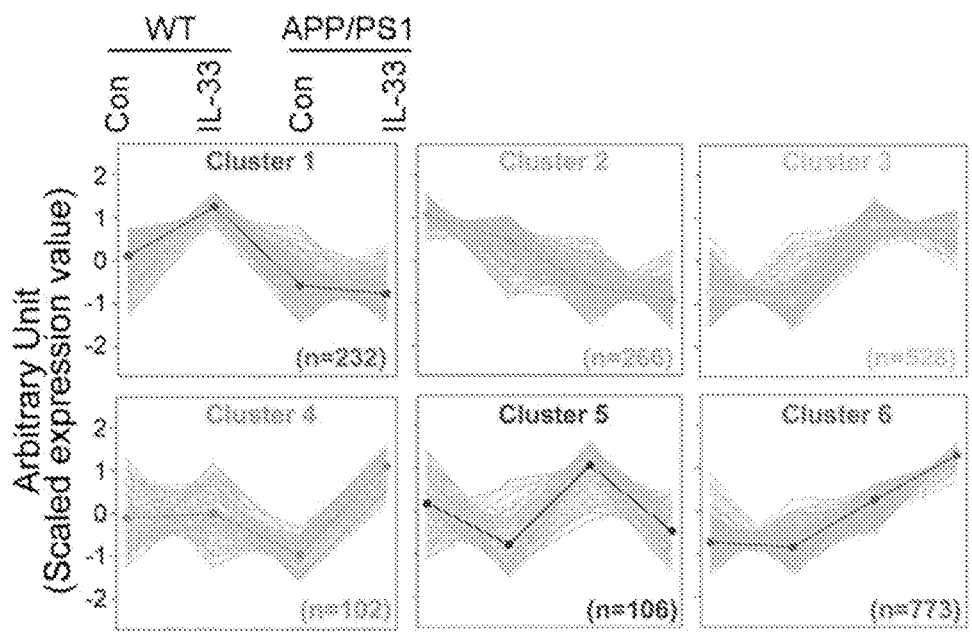
Figure 10P:
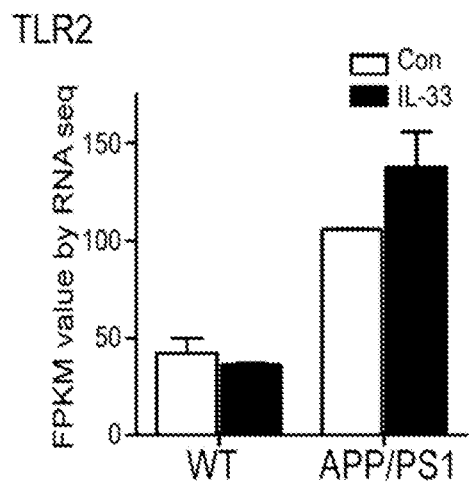
Figure 10Q:
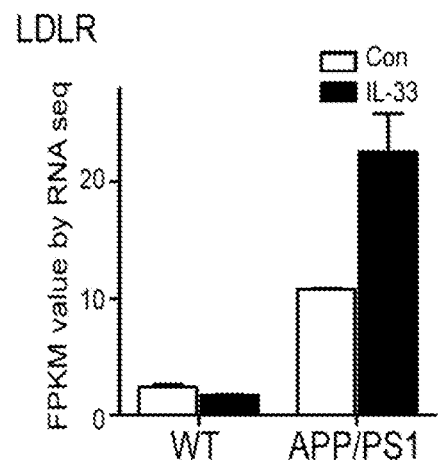
Figure 10R:
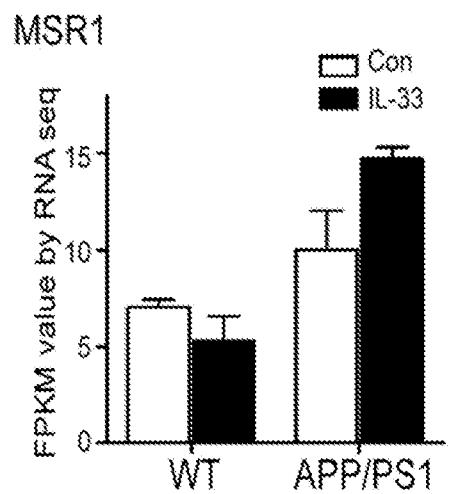

FIGS. 10A-10C show that IL-33 alters the microglial transcriptome signature in APP/PS1 mice. Corresponding networks of upregulated genes in each gene set were classified according to the STRING database. Results are indicated in FIGS. 10D-10O. The top six networks in response to IL-33 in microglia of APP/PS1 mice are shown: cholesterol homeostasis (FIGS. 10D and 10G); IL-6/JAK/STAT3 signaling (FIGS. 10E and 10H); IFN-α response (FIGS. 10F and 10I); IFN-γ response (FIGS. 10J and 10M); G2M phase of the cell cycle (FIGS. 10K and 10N); and TNF-α response (FIGS. 10L and 10O). The analysis also showed that IL-33 increases the transcription of Aβ receptors, specifically, Toll like receptor 2 (TLR2) (FIG. 10P), low density lipoprotein receptor (LDLR) (FIG. 10Q), and macrophage scavenger receptor 1 (MSR1) (FIG. 10R).

Example 11: Soluble ST2 Concentration Increases in MCI Patient Sera

Figure 11:
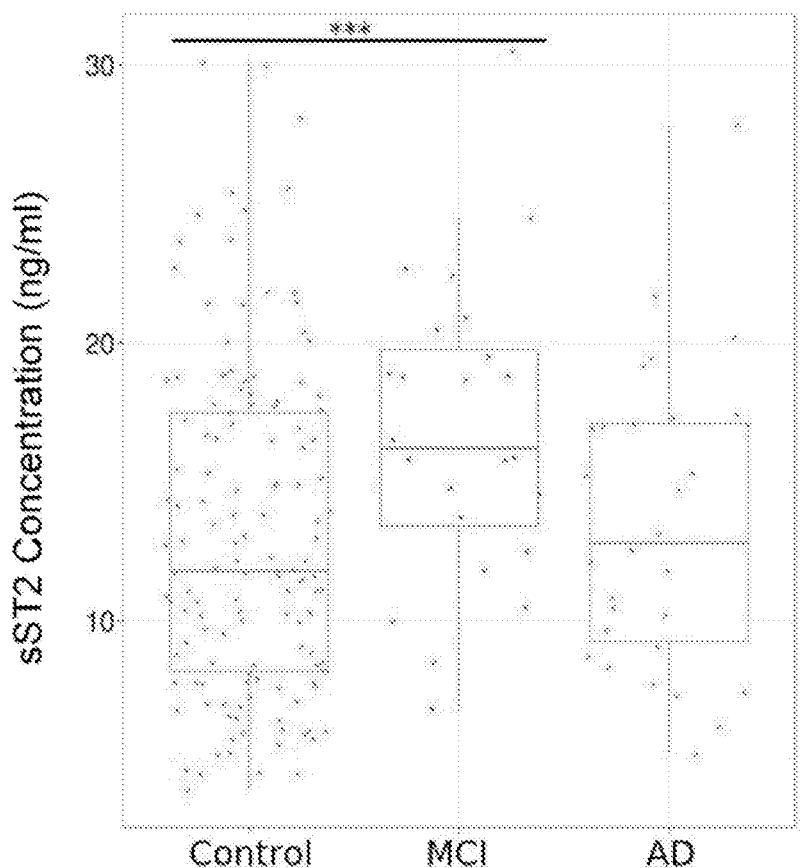
FIG. 11 is a boxplot showing soluble ST2 (sST2) levels in normal, MCI and AD patients. Soluble ST2 concentration of human serum was examined by ELISA. Con: n=137; MCI: n=24; AD: n=30; ***p-value from two-sample t-test <0.005.

Soluble ST2 (sST2) levels (ng/ml) were measured in serum obtained from patients with Alzheimer's disease (AD) and mild cognitive impairment (MCI), as well as healthy controls, using the Human ST2 ELISA kit (R&D systems). Results presented in FIG. 11 and FIG. 27A show increased levels of sST2 in sera from MCI patients compared to sera from AD patients and controls.

Figure 12:
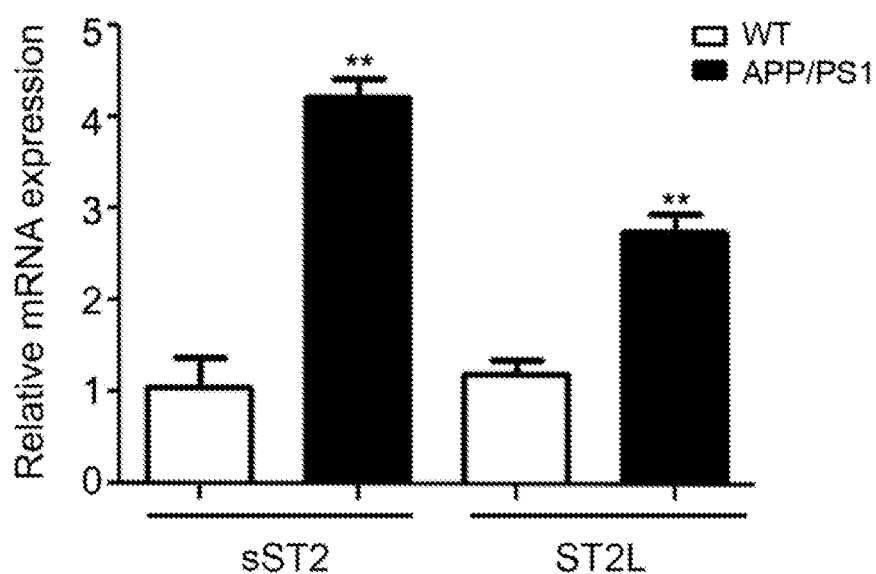
FIG. 12 shows that sST2 and ST2L mRNA expression increase in APP/PS1 mice. Transcript expression of soluble form (sST2) and membrane-anchored form (ST2L) in cortex of wild type (WT) and APP/PS1 mice (at 12 months old) were examined by quantitative real time PCR. The mRNA expression was normalized using WT. Data are presented as mean±SEM (n=3 mice/condition; **p<0.01, Student's t-test).

Example 12: Soluble ST2 and Membrane-Anchored ST2 mRNA Expression Increase in APP/PS1 Mice Cortices The mRNA expression of sST2 and the membrane-anchored form of ST2 (ST2L) in wild type and APP/PS1 mice mouse cortex (12-months-old) were examined by quantitative PCR. Data presented in FIG. 12 show that both sST2 and ST2L were elevated in the cortices of APP/PS1 mice.

Materials and Methods for Examples 13-21

Reagents.

Mouse recombinant IL-33 (mIL-33) (#580506) was obtained from BioLegend. Human recombinant IL-33 (hIL-33) (#581802) was obtained from BioLegend. sST2-Fc recombinant protein (1004-MR-050) and ST2/IL-1 R4 Quantikine ELISA Kit (DST200) were purchased from R&D Systems. Antibodies specific for IL-33 (clone Nessy-1, ab54385) and APP (clone DE2B4, ab11132) were purchased from Abcam; Iba1 antibody (019-19741) was from Wako; APC-conjugated antibody against CD11b (clone M1/70) and FITC-conjugated antibody against CD45 (clone 30-F11) were from eBioscience; CD68 antibody (FA-11) was from AbD Serotec; monoclonal 4G8 antibody (recognizes Aβ$_{17-24}$, SIG-39220) for immunohistochemistry and 6E10 antibody (recognizes A13$_{1-16}$; SIG-39320) for Western blot analysis were from Covance; P-p38 (#4511), p38 (#9212), P-ERK1/2 (#4377), and ERK1/2 (#9102) antibodies were from Cell Signaling Technology; actin antibody (clone AC-40; A4700) was from Sigma-Aldrich. Fluorescein-Beta-Amyloid (1-42) (A-1119-1) was from rPeptide; methoxy-X04 (#4920) was from Tocris Bioscience; DAB was from DAKO, Hoechst 34580 (H21486), human Aβ$_{x-40}$ (KHB3481), and Aβ$_{x-42}$ (KHB3441) commercial ELISA kits (ENZ-KIT140-0001), and Alexa Fluor secondary antibodies were from Life Technologies; and the histamine ELISA kit was obtained from Enzo.

Oligomeric Fluorescein Aβ$_{1-42}$ Preparation.

Monomeric Aβ$_{1-42}$ was dissolved in dry DMSO and diluted in ice-cold phenol red-free F-12 medium to a final concentration of 100 μM. The fluorescein-Aβ$_{1-42}$ solution was incubated at 4° C. for 24 h and then centrifuged at 14,000×g for 10 min. The supernatant was frozen in liquid nitrogen as aliquots and stored at −20° C. for up to 1 month.

Human Subjects.

All cases involved Han Chinese patients. Clinical diagnosis was established according to the National Institute of Neurological and Communicative Disorders and Stroke/Alzheimer's Disease and Related Disorders Association criteria. The human mild cognitive impairment (MCI) cases were gathered from outpatient or inpatient clinics at the Department of Neurology, Second Affiliated Hospital of the Zhejiang University School of Medicine, and the control group without dementia was recruited from the Health Examination Center from 2014-2015.

Data on age, sex, education, medical history, and family history were also recorded (FIG. 27). The sera of 17 healthy controls (NC) and 18 MCI patients of mixed sex were collected. The NC and MCI patients recruited were >60 years old. Patients with other neurological or psychiatric disorders or clinically significant medical conditions were excluded. No patient had a history of head trauma, alcohol or drug abuse. This study was approved by the Institutional Ethics Committees of the Second Affiliated Hospital of the Zhejiang University School of Medicine and The Hong Kong University of Science and Technology. Informed consent for participation in this study was obtained either directly or from a legal guardian.

Mice.

The APP/PS1 double-transgenic mice, which were generated by incorporating a human/mouse APP construct bearing the Swedish double mutation and the exon-9-deleted PSEN1 mutation (APPswe+PSEN1/dE9), were obtained from the Jackson Laboratory (B6C3-Tg[APPswe, PSEN1dE9]85Dbo/J). The generation of 5XFAD mice overexpressing the K670N/M671L (Swedish), I716V (Florida), and V717I (London) mutations in human APP (695) as well as M146L and L286V mutations in human PS1 have been described previously (Oakley, H., et al. *J. Neurosci.* 26(40): 10129-10140 (2006)). The 5XFAD mice were kindly provided by Dr. Sookja Kim Chung (The University of Hong Kong). St2$^{-/-}$ mice were obtained from Dr. Andrew McKenzie (Xu, D., et al. *Proc. Natl. Acad. Sci. USA* 105(31): 10913-10918 (2008)). Genotypes were confirmed by PCR analysis of tail or ear biopsies. Wild type C57BL/6 mice were obtained from Jackson Laboratory.

All mice were housed in the Animal and Plant Care Facility of The Hong Kong University of Science and Technology (HKUST). All animal experiments were approved by the Animal Ethics Committee of HKUST. Mice of the same sex were housed 4 per cage with a 12-h light/dark cycle and food and water ad libitum. All in vivo experiments were performed on sex- and age-matched groups. Mice of both genders were used for experiments. The mice were randomly assigned to the experimental conditions. Sample sizes were primarily chosen on the basis of experience with similar types of experiments. All the animal experiments were conducted in the light phase.

In Vivo Experiments.

Figure 13:
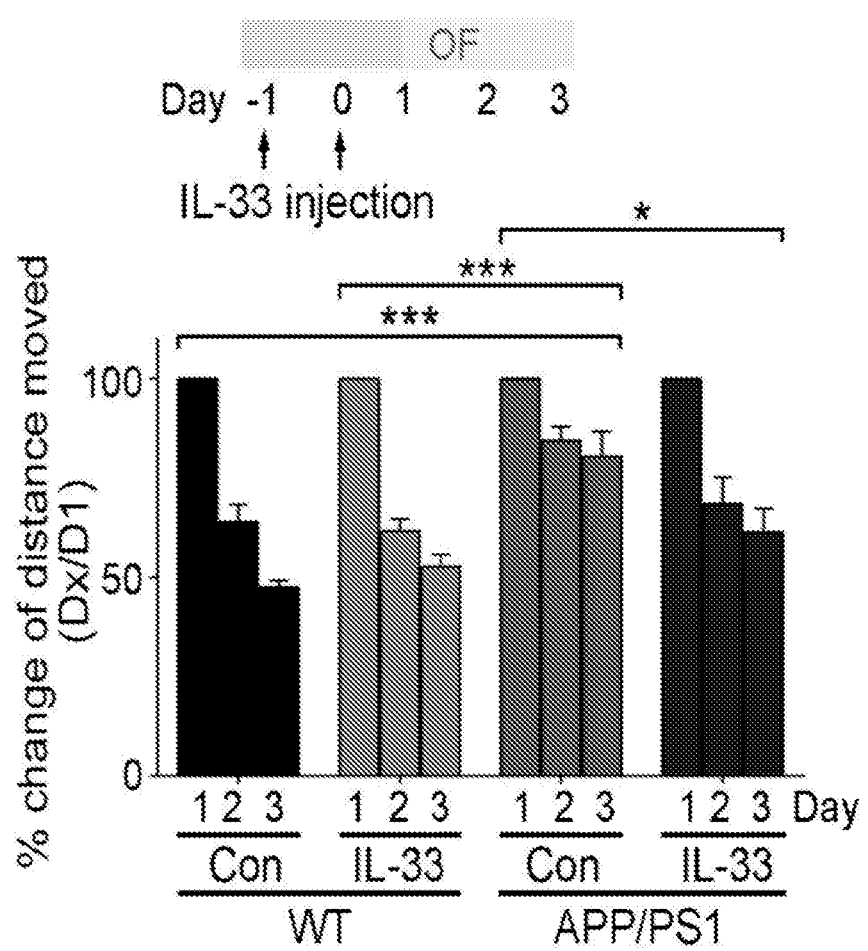
FIG. 13 shows that IL-33-treated APP/PS1 mice (14 months old; i.p. injected) exhibit improved habituation in the exploratory open field (OF) test. The upper panel shows the timeline of IL-33 administration and the OF test. The lower panel shows the percentage change in distance traveled relative to the distance traveled on the first day of training (n=11-13 mice/group. Data are mean±SEM. *p<0.05; ***p<0.001, two-way repeated-measures ANOVA).

Mouse recombinant IL-33 (200 ng per mouse) was injected i.p. into 6-25-month-old mice. For studies of amyloid plaque load, microglial phagocytosis of Aβ, mRNA expression, and LTP, mice were injected with IL-33 for 2 consecutive days. The field excitatory postsynaptic potentials were recorded using a MED64 multichannel recording system (Panasonic International Inc.). For behavioral tests, mice were injected i.p. with IL-33 as indicated in FIG. 13 and FIG. 14A. Open field test and contextual fear conditioning were conducted as previously described (Sananbenesi, F., et al., *Nat. Neurosci.* 10(8):1012-1019 (2007); Ip, FC., et al., *Neuropsychopharmacology* 40(8):1877-1887 (2015)). Soluble ST2 (sST2) was delivered into APP/PS1 mice via mini-osmotic pumps (model 1004, Alzet) at 0.11 µL/h. The mini-osmotic pumps were adjusted intracerebroventricularly in the right hemisphere. The pumps were loaded with mouse recombinant sST2 protein (240 ng per pump; 10 µg/mL) or with vehicle in artificial cerebral spinal fluid (aCSF; 119 mM NaCl, 2.5 mM KCl, 2.5 mM $CaCl_2.2H_2O$, 1 mM $NaH_2PO_4.2H_2O$, 1.3 mM $MgCl_2.6H_2O$, 26.2 mM $NaHCO_3$, 11 mM d-glucose). After 2 days of sST2 delivery, IL-33 was administered i.p. to mice for 2 more days. At the end of the treatment, the mice were sacrificed and the brains were fixed with 4% paraformaldehyde.

LTP.

Briefly, mice were sacrificed, and whole brains were immediately resected and soaked in ice-cold aCSF supplemented in 95% $O_2$/5% $CO_2$. Brain slices (300 µm) were then prepared using a vibratome (HM650V, Thermo) and soaked in oxygenated aCSF for 2 h at 32° C. The mouse hippocampal slices were placed on a pre-coated polyethylenimine (Sigma-Aldrich) on a MED-P210A probe (Panasonic International Inc.) fabricated with 8×8 electrode arrays (20×20 µm, indium tin oxide and platinum black) with a 100-µm inter-electrode distance. Electrodes were manually placed at the CA3-CA1 region under a microscope (MIC-D, Olympus). Each slice was submerged in and superfused with oxygenated aCSF at 1.3-1.5 mL/min. Field excitatory postsynaptic potentials (fEPSPs) were recorded from the dendritic layer of CA1 neurons by selecting an electrode in the Schaffer collateral pathway as the stimulating electrode. On the basis of the stimulus-response curve, a stimulation intensity that evoked a fEPSP with 30-40% of the maximum response was selected. LTP was induced by 3 trains of high-frequency stimulation (100 Hz for 1 s delivered 30 s apart). The field potential response after the tetanus was recorded for 60 min. The magnitude of LTP was quantified as the percentage change in the average slope of the fEPSP over 60 min after LTP induction.

Open Field Test.

The locomotor activity of the mice in the open field test was recorded and tracked by using the photobeam activity system and software (San Diego Instruments). In brief, experimental mice were placed in the center of an open-top chamber (16×16×15 inches) with an array of photobeams around the periphery. The mice were allowed to explore the chamber for 15 min each day for 3 consecutive days. Locomotor activity in the 3 training trials was recorded by the photobeams, and the distance moved was subsequently determined. The chamber was cleaned with 70% ethanol after each trial.

Contextual Fear Conditioning.

On the day of training, the mice were allowed to explore in an enclosed training chamber with floor wired to an electric shock generator for 180 s. The mice were then exposed to a pure tone for 30 s, followed by a 2 s foot shock (0.8 mA). At 60 s after the delivery of the second shock, the mice were returned to their home cages. The fear response (freezing) was assessed 1 and 7 days after the electric shock. The mice were re-exposed in the original chamber for 5 min and the time of freezing was measured by the Contextual NIR Video Fear Conditioning System (Med Associates Inc.).

Immunohistochemistry.

Coronal cryosections (20 µm) of perfused mouse brains were used for immunohistochemistry. For 4G8 immunostaining, antigen retrieval was performed by microwave heating the sections in sodium citrate buffer (10 mM trisodium citrate, 0.5% Tween-20 in $H_2O$, pH 6.0) for 10 min followed by incubation with 3% $H_2O_2$ in $H_2O$ for 5 min to inhibit endogenous peroxidase activity. The sections were blocked with 2% goat serum in Tris-buffered saline for 20 min and then labeled with 4G8 antibody (dilution 1:500) in blocking buffer overnight at 4° C. The sections were then labeled with a Dako HRP-linked goat anti-mouse/rabbit IgG antibody for 50 min at room temperature and developed with a Dako DAB chromogen kit. Imaging was performed using a Leica DM6000 B compound microscope system. The area of Aβ plaques in the cortex of the brain sections was analyzed by the "Analyze Particles" function of Image J (National Institutes of Health). The region of cortex used for amyloid plaque analysis was above the hippocampus. Three brain sections per mouse (~200-300 μm apart) were analyzed, and the average percentage of cortical area occupied by amyloid plaques was calculated.

To examine the co-localization of amyloid plaques and microglia, the brain sections were blocked with 1% bovine serum albumin, 4% goat serum, and 0.4% Triton X-100 in DPBS for 30 min at room temperature and then incubated with Iba1 (1:500 dilution) and 4G8 (1:1000 dilution) antibodies overnight at 4° C. Imaging was performed using a Leica TCS SP8 confocal system.

To determine the blood-brain barrier penetrability of IL-33, 11-month-old APP/PS1 mice were i.p. injected with IL-33 (200 ng) in DPBS or DPBS alone. Mouse cortices and sera were collected for IL-33 ELISA.

Aβ Extraction, Western Blot Analysis, and ELISA.

Aβ was sequentially extracted from the soluble and insoluble fractions of the mouse cortex. Frozen brain tissues were lysed in indicated lysis buffers with various protease inhibitors. Briefly, the mouse cortex was homogenized in buffer containing 250 mM sucrose, 20 mM Tris-HCl (pH 7.4), 1 mM EDTA, 1 mM EGTA, and protease inhibitor cocktail (Sigma-Aldrich) or in radioimmunoprecipitation assay buffer. Densitometric quantification of protein band intensity from Western blot analysis was performed using the NIH ImageJ program. Soluble Aβ was sequentially extracted by diethylamine (soluble) followed by formic acid (insoluble). Levels of soluble and insoluble Aβ were determined using Western blot analysis. Soluble $Aβ_{x-40}$ and $Aβ_{x-42}$ were analyzed by ELISA.

Isolation of Mouse Microglia.

Adult mice were anaesthetized and perfused with ice-cold DPBS. The isolated cortices were cut into small pieces and dissociated enzymatically and mechanically using a papain-based neural dissociation kit (130-092-634, Miltenyi Biotec) with gentleMACS dissociator system (Miltenyi Biotec) according to the manufacturer's instructions. Percoll gradient (30%, Sigma-Aldrich) was used to remove myelin. The resultant mononuclear cell suspensions were used for flow cytometry analysis or setting up microglial cultures. The purity of microglia/infiltrating monocytes isolation was routinely >90% as determined by fluorescence staining for CD11b and flow cytometry analysis.

Analysis of Microglial Phagocytosis of Aβ.

For in vivo analysis, the experiment was performed as described (Zhang, G X, et al., *Exp. Mol. Pathol.* 73(1):35-45 (2002)). APP/PS1 or WT mice (17-months-old) were i.p. injected with IL-33 in PBS or PBS alone daily for 2 consecutive days. On the following day, the mice were i.p. injected with methoxy-X04 (10 mg/kg). The mice were deeply anesthetized 3 h after methoxy-X04 injection and perfused in the left ventricle with ice-cold PBS. Isolated mononuclear cell suspensions from the mouse brain cortex were then incubated with a mouse FcR blocking reagent (Miltenyi Biotec) and labeled with APC-conjugated mouse CD11b (1:100 dilution) and FITC-conjugated CD45 (1:100 dilution) antibodies and analyzed by a Becton Dickinson FACSAria IIIu flow cytometer. Myeloid cells were identified as $CD11b^+$ cells and were further classified as microglia or infiltrating monocytes by low)($CD11b^+CD45^{lo}$ and high ($CD11b^+CD45^{hi}$) CD45 expression, respectively.

For in vitro microglial phagocytosis assay, microglia cells were prepared from $St2^{+/+}$ or $St2^{-/-}$ mice (1.5-2-months-old) and cultured for 6-7 days in vitro. The cells were then pretreated with IL-33 for 20 h followed by fluorescein-$Aβ_{1-42}$ (2 μM) for 1 h. The cells were then fixed with paraformaldehyde and immunostained with Iba1 antibody and Hoechst 34580. Wide-field fluorescence microscopy was performed using an IN Cell Analyzer 6000 system (GE Healthcare). Images were acquired at 16 corresponding positions assigned by the software in each well. Intensity segmentation was applied to each channel using the same thresholding criteria across different samples. The boundaries of microglia were determined according to $Iba1^+$ labeling intensity, and fluorescein-$Aβ_{1-42}$ in each $Iba1^+$ cell was quantified. The area of phagocytosed fluorescein-$Aβ_{1-42}$ was divided by the corresponding cell area to obtain the relative area of fluorescein-$Aβ_{1-42}$ in a given cell.

Droplet Digital PCR (ddPCR) and RT-qPCR.

For ddPCR, RNA from mouse cortices was extracted using TRIzol (Invitrogen) and RNeasy Mini kit (Qiagen) and was quantified using a BioDrop μLITE micro-volume spectrophotometer (BioDrop), and equivalent amounts of RNA were reverse-transcribed using a PrimeScript RT-PCR Kit (TaKaRa). ddPCR was performed according to the manufacturer's protocol (Bio-Rad). The copy numbers for samples were averaged across duplicates. The copy numbers of target genes were normalized to that of GAPDH or β-actin. For RT-qPCR, cDNA after RT was pre-amplified using TaqMan PreAmp Master Mix (Invitrogen). The PCR amplification and real-time detection of PCR products were performed using TaqMan gene expression assay (Applied Biosystems) and Premix Ex Taq qPCR assay (TaKaRa). PCRs were conducted in a total volume of 20 μL containing 2 μL pre-amplified product. The mRNA expression values were normalized to the level of CD11b. The following TaqMan probes were used: NLRP3 (Mm00840904_m1), IL-1β (Mm01336189_m1), IL-6 (Mm00446190_m1), IL-13 (Mm00434204_m1), TGFβ (Mm01178820_m1), GAPDH (Mm99999915_g1), β-actin (Mm02619580_g1), ST2 total (Mm00516117_m1), Fizz1 (Mm00445109_m1), Arg1 (Mm00475988_m1), and CD11b (Mm00434455_m1).

Statistical Analysis.

The investigators who performed the electrophysiological, immunohistochemical, RNA expression, and flow cytometry analyses and the behavioral tests were blinded to the genotypes of the mice and treatment conditions. All data are expressed as arithmetic mean±SEM, except human sST2 serum level. Statistical analyses were performed by using GraphPad Prism version 6.0. The significance of differences was assessed by unpaired Student's t-test, or one- or two-way ANOVA followed by the Bonferroni post hoc test as indicated. The level of significance was set at $p<0.05$. Soluble ST2 levels were recorded for NC subjects and MCI patients, with data analyses performed using R (version 3.2.2). The Shapiro-Wilk test was used to assess normality of the continuous measurements. Statistical comparisons of ST2 levels in the two subject groups were compared using a two-sample t-test.

Example 13: IL-33-Treated APP/PS1 Mice Exhibit Improved Habituation in the 3-Day Exploratory Open Field (OF) Test In the exploratory open field (OF) test, the vehicle-injected and IL-33 injected WT mice exhibited similar habituation ability in novel testing environments during the 3-day training course. Data presented in FIG. 13 shows that the APP/PS1 mice exhibited slower habituation to the testing environment than the WT mice; however, the IL-33-treated APP/PS1 mice showed significantly improved habituation to the testing environment.

Example 14: IL-33 Treatment Reverses Contextual Memory Deficits in APP/PS1 Mice The memory formation and retrieval abilities of the IL-33-treated APP/PS1 mice were assessed using the contextual fear-conditioning (FC) test by evaluating the freezing response of the mice at 1 day and 7 days after the administration of electric shock (FIGS. 14A-14D). The mice of different experimental groups did not exhibit any significant difference in freezing response immediately after electric shock (FIG. 14B). Compared with the WT mice, the APP/PS1 mice exhibited reduced freezing behavior at 1 day and 7 days after the electric shock, indicating an impaired contextual retrieval of fear memory (FIGS. 14C-14D). Whereas the IL-33-treated APP/PS1 mice did not exhibit an improvement in freezing performance 1 day after the electric shock (FIG. 14C), IL-33 treatment was able to restore the impaired freezing response of the APP/PS1 mice at 7 days after the electric shock (FIG. 14D).

Figure 15A:
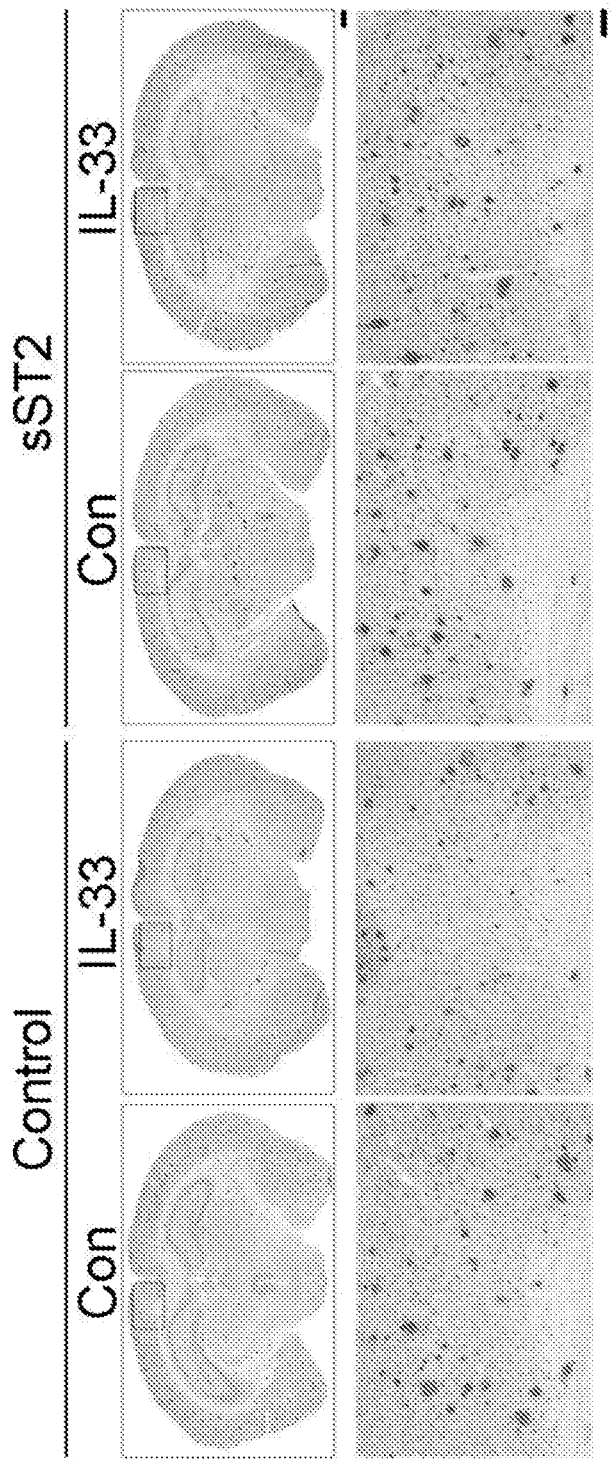
FIGS. 15A-15B show that at two days after IL-33 treatment, 4G8-labeled amyloid plaques are significantly reduced in the cortices of 12-month-old APP/PS1 mice.
Figure 15B:
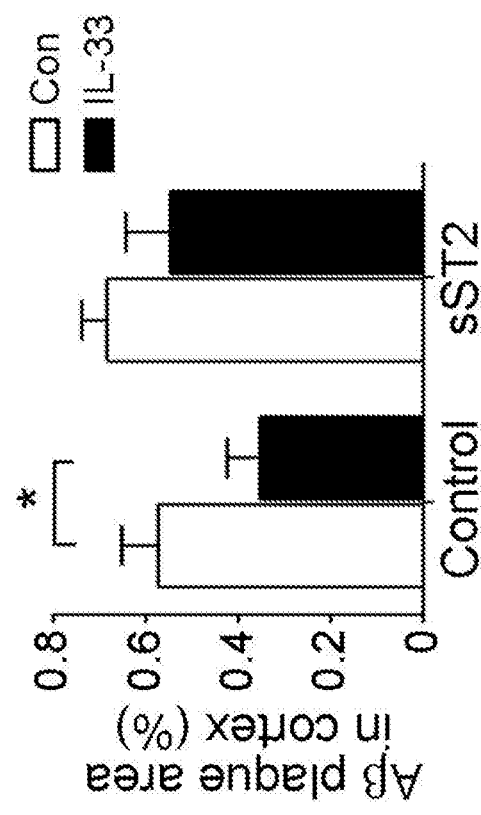

Example 15: IL-33 Treatment Ameliorated Amyloid Plaque Pathology in APP/PS1 Mice At two days after IL-33 treatment, the 4G8-labeled amyloid plaques were significantly reduced in the cortices of 12-month-old APP/PS1 mice (FIG. 15A-15B). Importantly, intracerebroventricular administration of sST2 abolished the IL-33-mediated reduction of 4G8-stained amyloid plaques in the APP/PS1 mice (FIGS. 15A-15B), demonstrating the specificity of the central activation of myeloid cells of IL-33/ST2 signaling in ameliorating the cerebral amyloid pathology. IL-33 administration for two days also reduced 4G8-stained amyloid plaques in 5XFAD mice, another transgenic mouse model (FIGS. 22A-22B).

Example 16: IL-33 Increases CD68 Expression in Aβ Plaques

CD68, a transmembrane glycoprotein of the lysosomal/endosomal-associated membrane glycoprotein family, acts as a scavenger receptor for debris clearance. In APP/PS1 mice, the clusters of Iba1$^+$ myeloid cells surrounding amyloid plaques exhibited diffuse CD68 distribution (FIG. 16A). IL-33 administration increased CD68 expression in Iba1$^+$ myeloid cells that were in close contact with amyloid plaques (FIG. 16B). These findings suggest that IL-33 administration increases phagocytic Aβ uptake by myeloid cells.

Example 17: IL-33 Drives Microglia to an Alternative Activation State in APP/PS1 Mice Inflammatory responses in the brain play a significant role in AD pathology. Microglial polarization is associated with the immune response in the CNS. The mRNA expression of Arg1 and Fizz1, which are associated with anti-inflammatory action, was significantly increased in CD11b$^+$ myeloid cells isolated from both WT and APP/PS1 mouse brains after IL-33 administration (FIGS. 17A-17B). These results suggest that IL-33 drives microglia/macrophages in the APP/PS1 mouse brains toward an alternative activation phenotype, which may contribute to neuroprotective functions.

Example 18: IL-33 Suppresses Proinflammatory Genes in APP/PS1 Mice

Figure 18A:
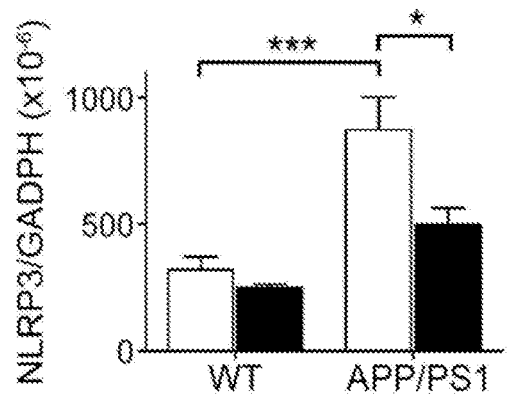
FIGS. 18A-18C show that IL-33 suppresses proinflammatory genes in APP/PS1 mice. APP/PS1 mice were i.p. injected with IL-33 for 2 days. Shown is quantitative ddPCR analysis of NLRP3 (FIG. 18A), IL-1β (FIG. 18B), and IL-6 (FIG. 18C) in the cortices of 12-month-old APP/PS1 mice. WT/Con, n=5 mice; WT/IL-33, n=3 mice; APP/PS1/Con, n=5 mice; APP/PS1/IL-33, n=4 mice. *p<0.05; p<0.01; *p<0.001, two-way ANOVA with Bonferroni post hoc test. All data are mean±SEM.
Figure 18B:
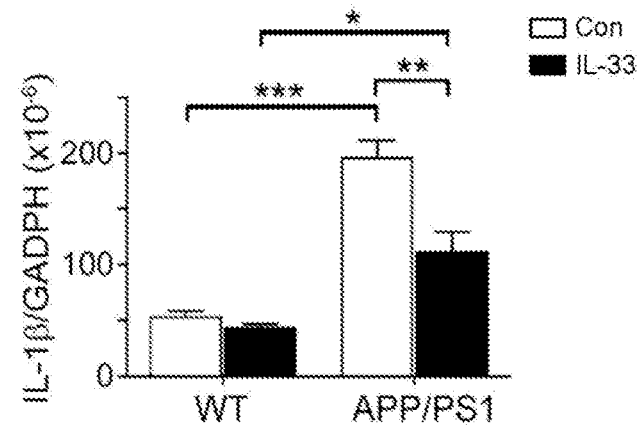
Figure 18C:
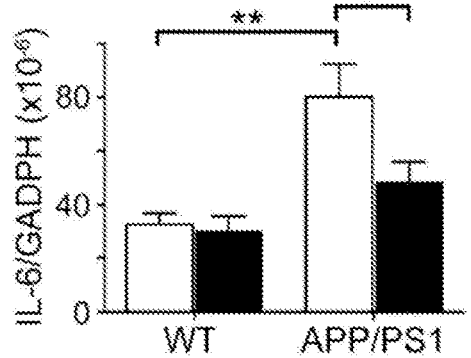

IL-33 can ameliorate global inflammation in the brain cortices of APP/PS1 mice. In the APP/PS1 mice, proinflammatory genes including IL-1β, IL-6, and NLRP3 (NOD-like receptor family, pyrin domain-containing 3, a key component in the inflammasome cascade) were significantly in the brain cortex (FIGS. 18A-18C). IL-33 administration suppressed the increased expression of these proinflammatory genes (FIGS. 18A-18C). These results suggest that IL-33 regulates inflammatory responses in the APP/PS1 mouse brain.

Figure 19A:
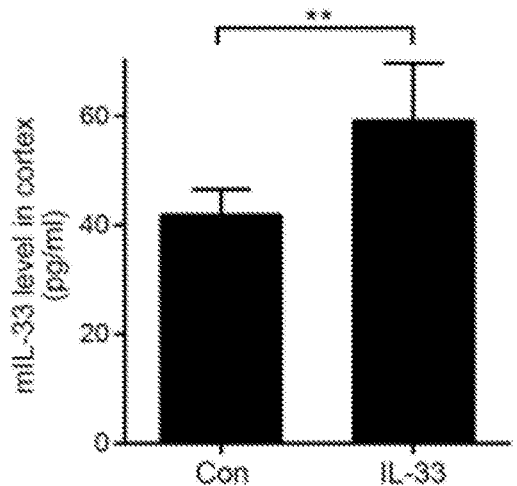
FIGS. 19A-19B show increased IL-33 levels in the cortices of APP/PS1 mice following i.p. administration of IL-33. APP/PS1 mice (11-months-old) were i.p. injected with IL-33 (200 ng) for 30 min. IL-33 levels in the cortices (FIG. 19A) and plasma (FIG. 19B) were measured by ELISA. Data are mean±SEM, n=4-5 mice/group. **p<0.01; Student's t-test.
Figure 19B:
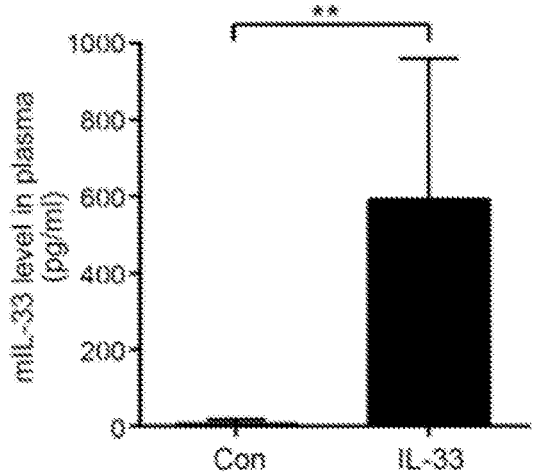

Example 19: IL-33 Reaches the Brain within 30 Minutes of Intraperitoneal Injection in APP/PS1 Mice APP/PS1 mice (11-months-old) were i.p. injected with mouse IL-33 (200 ng) for 30 minutes. IL-33 levels in the cortices (FIG. 19A) and plasma (FIG. 19B) were measured by ELISA. IL-33 reached the brain within 30 minutes after i.p. injection (FIG. 19A), consistent with earlier findings of a compromised blood-brain barrier in both APP/PS1 mice and patients with AD.

Example 20: IL-33 does not Affect Plasma Histamine Levels in APP/PS1 Mice

WT and APP/PS1 mice (8-months-old) were i.p. injected with mouse IL-33 (200 ng) or vehicle control for two consecutive days. The plasma histamine level was determined by ELISA. At the concentration used (200 ng i.p. daily for 2 days), IL-33 did not affect the plasma histamine levels in either WT or APP/PS1 mice (FIG. 20).

Example 21: IL-33 Reduces the Soluble Aβ Content in APP/PS1 Mice

APP/PS1 mice (25-months-old) were i.p. injected with IL-33 (200 ng) three times for 7 days. Results of a Western blot analysis, shown in FIG. 21, demonstrate that IL-33 injection reduced the amounts of soluble Aβ in the cortices of 25-month-old APP/PS1 mice.

Example 22: Administration Route of mIL-33 in APP/PS1 Mice

Materials and Methods.

APP/PS1 mice (8-9.5-months-old) were injected with IL-33 via either i.p. injection (200 ng in 300 µl/mouse/day) or subcutaneous injection (s.c.; 200 ng in 500 µl/mouse/day). To enhance the absorption efficiency of IL-33 via s.c. injection, IL-33 was administered at 3 sites for each injection (the lower back and two sides of shoulder). After two consecutive days of injection, half of the mouse brain was subjected to long-term potentiation (LTP) analysis at Schaffer collateral-CA1 synapses in the hippocampus. In brief, the mouse hippocampal slices were placed on a MED-P210A probe (Panasonic International Inc.) fabricated with 8×8 electrode arrays. Electrodes were manually placed at the CA3-CA1 region, and field excitatory postsynaptic potentials (fEPSPs) were recorded from the dendritic layer of CA1 neurons. LTP was induced by 3 trains of high-frequency stimulation (100 Hz for 1 s delivered 30 s apart). The field potential response after the tetanus was recorded for 60 min. The other half of the mouse cortex was used for examining the levels of Aβ. Aβ was sequentially extracted from the soluble and insoluble fractions of the mouse cortex using diethylamine and formic acid, respectively.

Results.

Figure 29B:
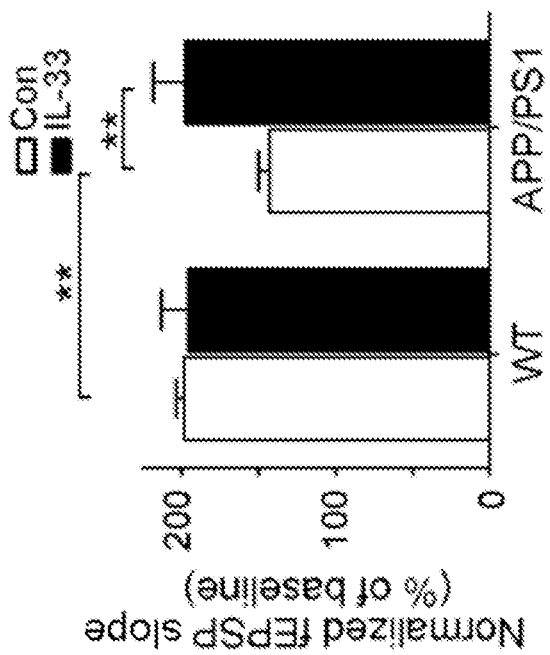
FIGS. 29A-29B show that s.c. administration of IL-33 reversed LTP impairment in APP/PS1 mice. Wild-type (WT) and APP/PS1 mice were S.C.
Figure 29A:
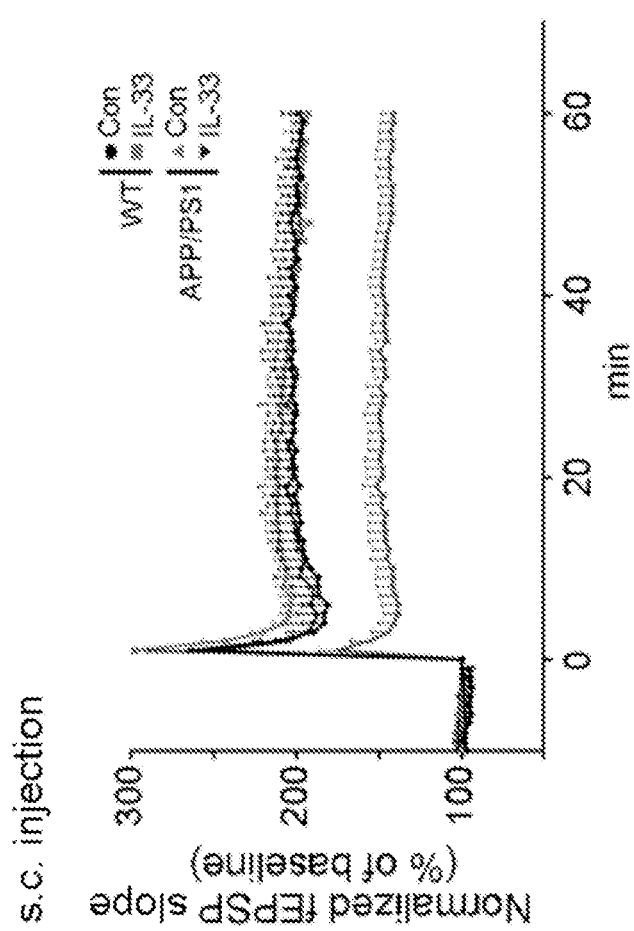

Data show that s.c. administration of IL-33 ameliorated the amyloid pathology (FIGS. 28A-28B) and rescued the synaptic impairment in APP/PS1 mice (FIGS. 29A-29B).

Example 23: Durability of IL-33 in APP/PS1 Mice

Materials and Methods.

Figure 30:
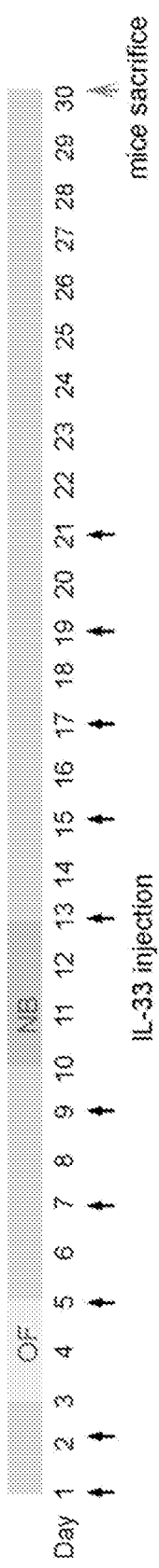
FIG. 30 is a timeline of IL-33 administration and behavioral tests, the results of which are shown in FIGS. 31-33. IL-33 injection (i.p.) was administered as depicted and stopped on day 21, and the mice were allowed to rest for 10 days. The mice were then sacrificed for immunohistochemical analysis and inflammatory gene expression analysis.

To study the therapeutic potential of IL-33 in AD, a 3-week treatment of IL-33 (200 ng; i.p. administration) in WT and APP/PS1 mice (13-months-old) was conducted. The treatment paradigm of IL-33 is shown in FIG. 30. During the course of treatment, beneficial effects of IL-33 on the behavioral deficits in APP/PS1 mice were assessed using behavioral tests including exploratory open field test (OF) and nest building test (NB) (FIG. 30). After the tests, the mice were sacrificed for immunohistochemical analysis or inflammatory gene expression analysis.

For the OF test, the locomotor activity of the mice was recorded and tracked using the photobeam activity system and software (San Diego Instruments). Experimental mice were placed in the center of an open-top chamber and were allowed to explore the chamber for 15 min each day for 3 consecutive days. Locomotor activity in the 3 training trials was recorded by the photobeams, and the distance moved was subsequently determined. For the NB test, the mice were individually housed in new plastic cages with approximately 1 cm corn cob bedding lining the floor. Prior to the onset of the dark phase of the lighting cycle, each mouse was supplied with a nestlet pressed cotton square (~3 g each). Nestlet nest construction was scored on day 1 using a 5-point scale (1 indicates a >90% intact nestlet, and 5 indicates a nestlet torn >90% and a clear nest crater). All tests were performed during the light phase.

For examining the amyloid plaque load, coronal cryosections of 20 μm thickness were sectioned from perfused mouse brains and subjected to 4G8 (Aβ antibody) immunostaining. Antigen retrieval was performed by microwave heating the sections in sodium citrate buffer followed by incubation with 3% $H_2O_2$ in $H_2O$ for 5 min to inhibit endogenous peroxidase activity. The sections were then labeled with 4G8 antibody (dilution 1:500) followed with a Dako HRP-linked goat anti-mouse IgG antibody and developed with a Dako DAB chromogen kit. Imaging was performed using a Leica DM6000 B compound microscope system. The area of Aβ plaques in the cortex of the brain sections was analyzed by the "Analyze Particles" function of Image J (National Institutes of Health). The area of the cortex used for amyloid plaque analysis was the region above the hippocampus. Three brain sections per mouse (with ~200-300 μm apart) were subjected to analysis, and the average percentage of cortical area occupied by amyloid plaques was calculated.

For real time-qPCR analysis, cDNA after RT was pre-amplified using TaqMan PreAmp Master Mix (Invitrogen). The PCR amplification and real-time detection of PCR products were performed using TaqMan gene expression assay (Applied Biosystems) and Premix Ex Taq qPCR assay (TaKaRa). PCRs were conducted in a total volume of 20 μL containing 2 μL pre-amplified product. The mRNA expression values were normalized to the level of β-actin.

Results.

Figure 31B:
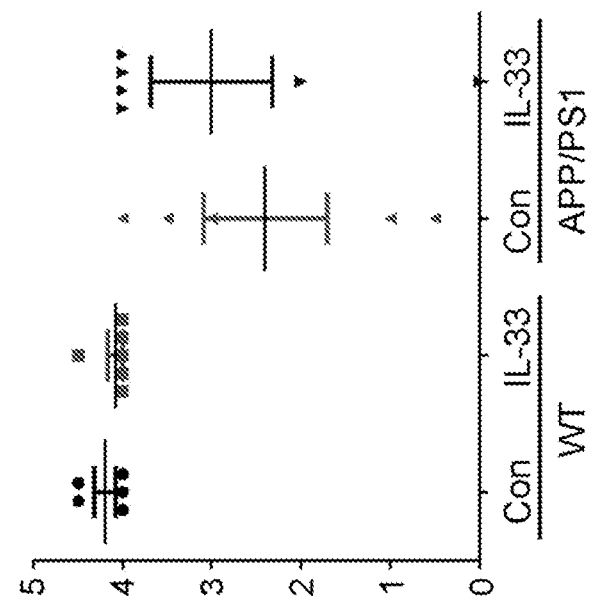
FIGS. 31A-31B demonstrate that IL-33-treated APP/PS1 mice (i.p.) showed a trend of improved behavioral performance in OF and NB tests. IL-33-treated APP/PS1 mice exhibited a trend of improving habituation in the OF test (FIG. 31A). IL-33 administration exhibited a trend of increased nest-building activities in APP/PS1 mice (FIG. 31B). (n=5-6 mice per each experimental group).
Figure 31A:
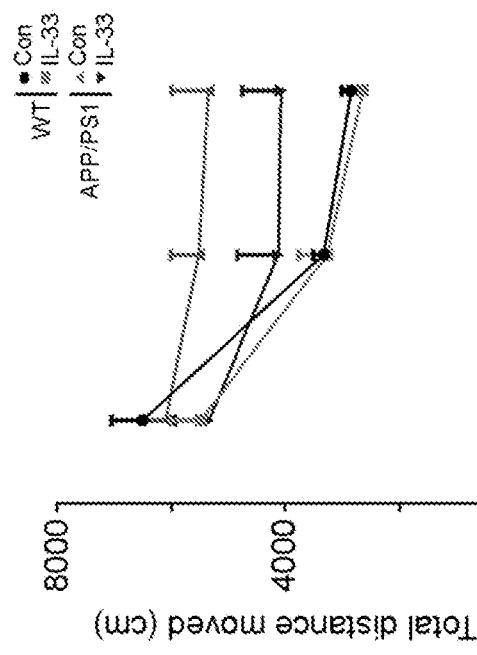

APP/PS1 mice exhibited better performance in the behavioral tests after IL-33 injection (FIGS. 31A-31B). IL-33-administered APP/PS1 mice showed a trend to improved performance in the two behavioral tests (i.e., OF and NB tests) when compared with DPBS (Con)-treated APP/PS1 mice (FIGS. 31A-31B). Chronic treatment of IL-33 also ameliorated the amyloid plaque load in APP/PS1 mice (FIGS. 32A-32B). Furthermore, IL-33 modulated the global inflammation by reducing expression of inflammatory genes in the brain cortices of APP/PS1 mice (FIGS. 33A-33C).

Example 24: Efficacy of Human IL-33 in APP/PS1 Mice

Materials and Methods.

To examine whether human IL-33 (hIL-33) exerts similar beneficial effect as that of mouse IL-33 in AD, APP/PS1 mice at 8-9.5-months-old were used. In particular, recombinant hIL-33 obtained from BioLegend (581802) was administered into WT or APP/PS1 mice via i.p. injection (200 ng in 300 μl/mouse/day) for two consecutive days. Hippocampi were dissected and subjected to LTP analysis at Schaffer collateral-CA1 synapses in the hippocampus. LTP was induced by 3 trains of high-frequency stimulation (100 Hz for 1 s delivered 30 s apart).

Results.

Figure 34B:
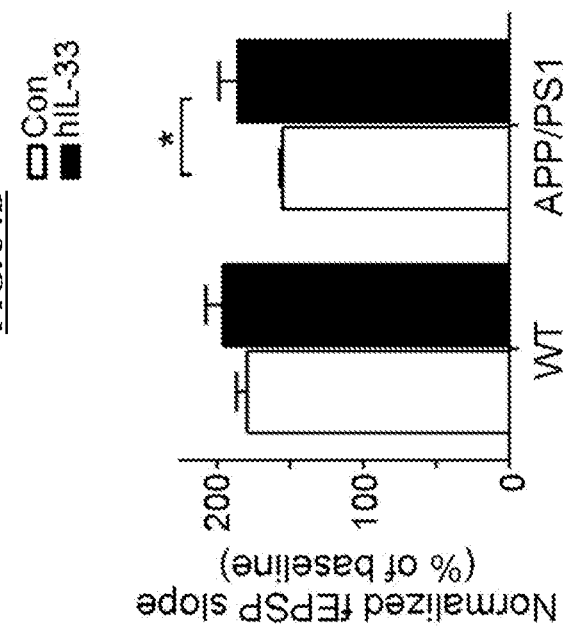
FIGS. 34A-34B show that human IL-33 (hIL-33) reversed the LTP impairment in APP/PS1 mice. Wild-type (WT) and APP/PS1 mice were i.p. administered hIL-33 or vehicle control (Con) for two consecutive days. LTP in the hippocampal CA1 region was induced by HFS.
Figure 34A:
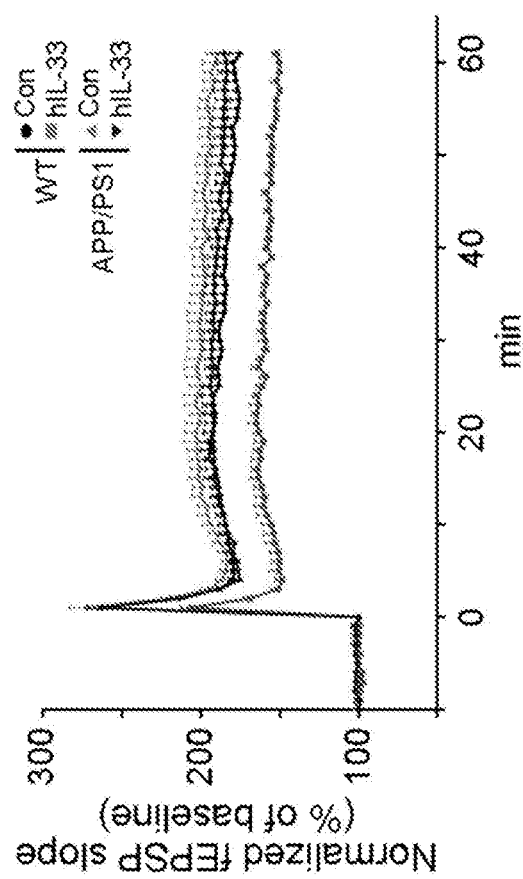

The data presented in FIGS. 34A-34B shows that hIL-33 exhibited the bioactivity of ameliorating the synaptic deficit in APP/PS1 mice.

CONCLUSION

The findings disclosed herein illustrate that methods and compositions disclosed herein are effective for the treatment or prevention of diseases or conditions resulting from, caused by, or otherwise associated with neurodegeneration and/or neuroinflammation.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications, including GenBank Accession Numbers, referred to or cited herein are incorporated by reference in their entirety, including all figures and tables, to the extent they are not inconsistent with the explicit teachings of this specification.

Other embodiments are set forth within the following claims.

What is claimed is:

1. A method for treating Alzheimer's disease in a subject in need thereof, comprising to the subject an effective amount of a composition comprising IL-33 and memantine, wherein the therapeutically effective dosage of IL-33 in the composition is from about 0.000001 mg to about 0.001 mg per kilogram body weight per day.

2. The method of claim 1, wherein the IL-33 protein comprises an amino acid sequence at least 85% identity to SEQ ID NO: 1, SEQ ID NO: 2, SEQ ID NO: 3, or SEQ ID NO: 4, or functional fragments or variants thereof.

3. The method of claim 1, wherein IL-33 protein selected from the group consisting of SEQ ID NO: 1, SEQ ID NO: 2, a polypeptide having at least 85% identity to SEQ ID NO: 1, and a polypeptide having at least 85% identity to SEQ ID NO: 2.

* * * * *

UNITED STATES PATENT AND TRADEMARK OFFICE
CERTIFICATE OF CORRECTION

Page 1 of 1

PATENT NO. : 10,813,979 B2
APPLICATION NO. : 15/742582
DATED : October 27, 2020
INVENTOR(S) : Kit Yu Fu et al.

It is certified that error appears in the above-identified patent and that said Letters Patent is hereby corrected as shown below:

In the Claims

Column 53 Claim 1, Line 27 should read: "in need thereof, comprising administering to the subject an effective"

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 8

<210> SEQ ID NO 1
<211> LENGTH: 270
<212> TYPE: PRT
<213> ORGANISM: Homo sapiens

<400> SEQUENCE: 1

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 2
```

<211> LENGTH: 159
<212> TYPE: PRT
<213> ORGANISM: Homo sapiens

<400> SEQUENCE: 2

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
            100                 105                 110

His Ser Asn Cys Val Ser Phe Glu Cys Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr
145                 150                 155

<210> SEQ ID NO 3
<211> LENGTH: 266
<212> TYPE: PRT
<213> ORGANISM: Mus musculus

<400> SEQUENCE: 3

Met Arg Pro Arg Met Lys Tyr Ser Asn Ser Lys Ile Ser Pro Ala Lys
1               5                   10                  15

Phe Ser Ser Thr Ala Gly Glu Ala Leu Val Pro Pro Cys Lys Ile Arg
            20                  25                  30

Arg Ser Gln Gln Lys Thr Lys Glu Phe Cys His Val Tyr Cys Met Arg
        35                  40                  45

Leu Arg Ser Gly Leu Thr Ile Arg Lys Glu Thr Ser Tyr Phe Arg Lys
    50                  55                  60

Glu Pro Thr Lys Arg Tyr Ser Leu Lys Ser Gly Thr Lys His Glu Glu
65                  70                  75                  80

Asn Phe Ser Ala Tyr Pro Arg Asp Ser Arg Lys Arg Ser Leu Leu Gly
                85                  90                  95

Ser Ile Gln Ala Phe Ala Ala Ser Val Asp Thr Leu Ser Ile Gln Gly
            100                 105                 110

Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
    130                 135                 140

Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Leu Met Val Asn Met Ser Pro Ile Lys Asp Thr Asp Ile Trp
            180                 185                 190

```
Leu His Ala Asn Asp Lys Asp Tyr Ser Val Glu Leu Gln Arg Gly Asp
        195                 200                 205

Val Ser Pro Pro Glu Gln Ala Phe Phe Val Leu His Lys Lys Ser Ser
    210                 215                 220

Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
                245                 250                 255

Asn Asn Ile Met Phe Lys Leu Ser Lys Ile
            260                 265

<210> SEQ ID NO 4
<211> LENGTH: 158
<212> TYPE: PRT
<213> ORGANISM: Mus musculus

<400> SEQUENCE: 4

Ser Ile Gln Gly Thr Ser Leu Leu Thr Gln Ser Pro Ala Ser Leu Ser
1               5                   10                  15

Thr Tyr Asn Asp Gln Ser Val Ser Phe Val Leu Glu Asn Gly Cys Tyr
            20                  25                  30

Val Ile Asn Val Asp Asp Ser Gly Lys Asp Gln Glu Gln Asp Gln Val
        35                  40                  45

Leu Leu Arg Tyr Tyr Glu Ser Pro Cys Pro Ala Ser Gln Ser Gly Asp
    50                  55                  60

Gly Val Asp Gly Lys Lys Leu Met Val Asn Met Ser Pro Ile Lys Asp
65                  70                  75                  80

Thr Asp Ile Trp Leu His Ala Asn Asp Lys Asp Tyr Ser Val Glu Leu
                85                  90                  95

Gln Arg Gly Asp Val Ser Pro Pro Glu Gln Ala Phe Phe Val Leu His
            100                 105                 110

Lys Lys Ser Ser Asp Phe Val Ser Phe Glu Cys Lys Asn Leu Pro Gly
        115                 120                 125

Thr Tyr Ile Gly Val Lys Asp Asn Gln Leu Ala Leu Val Glu Glu Lys
    130                 135                 140

Asp Glu Ser Cys Asn Asn Ile Met Phe Lys Leu Ser Lys Ile
145                 150                 155

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcgaaatgaa agttccagca                                              20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtgtgaggg acactcctta c                                            21
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catggcatga taaggcacac                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtagagcttg ccatcgttcc                                              20